(12) United States Patent
Hariton et al.

(10) Patent No.: US 10,524,903 B2
(45) Date of Patent: Jan. 7, 2020

(54) PROSTHETIC VALVE WITH ALIGNED INNER AND OUTER FRAMES

(71) Applicant: CARDIOVALVE LTD., Or Yehuda (IL)

(72) Inventors: Ilia Hariton, Zichron Yaackov (IL); Boaz Harari, Ganey Tikva (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 16/507,357

(22) Filed: Jul. 10, 2019

(65) Prior Publication Data

US 2019/0328519 A1     Oct. 31, 2019

Related U.S. Application Data

(63) Continuation of application No. 15/978,494, filed on May 14, 2018, now Pat. No. 10,357,360, which is a
(Continued)

(51) Int. Cl.
| | | |
|---|---|---|
| *A61F 2/24* | (2006.01) | |
| *A61F 2/915* | (2013.01) | |
| *A61F 2/95* | (2013.01) | |

(52) U.S. Cl.
CPC ............ *A61F 2/2418* (2013.01); *A61F 2/243* (2013.01); *A61F 2/2409* (2013.01);
(Continued)

(58) Field of Classification Search
CPC ...... A61F 2/243; A61F 2/2418; A61F 2/2409; A61F 2/2436
See application file for complete search history.

(56) References Cited

U.S. PATENT DOCUMENTS

| | | |
|---|---|---|
| 4,261,342 A | 4/1981 | Aranguren |
| 4,275,469 A | 6/1981 | Gabbay |
| | (Continued) | |

FOREIGN PATENT DOCUMENTS

| | | |
|---|---|---|
| EP | 0170262 | 2/1986 |
| EP | 1264582 | 12/2002 |
| | (Continued) | |

OTHER PUBLICATIONS

An Office Action dated Oct. 23, 2017, which issued during the prosecution of U.S. Appl. No. 14/763,004.
(Continued)

*Primary Examiner* — Tuan V Nguyen
(74) *Attorney, Agent, or Firm* — Finnegan, Henderson, Farabow, Garrett & Dunner, L.L.P.

(57) ABSTRACT

Prosthetic valves and methods of use of prosthetic valves may be provided. In one implementation, an expandable prosthetic valve may be configured for implantation within a native heart valve. The prosthetic valve may include an expandable outer frame formed at least partially of outer frame struts. The prosthetic valve may also include an inner frame with tissue anchors extending therefrom, the inner frame being formed at least partially of inner frame struts. The struts along the downstream ends of the outer and inner frames may be arranged in undulating configurations to extend between peaks and troughs. A trough of the outer frame may be configured to be situated downstream from a peak of the inner frame.

20 Claims, 15 Drawing Sheets

Related U.S. Application Data continuation of application No. 15/541,783, filed as application No. PCT/IL2016/050125 on Feb. 3, 2016, now Pat. No. 9,974,651.

(60) Provisional application No. 62/112,343, filed on Feb. 5, 2015.

(52) U.S. Cl.
CPC .. *A61F 2/2436* (2013.01); *A61F 2002/91575* (2013.01); *A61F 2002/9517* (2013.01); *A61F 2220/0016* (2013.01); *A61F 2220/0025* (2013.01)

(56) References Cited

U.S. PATENT DOCUMENTS

| | | |
|---|---|---|
| 4,423,525 A | 1/1984 | Vallana et al. |
| 4,853,986 A | 8/1989 | Allen |
| 4,892,541 A | 1/1990 | Alonso |
| 4,994,077 A | 2/1991 | Dobben |
| 5,078,739 A | 1/1992 | Martin |
| 5,108,420 A | 4/1992 | Marks |
| 5,314,473 A | 5/1994 | Godin |
| 5,332,402 A | 7/1994 | Teitelbaum |
| 5,397,351 A | 3/1995 | Pavcnik et al. |
| 5,405,378 A | 4/1995 | Strecker |
| 5,443,500 A | 8/1995 | Sigwart |
| 5,473,812 A | 12/1995 | Morris et al. |
| 5,607,444 A | 3/1997 | Lam |
| 5,607,470 A | 3/1997 | Milo |
| 5,647,857 A | 7/1997 | Anderson et al. |
| 5,702,397 A | 12/1997 | Goble et al. |
| 5,765,682 A | 6/1998 | Bley et al. |
| 5,868,777 A | 2/1999 | Lam |
| 5,873,906 A | 2/1999 | Lau et al. |
| 5,954,766 A | 9/1999 | Zadno-Azizi et al. |
| 5,980,565 A | 11/1999 | Jayaraman |
| 6,010,530 A | 1/2000 | Goicoechea |
| 6,019,787 A | 2/2000 | Richard et al. |
| 6,042,607 A | 3/2000 | Williamson, IV |
| 6,059,827 A | 5/2000 | Fenton |
| 6,074,417 A | 6/2000 | Peredo |
| 6,113,612 A | 9/2000 | Swanson et al. |
| 6,120,534 A | 9/2000 | Ruiz |
| 6,152,937 A | 11/2000 | Peterson et al. |
| 6,165,210 A | 12/2000 | Lau et al. |
| 6,187,020 B1 | 2/2001 | Zegdi et al. |
| 6,193,745 B1 | 2/2001 | Fogarty et al. |
| 6,264,700 B1 | 7/2001 | Kilcoyne et al. |
| 6,287,339 B1 | 9/2001 | Vazquez et al. |
| 6,312,465 B1 | 11/2001 | Griffin et al. |
| 6,332,893 B1 | 12/2001 | Mortier et al. |
| 6,334,873 B1 | 1/2002 | Lane et al. |
| 6,350,278 B1 | 2/2002 | Lenker et al. |
| 6,352,561 B1 | 3/2002 | Leopold et al. |
| 6,391,036 B1 | 5/2002 | Berg et al. |
| 6,402,780 B2 | 6/2002 | Williamson, IV |
| 6,409,755 B1 | 6/2002 | Vrha |
| 6,419,696 B1 | 7/2002 | Ortiz et al. |
| 6,428,550 B1 | 8/2002 | Vargas et al. |
| 6,440,164 B1 | 8/2002 | Dimatteo et al. |
| 6,454,799 B1 | 9/2002 | Schreck |
| 6,458,153 B1 | 10/2002 | Bailey et al. |
| 6,482,228 B1 | 11/2002 | Norred |
| 6,511,491 B2 | 1/2003 | Grudem et al. |
| 6,530,952 B2 | 3/2003 | Vesely |
| 6,540,782 B1 | 4/2003 | Snyders |
| 6,551,350 B1 | 4/2003 | Thornton et al. |
| 6,558,396 B1 | 5/2003 | Inoue |
| 6,558,418 B2 | 5/2003 | Carpentier et al. |
| 6,569,196 B1 | 5/2003 | Vesely |
| 6,602,263 B1 | 8/2003 | Swanson et al. |
| 6,616,675 B1 | 9/2003 | Evard et al. |
| 6,652,556 B1 | 11/2003 | VanTassel et al. |
| 6,669,724 B2 | 12/2003 | Park et al. |
| 6,682,558 B2 | 1/2004 | Tu et al. |
| 6,699,256 B1 | 3/2004 | Logan et al. |
| 6,716,244 B2 | 4/2004 | Klaco |
| 6,719,781 B1 | 4/2004 | Kim |
| 6,719,788 B2 | 4/2004 | Cox |
| 6,730,118 B2 | 5/2004 | Spenser et al. |
| 6,733,525 B2 | 5/2004 | Yang et al. |
| 6,764,518 B2 | 7/2004 | Godin |
| 6,767,362 B2 | 7/2004 | Schreck |
| 6,797,002 B2 | 9/2004 | Spence et al. |
| 6,821,297 B2 | 11/2004 | Snyders |
| 6,830,585 B1 | 12/2004 | Artof et al. |
| 6,830,638 B2 | 12/2004 | Boylan et al. |
| 6,893,460 B2 | 5/2005 | Spenser et al. |
| 6,960,217 B2 | 11/2005 | Bolduc |
| 6,964,684 B2 | 11/2005 | Ortiz et al. |
| 6,974,476 B2 | 12/2005 | McGuckin, Jr. et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,077,861 B2 | 7/2006 | Spence |
| 7,101,395 B2 | 9/2006 | Tremulis et al. |
| 7,101,396 B2 | 9/2006 | Artof et al. |
| 7,137,184 B2 | 11/2006 | Schreck |
| 7,172,625 B2 | 2/2007 | Shu et al. |
| 7,175,656 B2 | 2/2007 | Khairkhahan |
| 7,198,646 B2 | 4/2007 | Figulla et al. |
| 7,201,772 B2 | 4/2007 | Schwammenthal |
| 7,226,477 B2 | 6/2007 | Cox |
| 7,288,111 B1 | 10/2007 | Holloway et al. |
| 7,316,716 B2 | 1/2008 | Egan |
| 7,329,279 B2 | 2/2008 | Haug et al. |
| 7,335,213 B1 | 2/2008 | Hyde et al. |
| 7,351,256 B2 | 4/2008 | Hojeibane et al. |
| 7,374,573 B2 | 5/2008 | Gabbay |
| 7,377,938 B2 | 5/2008 | Sarac et al. |
| 7,381,218 B2 | 6/2008 | Schreck |
| 7,381,219 B2 | 6/2008 | Salahieh et al. |
| 7,404,824 B1 | 7/2008 | Webler et al. |
| 7,422,603 B2 | 9/2008 | Lane |
| 7,429,269 B2 | 9/2008 | Schwammenthal |
| 7,442,204 B2 | 10/2008 | Schwammenthal |
| 7,445,630 B2 | 11/2008 | Lashinski et al. |
| 7,455,677 B2 | 11/2008 | Vargas et al. |
| 7,455,688 B2 | 11/2008 | Furst et al. |
| 7,462,162 B2 | 12/2008 | Phan et al. |
| 7,481,838 B2 | 1/2009 | Carpentier et al. |
| 7,510,575 B2 | 3/2009 | Spenser et al. |
| 7,513,909 B2 | 4/2009 | Lane et al. |
| 7,524,331 B2 | 4/2009 | Birdsall |
| 7,527,646 B2 | 5/2009 | Rahdert et al. |
| 7,556,646 B2 | 7/2009 | Yang et al. |
| 7,582,111 B2 | 9/2009 | Krolik et al. |
| 7,585,321 B2 | 9/2009 | Cribier |
| 7,597,711 B2 | 10/2009 | Drews et al. |
| 7,611,534 B2 | 11/2009 | Kapadia et al. |
| 7,621,948 B2 | 11/2009 | Herrmann et al. |
| 7,625,403 B2 | 12/2009 | Krivoruchko |
| 7,632,302 B2 | 12/2009 | Vreeman et al. |
| 7,648,528 B2 | 1/2010 | Styre |
| 7,682,380 B2 | 3/2010 | Thornton et al. |
| 7,708,775 B2 | 5/2010 | Rowe et al. |
| 7,717,952 B2 | 5/2010 | Case et al. |
| 7,717,955 B2 | 5/2010 | Lane et al. |
| 7,731,741 B2 | 6/2010 | Eidenschink |
| 7,748,389 B2 | 7/2010 | Salahieh et al. |
| 7,753,922 B2 | 7/2010 | Starksen |
| 7,758,595 B2 | 7/2010 | Allen et al. |
| 7,758,632 B2 | 7/2010 | Hojeibane et al. |
| 7,758,640 B2 | 7/2010 | Vesely |
| 7,771,467 B2 | 8/2010 | Svensson |
| 7,771,469 B2 | 8/2010 | Liddicoat |
| 7,776,083 B2 | 8/2010 | Vesely |
| 7,780,726 B2 | 8/2010 | Seguin |
| 7,785,341 B2 | 8/2010 | Forster et al. |
| 7,799,069 B2 | 9/2010 | Bailey et al. |
| 7,803,181 B2 | 9/2010 | Furst et al. |
| 7,811,316 B2 | 10/2010 | Kalmann et al. |

(56) References Cited

U.S. PATENT DOCUMENTS

| | | |
|---|---|---|
| 7,824,442 B2 | 11/2010 | Salahieh et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,432 B2 | 1/2011 | Bergin |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salabieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,992,567 B2 | 8/2011 | Hirotsuka et al. |
| 7,993,393 B2 | 8/2011 | Carpentier et al. |
| 8,002,825 B2 | 8/2011 | Letac et al. |
| 8,002,826 B2 | 8/2011 | Seguin |
| 8,016,877 B2 | 9/2011 | Seguin et al. |
| 8,016,882 B2 | 9/2011 | Macoviak |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sulivan et al. |
| 8,048,140 B2 | 11/2011 | Purdy |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,080,054 B2 | 11/2011 | Rowe |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde |
| 8,075,611 B2 | 12/2011 | Milwee et al. |
| 8,083,793 B2 | 12/2011 | Lane et al. |
| D652,927 S | 1/2012 | Braido et al. |
| D653,341 S | 1/2012 | Braido et al. |
| 8,092,518 B2 | 1/2012 | Schreck |
| 8,092,520 B2 | 1/2012 | Quadri |
| 8,092,521 B2 | 1/2012 | Figulla et al. |
| 8,105,377 B2 | 1/2012 | Liddicoat |
| 8,109,996 B2 | 2/2012 | Stacchino et al. |
| 8,118,866 B2 | 2/2012 | Herrmann et al. |
| 8,133,270 B2 | 3/2012 | Kheradvar et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,494 B2 | 3/2012 | Rahdert et al. |
| 8,142,496 B2 | 3/2012 | Berreklouw |
| 8,142,497 B2 | 3/2012 | Friedman |
| 8,147,504 B2 | 4/2012 | Ino et al. |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,008 B2 | 4/2012 | Wilson et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,211,169 B2 | 7/2012 | Lane et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,231,670 B2 | 7/2012 | Salahieh et al. |
| 8,236,045 B2 | 8/2012 | Benichou et al. |
| 8,236,049 B2 | 8/2012 | Rowe et al. |
| 8,252,042 B2 | 8/2012 | McNamara et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,267,988 B2 | 9/2012 | Hamer et al. |
| 8,277,501 B2 | 10/2012 | Chalekian et al. |
| 8,287,591 B2 | 10/2012 | Keidar et al. |
| 8,298,280 B2 | 10/2012 | Yadin et al. |
| 8,303,653 B2 | 11/2012 | Bonhoeffer et al. |
| 8,308,798 B2 | 11/2012 | Pintor et al. |
| 8,313,525 B2 | 11/2012 | Tuval et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,337,541 B2 | 12/2012 | Quadri et al. |
| 8,343,174 B2 | 1/2013 | Goldfarb et al. |
| 8,343,213 B2 | 1/2013 | Salahieh et al. |
| 8,348,999 B2 | 1/2013 | Kheradvar et al. |
| 8,366,767 B2 | 2/2013 | Zhang |
| 8,372,140 B2 | 2/2013 | Hoffman et al. |
| 8,377,119 B2 | 2/2013 | Drews et al. |
| 8,398,708 B2 | 3/2013 | Meiri et al. |
| 8,403,981 B2 | 3/2013 | Forster et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,425,593 B2 | 4/2013 | Braido et al. |
| 8,430,934 B2 | 4/2013 | Das |
| 8,444,689 B2 | 5/2013 | Zhang |
| 8,449,599 B2 | 5/2013 | Chau et al. |
| 8,449,625 B2 | 5/2013 | Campbell et al. |
| 8,454,686 B2 | 6/2013 | Alkhatib |
| 8,460,365 B2 | 6/2013 | Haverkost et al. |
| 8,474,460 B2 | 7/2013 | Barrett et al. |
| 8,500,821 B2 | 8/2013 | Sobrino-Serrano et al. |
| 8,512,400 B2 | 8/2013 | Tran et al. |
| 8,539,662 B2 | 9/2013 | Stacchino et al. |
| 8,540,767 B2 | 9/2013 | Zhang |
| 8,545,544 B2 | 10/2013 | Spenser et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,623,075 B2 | 1/2014 | Murray et al. |
| 8,623,080 B2 | 1/2014 | Fogarty et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |

(56) References Cited

U.S. PATENT DOCUMENTS

| | | |
|---|---|---|
| 8,679,174 B2 | 3/2014 | Ottma et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,734,507 B2 | 5/2014 | Keranen |
| 8,747,460 B2 | 6/2014 | Tuval et al. |
| 8,771,345 B2 | 7/2014 | Tuval et al. |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,840,663 B2 | 9/2014 | Salahieh et al. |
| 8,840,664 B2 | 9/2014 | Karapetian et al. |
| 8,845,722 B2 | 9/2014 | Gabbay |
| 8,852,261 B2 | 10/2014 | White |
| 8,852,272 B2 | 10/2014 | Gross et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,489 B2 | 12/2014 | Ben-Muvhar |
| 8,911,493 B2 | 12/2014 | Rowe et al. |
| 8,932,343 B2 | 1/2015 | Alkhatib et al. |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,527 B2 | 4/2015 | Li et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich et al. |
| 9,072,603 B2 | 7/2015 | Tuval et al. |
| 9,084,676 B2 | 7/2015 | Chau et al. |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,738 B2 | 11/2015 | Murray et al. |
| 9,220,594 B2 | 12/2015 | Braido et al. |
| 9,226,820 B2 | 1/2016 | Braido et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,794 B2 | 1/2016 | Braido et al. |
| 9,248,014 B2 | 2/2016 | Lane et al. |
| 9,289,290 B2 | 3/2016 | Alkhatib et al. |
| 9,289,291 B2 | 3/2016 | Gorman et al. |
| 9,295,550 B2 | 3/2016 | Nguyen et al. |
| 9,295,552 B2 | 3/2016 | McLean et al. |
| 9,301,836 B2 | 4/2016 | Buchbinder et al. |
| D755,384 S | 5/2016 | Pesce et al. |
| 9,326,852 B2 | 5/2016 | Spenser |
| 9,345,573 B2 | 5/2016 | Nyuli et al. |
| 9,387,078 B2 | 7/2016 | Gross et al. |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,445,893 B2 | 9/2016 | Vaturi |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,498,332 B2 | 11/2016 | Hacohen et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich et al. |
| 9,572,665 B2 | 2/2017 | Lane et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,182,908 B2 | 1/2019 | Tubishevitz et al. |
| 2001/0021872 A1 | 9/2001 | Bailey et al. |
| 2001/0056295 A1 | 12/2001 | Solem |
| 2002/0032481 A1 | 3/2002 | Gabbay |
| 2002/0099436 A1 | 7/2002 | Thornton et al. |
| 2002/0151970 A1 | 10/2002 | Garrison et al. |
| 2002/0177894 A1 | 11/2002 | Acosta et al. |
| 2003/0036791 A1 | 2/2003 | Bonhoeffer et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |
| 2004/0010272 A1 | 1/2004 | Manetakis et al. |
| 2004/0039414 A1 | 2/2004 | Carley et al. |
| 2004/0093060 A1 | 5/2004 | Seguin et al. |
| 2004/0122503 A1 | 6/2004 | Campbell et al. |
| 2004/0122514 A1 | 6/2004 | Fogarty et al. |
| 2004/0133267 A1 | 7/2004 | Lane |
| 2004/0143315 A1 | 7/2004 | Bruun et al. |
| 2004/0176839 A1 | 9/2004 | Huynh et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0249433 A1 | 12/2004 | Freitag |
| 2004/0260389 A1 | 12/2004 | Case et al. |
| 2004/0260394 A1 | 12/2004 | Douk et al. |
| 2005/0004668 A1 | 1/2005 | Aklog et al. |
| 2005/0021056 A1 | 1/2005 | St. Goar et al. |
| 2005/0038494 A1 | 2/2005 | Eidenschink |
| 2005/0055086 A1 | 3/2005 | Stobie |
| 2005/0075731 A1 | 4/2005 | Artof et al. |
| 2005/0080430 A1 | 4/2005 | Wright et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0137697 A1 | 6/2005 | Salahieh et al. |
| 2005/0143809 A1 | 6/2005 | Salahieh et al. |
| 2005/0154443 A1 | 7/2005 | Linder et al. |
| 2005/0182483 A1 | 8/2005 | Osborne et al. |
| 2005/0182486 A1 | 8/2005 | Gabbay |
| 2005/0197695 A1 | 9/2005 | Stacchino et al. |
| 2005/0203549 A1 | 9/2005 | Realyvasquez |
| 2005/0216079 A1 | 9/2005 | MaCoviak |
| 2005/0234508 A1 | 10/2005 | Cummins et al. |
| 2005/0240200 A1 | 10/2005 | Bergheim |

(56) References Cited

U.S. PATENT DOCUMENTS

| | | |
|---|---|---|
| 2005/0251251 A1 | 11/2005 | Cribier |
| 2005/0267573 A9 | 12/2005 | Macoviak et al. |
| 2006/0004439 A1 | 1/2006 | Spenser et al. |
| 2006/0004469 A1 | 1/2006 | Sokel |
| 2006/0015171 A1 | 1/2006 | Armstrong |
| 2006/0020327 A1 | 1/2006 | Lashinski et al. |
| 2006/0020333 A1 | 1/2006 | Lashinski et al. |
| 2006/0041189 A1 | 2/2006 | Vancaillie |
| 2006/0052867 A1 | 3/2006 | Revuelta et al. |
| 2006/0089627 A1 | 4/2006 | Burnett et al. |
| 2006/0111773 A1 | 5/2006 | Rittgers et al. |
| 2006/0135964 A1 | 6/2006 | Vesley |
| 2006/0161250 A1 | 7/2006 | Shaw |
| 2006/0047297 A1 | 8/2006 | Case |
| 2006/0178700 A1 | 8/2006 | Quinn |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0241656 A1 | 10/2006 | Starksen et al. |
| 2006/0241748 A1 | 10/2006 | Lee et al. |
| 2006/0247680 A1 | 11/2006 | Amplatz et al. |
| 2006/0253191 A1 | 11/2006 | Salableh et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0287719 A1 | 12/2006 | Rowe et al. |
| 2007/0016288 A1 | 1/2007 | Gurskis et al. |
| 2007/0027528 A1 | 2/2007 | Agnew |
| 2007/0027549 A1 | 2/2007 | Godin |
| 2007/0038295 A1 | 2/2007 | Case et al. |
| 2007/0043435 A1 | 2/2007 | Seguin et al. |
| 2007/0055340 A1 | 3/2007 | Pryor |
| 2007/0056346 A1 | 3/2007 | Spenser et al. |
| 2007/0112422 A1 | 5/2007 | Dehdashtian |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0198077 A1 | 8/2007 | Cully et al. |
| 2007/0198097 A1 | 8/2007 | Zegdi |
| 2007/0213810 A1 | 9/2007 | Newhauser et al. |
| 2007/0213813 A1 | 9/2007 | Von Segesser et al. |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kitson |
| 2008/0082083 A1 | 4/2008 | Forde et al. |
| 2008/0082166 A1 | 4/2008 | Styrc et al. |
| 2008/0086164 A1 | 4/2008 | Rowe et al. |
| 2008/0086204 A1 | 4/2008 | Rankin |
| 2008/0091261 A1 | 4/2008 | Long et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195200 A1 | 8/2008 | Vidlund et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0281411 A1 | 11/2008 | Berreklouw |
| 2008/0294234 A1 | 11/2008 | Hartley et al. |
| 2009/0005863 A1 | 1/2009 | Goetz et al. |
| 2009/0054969 A1 | 2/2009 | Salahieh et al. |
| 2009/0088836 A1 | 4/2009 | Bishop et al. |
| 2009/0099650 A1 | 4/2009 | Bolduc et al. |
| 2009/0112159 A1 | 4/2009 | Slattery et al. |
| 2009/0157175 A1 | 6/2009 | Benichou |
| 2009/0171363 A1 | 7/2009 | Chocron |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0248143 A1 | 10/2009 | Laham |
| 2009/0264994 A1 | 10/2009 | Saadat |
| 2009/0276040 A1 | 11/2009 | Rowe et al. |
| 2009/0281619 A1 | 11/2009 | Le et al. |
| 2009/0287304 A1 | 11/2009 | Dahlgren et al. |
| 2009/0299449 A1 | 12/2009 | Styrc |
| 2009/0306768 A1 | 12/2009 | Quardi |
| 2009/0319037 A1 | 12/2009 | Rowe et al. |
| 2010/0023117 A1 | 1/2010 | Yoganathan et al. |
| 2010/0023120 A1 | 1/2010 | Holecek et al. |
| 2010/0036479 A1 | 2/2010 | Hill et al. |
| 2010/0049313 A1 | 2/2010 | Alon et al. |
| 2010/0076548 A1 | 3/2010 | Konno |
| 2010/0100167 A1 | 4/2010 | Bortlein et al. |
| 2010/0114299 A1 | 5/2010 | Ben-Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0256737 A1 | 10/2010 | Pollock et al. |
| 2010/0262232 A1 | 10/2010 | Annest |
| 2010/0280603 A1 | 11/2010 | Maisano et al. |
| 2010/0280606 A1 | 11/2010 | Naor |
| 2010/0312333 A1 | 12/2010 | Navia et al. |
| 2010/0324595 A1 | 12/2010 | Linder et al. |
| 2010/0331971 A1 | 12/2010 | Keränen et al. |
| 2011/0004296 A1 | 1/2011 | Lutter et al. |
| 2011/0015729 A1 | 1/2011 | Jimenez et al. |
| 2011/0015731 A1 | 1/2011 | Carpentier et al. |
| 2011/0022165 A1 | 1/2011 | Oba et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0098525 A1 | 4/2011 | Kermode et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |

(56) References Cited

U.S. PATENT DOCUMENTS

| | | |
|---|---|---|
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144742 A1 | 6/2011 | Madrid et al. |
| 2011/0166636 A1 | 7/2011 | Rowe |
| 2011/0172784 A1 | 7/2011 | Richter |
| 2011/0178597 A9 | 7/2011 | Navia et al. |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Weimeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288634 A1 | 11/2011 | Tuval et al. |
| 2011/0295363 A1 | 12/2011 | Girard et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0022633 A1 | 1/2012 | Olson et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval et al. |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123511 A1 | 5/2012 | Brown |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0150218 A1 | 6/2012 | Sandgren et al. |
| 2012/0165915 A1 | 6/2012 | Melsheimer et al. |
| 2012/0179244 A1 | 7/2012 | Schankereli et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0296360 A1 | 11/2012 | Norris et al. |
| 2012/0310328 A1 | 12/2012 | Olson et al. |
| 2012/0323316 A1 | 12/2012 | Chau et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0035759 A1 | 2/2013 | Gross et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0144381 A1 | 6/2013 | Quadri et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0190861 A1 | 7/2013 | Chau et al. |
| 2013/0211501 A1 | 8/2013 | Buckley et al. |
| 2013/0245742 A1 | 9/2013 | Norris |
| 2013/0261737 A1 | 10/2013 | Costello |
| 2013/0261738 A1 | 10/2013 | Clague et al. |
| 2013/0289711 A1 | 10/2013 | Liddy et al. |
| 2013/0297013 A1 | 11/2013 | Klima et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0331929 A1 | 12/2013 | Mitra et al. |
| 2014/0005778 A1 | 1/2014 | Buchbinder et al. |
| 2014/0018911 A1 | 1/2014 | Zhou et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067054 A1 | 3/2014 | Chau et al. |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Norris |
| 2014/0148891 A1 | 5/2014 | Johnson |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188210 A1 | 7/2014 | Beard et al. |
| 2014/0188221 A1 | 7/2014 | Chung et al. |
| 2014/0194981 A1 | 7/2014 | Menk et al. |

(56) References Cited

U.S. PATENT DOCUMENTS

| | | |
|---|---|---|
| 2014/0194983 A1 | 7/2014 | Kovalsky et al. |
| 2014/0207231 A1 | 7/2014 | Hacohen et al. |
| 2014/0214159 A1 | 7/2014 | Vidlund et al. |
| 2014/0222136 A1 | 8/2014 | Geist et al. |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277358 A1 | 9/2014 | Slazas |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0324164 A1 | 10/2014 | Gross et al. |
| 2014/0343670 A1 | 11/2014 | Bakis et al. |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0018944 A1 | 1/2015 | O'Connell et al. |
| 2015/0045880 A1 | 2/2015 | Hacohen |
| 2015/0045881 A1 | 2/2015 | Lim |
| 2015/0094802 A1 | 4/2015 | Buchbinder et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0173896 A1 | 6/2015 | Richter et al. |
| 2015/0173897 A1 | 6/2015 | Raanani et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0272730 A1 | 10/2015 | Melnick et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2015/0359631 A1 | 12/2015 | Sheahan et al. |
| 2016/0030169 A1 | 2/2016 | Shahriari |
| 2016/0030171 A1 | 2/2016 | Quijano et al. |
| 2016/0095700 A1 | 4/2016 | Righini |
| 2016/0106539 A1 | 4/2016 | Buchbinder et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0184098 A1 | 6/2016 | Vaturi |
| 2016/0213473 A1 | 7/2016 | Hacohen et al. |
| 2016/0220367 A1 | 8/2016 | Barrett |
| 2016/0242902 A1 | 8/2016 | Morriss et al. |
| 2016/0270911 A1 | 9/2016 | Ganesan et al. |
| 2016/0296330 A1 | 10/2016 | Hacohen |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324640 A1 | 11/2016 | Gifford et al. |
| 2016/0331525 A1 | 11/2016 | Straubinger et al. |
| 2016/0331526 A1 | 11/2016 | Schweich et al. |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2017/0042678 A1 | 2/2017 | Ganesan et al. |
| 2017/0056166 A1 | 3/2017 | Ratz et al. |
| 2017/0056171 A1 | 3/2017 | Cooper et al. |
| 2017/0065407 A1 | 3/2017 | Hacohen et al. |
| 2017/0128205 A1 | 5/2017 | Tamir et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0231759 A1 | 8/2017 | Geist et al. |
| 2017/0231760 A1 | 8/2017 | Lane et al. |
| 2018/0049873 A1 | 2/2018 | Manash et al. |
| 2018/0055630 A1 | 3/2018 | Patel et al. |
| 2018/0153689 A1 | 6/2018 | Maimon et al. |

FOREIGN PATENT DOCUMENTS

| | | |
|---|---|---|
| EP | 1264582 A2 | 12/2002 |
| WO | 1999/030647 | 6/1999 |
| WO | 2000-047139 | 8/2000 |
| WO | 2001-062189 | 8/2001 |
| WO | 03/028558 | 4/2003 |
| WO | 2004/108191 | 12/2004 |
| WO | 06/054930 | 5/2006 |
| WO | 2006/070372 | 7/2006 |
| WO | 2006/089236 | 8/2006 |
| WO | 2007/059252 | 5/2007 |
| WO | 08/013915 | 1/2008 |
| WO | WO 2008/029296 A2 | 3/2008 |
| WO | 2008/070797 | 6/2008 |
| WO | 2008/103722 | 8/2008 |
| WO | 09/033469 | 3/2009 |
| WO | 09/053497 | 4/2009 |
| WO | 2009/091509 | 7/2009 |
| WO | 2010/006627 | 1/2010 |
| WO | WO 2010/006627 A1 | 1/2010 |
| WO | WO 2010/057262 A1 | 5/2010 |
| WO | 2010/073246 | 7/2010 |
| WO | 2010/081033 | 7/2010 |
| WO | 2011/069048 | 6/2011 |
| WO | 2011/089601 | 7/2011 |
| WO | 2011/106137 | 9/2011 |
| WO | 2011/111047 | 9/2011 |
| WO | 01/87190 | 11/2011 |
| WO | 2011/137531 | 11/2011 |
| WO | 2011-143263 | 11/2011 |
| WO | 2011/154942 | 12/2011 |
| WO | 2012/011108 | 1/2012 |
| WO | 2012/024428 | 2/2012 |
| WO | 2012/036740 | 3/2012 |
| WO | WO 2012/036740 A2 | 3/2012 |
| WO | WO 2012/048035 A2 | 4/2012 |
| WO | 2012/127309 | 9/2012 |
| WO | 2012/177942 | 12/2012 |
| WO | 2013/021374 | 2/2013 |
| WO | 2013/021375 | 2/2013 |
| WO | 2013/021384 | 2/2013 |
| WO | WO 2013/059747 A1 | 4/2013 |
| WO | 2013/078497 | 6/2013 |
| WO | WO 2013/078497 A1 | 6/2013 |
| WO | 2013/128436 | 9/2013 |
| WO | WO 2013/175468 A2 | 11/2013 |
| WO | 2014/022124 | 2/2014 |
| WO | 2014/076696 | 5/2014 |
| WO | 2014/115149 | 7/2014 |
| WO | 2014/145338 | 9/2014 |
| WO | WO 2014/164364 A1 | 10/2014 |
| WO | 2015/173794 | 11/2015 |
| WO | 2016/016899 | 2/2016 |
| WO | 2016/093877 | 6/2016 |
| WO | WO 2016/098104 A2 | 6/2016 |
| WO | 2016/125160 | 8/2016 |
| WO | WO 2018/025260 A1 | 2/2018 |
| WO | WO 2018/029680 A1 | 2/2018 |
| WO | WO 2018/039631 A1 | 3/2018 |
| WO | WO 2018/106837 A1 | 6/2018 |
| WO | WO 2018/112429 A1 | 6/2018 |
| WO | WO 2018/118717 A1 | 6/2018 |

(56) References Cited

FOREIGN PATENT DOCUMENTS

WO  WO 2018/131042 A1  7/2018
WO  WO 2018/131043 A1  7/2018

OTHER PUBLICATIONS

An Office Action dated Jan. 17, 2018, which issued during the prosecution of U.S. Appl. No. 14/763,004.
An Office Action dated Dec. 7, 2017, which issued during the prosecution of U.S. Appl. No. 15/213,791.
An Office Action dated Feb. 8, 2018, which issued during the prosecution of U.S. Appl. No. 15/213,791.
An Office Action dated Feb. 2, 2018, which issued during the prosecution of U.S. Appl. No. 15/329,920.
An Office Action dated Feb. 7, 2018, which issued during the prosecution of U.S. Appl. No. 15/197,069.
An Invitation to pay additional fees dated Jan. 2, 2018, which issued during the prosecution of Applicant's PCT/IL2017/050849.
An Office Action dated Nov. 23, 2012, which issued during the prosecution of U.S. Appl. No. 13/033,852.
An Office Action dated Dec. 31, 2012, which issued during the prosecution of U.S. Appl. No. 13/044,694.
An Office Action dated Feb. 6, 2013, which issued during the prosecution of U.S. Appl. No. 13/412,814.
Langer F et al., "RING plus STRING: Papillary muscle repositioning as an adjunctive repair technique for ischemic mitral regurgitation," J Thorac Cardiovasc Surg 133:247-9, Jan. 2007.
Langer F et al., "RING+STRING: Successful repair technique for ischemic mitral regurgitation with severe leaflet tethering," Circulation 120[suppl 1]: S85-S91, Sep. 2009.
"Transcatheter Valve-in-Valve Implantation for Failed Bioprosthetic Heart Valves", J Webb et al., Circulation. Apr. 2010; 121: 1848-1857.
Jansen, J., Willeke, S., Reul, H, and Rum, G. (1992), Detachable Shape-Memory Sewing Ring for Heart Valves. Artificial Organs, 16:294-297. 1992 (an abstract).
Alexander S. Geha, et al., Replacement of degenerated mitral and aortic bioprostheses without explanation Ann Thorac Surg. Jun. 2001; 72:1509-1514.
An International Search Report and a Written Opinion both dated Oct. 13, 2011 which issued during the prosecution of Applicant's PCT/IL11/00231.
An Office Action dated Jul. 1, 2016, which issued during the prosecution of U.S. Appl. No. 14/161,921.
An International Search Report and a Written Opinion both dated Dec. 5, 2011, which issued during the prosecution of Applicant's PCT/IL11/00582.
An Office Action dated May 29, 2012, which issued during the prosecution of U.S. Appl. No. 12/840,463.
U.S. Appl. No. 61/555,160, filed Nov. 3, 2011.
U.S. Appl. No. 61/525,281, filed Aug. 19, 2011.
U.S. Appl. No. 61/537,276, filed Sep. 21, 2011.
U.S. Appl. No. 61/515,372, filed Aug. 5, 2011.
U.S. Appl. No. 61/492,449, filed Jun. 2, 2011.
U.S. Appl. No. 61/588,892, filed Jan. 20, 2012.
An International Search Report and a Written Opinion both dated Feb. 6, 2013, which issued during the prosecution of Applicant's PCT/IL12/00292.
An International Search Report and a Written Opinion both dated Feb. 6, 2013, which issued during the prosecution of Applicant's PCT/IL12/00293.
An Office Action dated Nov. 28, 2012, which issued during the prosecution of U.S. Appl. No. 12/961,721.
An Office Action dated Feb. 15, 2013, which issued during the prosecution of U.S. Appl. No. 12/840,463.
An Office Action dated Feb. 10, 2014, which issued during the prosecution of U.S. Appl. No. 13/033,852.
An Office Action dated Sep. 19, 2014, which issued during the prosecution of U.S. Appl. No. 13/044,694.

An International Search Report and a Written Opinion both dated Sep. 4, 2014 which issued during the prosecution of Applicant's PCT/IL2014/050087.
Invitation to Pay Additional Fees dated Jun. 12, 2014 PCT/IL2014/050087.
An Office Action dated Jun. 17, 2014, which issued during the prosecution of U.S. Appl. No. 12/961,721.
An Office Action dated Jul. 3, 2014, which issued during the prosecution of U.S. Appl. No. 13/033,852.
An Office Action dated May 23, 2014, which issued during the prosecution of U.S. Appl. No. 13/412,814.
Dominique Himbert; Mitral Regurgitation and Stenosis from Bioprosthesis and Annuloplasty Failure: Transcatheter approaches and outcomes, 24 pages Oct. 28, 2013.
An International Search Report and a Written Opinion both dated Mar. 17, 2014 which issued during the prosecution of Applicant's PCT/IL2013/050937.
An International Preliminary Report on Patentabilty dated Dec. 2, 2013, which issued during the prosecution of Applicant's PCT/IL11/00582.
An Office Action dated Sep. 12, 2013, which issued during the prosecution of U.S. Appl. No. 13/412,814.
An Office Action dated Aug. 2, 2013, which issued during the prosecution of U.S. Appl. No. 13/033,852.
An International Preliminary Report on patentabilty dated Sep. 11, 2012, which issued during the prosecution of Applicant's PCT/IL2011/000231.
An Office Action dated Jul. 2, 2014, which issued during the prosecution of U.S. Appl. No. 13/811,308.
An Office Action dated Jan. 20, 2016, which issued during the prosecution of U.S. Appl. No. 14/161,921.
An Office Action dated Jul. 23, 2013, which issued during the prosecution of U.S. Appl. No. 12/961,721.
An Office Action dated Jul. 18, 2013, which issued during the prosecution of U.S. Appl. No. 13/044,694.
An Office Action dated Nov. 8, 2013, which issued during the prosecution of U.S. Appl. No. 12/840,463.
An Office Action dated Jun. 4, 2014, which issued during the prosecution of U.S. Appl. No. 12/840,463.
An Office Action dated Aug. 13, 2012, which issued during the prosecution of U.S. Appl. No. 13/044,694.
An Office Action dated Jul. 2, 2012, which issued during the prosecution of U.S. Appl. No. 13/033,852.
An Office Action dated Feb. 3, 2014, which issued during the prosecution of U.S. Appl. No. 13/811,308.
An International Preliminary Report on patentabilty dated Feb. 11, 2014, which issued during the prosecution of Applicant's PCT/IL12/00292.
An International Preliminary Report on patentabilty dated Feb. 11, 2014, which issued during the prosecution of Applicant's PCT/IL12/00293.
A Notice of Allowance dated Aug. 15, 2014, which issued during the prosecution of U.S. Appl. No. 13/412,814.
An Office Action dated Aug. 14, 2012, which issued during the prosecution of U.S. Appl. No. 12/961,721.
U.S. Appl. No. 61/283,819, filed Dec. 8, 2009.
Notice of Allowance dated Sep. 29, 2016, which issued during the prosecution of U.S. Appl. No. 14/442,541.
U.S. Appl. No. 61/756,034, filed Jan. 24, 2013.
U.S. Appl. No. 61/756,049, filed Jan. 24, 2013.
Notice of Allowance dated Jul. 1, 2016, which issued during the prosecution of U.S. Appl. No. 14/442,541.
An Office Action dated Mar. 25, 2015, which issued during the prosecution of U.S. Appl. No. 12/840,463.
Notice of Allowance dated May 5, 2015, which issued during the prosecution of U.S. Appl. No. 12/840,463.
Georg Lutter, MD, et al ; "Percutaneous Valve Replacement: Current State and Future Prospects", The Annals of Thoracic Surgery ; vol. 78, pp. 2199-2206; Dec. 2004.
An Office Action dated Dec. 10, 2015, which issued during the prosecution of U.S. Appl. No. 14/237,258.

(56) References Cited

OTHER PUBLICATIONS

An International Preliminary Report on Patentability dated Jul. 28, 2015, which issued during the prosecution of Applicant's PCT/IL2014/050087.
An Office Action dated Nov. 27, 2015, which issued during the prosecution of U.S. Appl. No. 14/626,267.
An Office Action dated Jan. 21, 2016, which issued during the prosecution of U.S. Appl. No. 14/237,264.
An Office Action dated Apr. 13, 2016, which issued during the prosecution of U.S. Appl. No. 14/626,267.
An International Search Report and a Written Opinion both dated May 30, 2016, which issued during the prosecution of Applicant's PCT/IL2016/050125.
An Office Action dated Sep. 26, 2016, which issued during the prosecution of U.S. Appl. No. 14/763,004.
An Office Action dated Jan. 18, 2017, which issued during the prosecution of U.S. Appl. No. 14/626,267.
An Office Action dated Feb. 7, 2017, which issued during the prosecution of U.S. Appl. No. 14/689,608.
An Office Action dated Feb. 8, 2017, which issued during the prosecution of UK Patent Application No. 1613219.3.
An Office Action together dated Feb. 10, 2017, which issued during the prosecution of European Patent Application No. 12821522.5.
An International Search Report and a Written Opinion both dated Oct. 27, 2015, which issued during the prosecution of Applicant's PCT/IL2015/050792.
European Search Report dated Feb. 18, 2015, which issued during the prosecution of Applicant's European App No. 12821522.5.
Saturn Project—a novel solution for transcatheter heart valve replacement specifically designed to address clinical therapeutic needs on mitral valve: Dec. 2016.
Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve-interventions).
An International Preliminary Report on Patentability dated Jan. 31, 2017, which issued during the prosecution of Applicant's PCT/IL2015/050792.
An Office Action dated Jan. 30, 2015, which issued during the prosecution of UK Patent Application No. 1413474.6.
An International Preliminary Report on Patentability dated May 19, 2015, which issued during the prosecution of Applicant's PCT/IL2013/050937.
Dusan Pavcnik, MD, PhD2, et al; "Development and Initial Experimental Evaluation of a Prosthetic Aortic Valve for Transcatheter Placement", Cardiovascular Radiology. Radiology Apr. 1992, vol. 183, pp. 151-154.
Notice of Allowance dated Oct. 16, 2013, which issued during the prosecution of U.S. Appl. No. 13/675,119.
Notice of Allowance dated Feb. 11, 2015, which issued during the prosecution of U.S. Appl. No. 13/033,852.
Notice of Allowance dated Mar. 10, 2015, which issued during the prosecution of U.S. Appl. No. 13/811,308.
An Office Action dated Aug. 28, 2015, which issued during the prosecution of U.S. Appl. No. 14/237,264.
Notice of Allowance dated Apr. 8, 2016, which issued during the prosecution of U.S. Appl. No. 14/237,258.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,258.
An Office Action dated Jun. 30, 2015, which issued during the prosecution of U.S. Appl. No. 14/522,987.
An Office Action dated Feb. 25, 2016, which issued during the prosecution of U.S. Appl. No. 14/522,987.
Notice of Allowance dated Dec. 13, 2013, which issued during the prosecution of U.S. Appl. No. 13/675,119.
An International Preliminary Report on Patentability dated Aug. 8, 2017, which issued during the prosecution of Applicant's PCT/IL2016/050125.
Maisano (2015) TCR presentation re Cardiovalve.
U.S. Appl. No. 62/112,343, filed Feb. 5, 2015.
International Search Report dated May 30, 2016, by the European Patent Office in PCT/IL2016/050125 (6 pages).
Written Opinion of the International Searching Authority issued by the European Patent Office in PCT/IL2016/050125 (7 pages).
European Search Report dated Jun. 29, 2017, which issued during the prosecution of Applicant's European App. No. 11809374.9.
An Invitation to pay additional fees dated Sep. 29, 2017, which issued during the prosecution of Applicant's PCT/IL2017/050873.

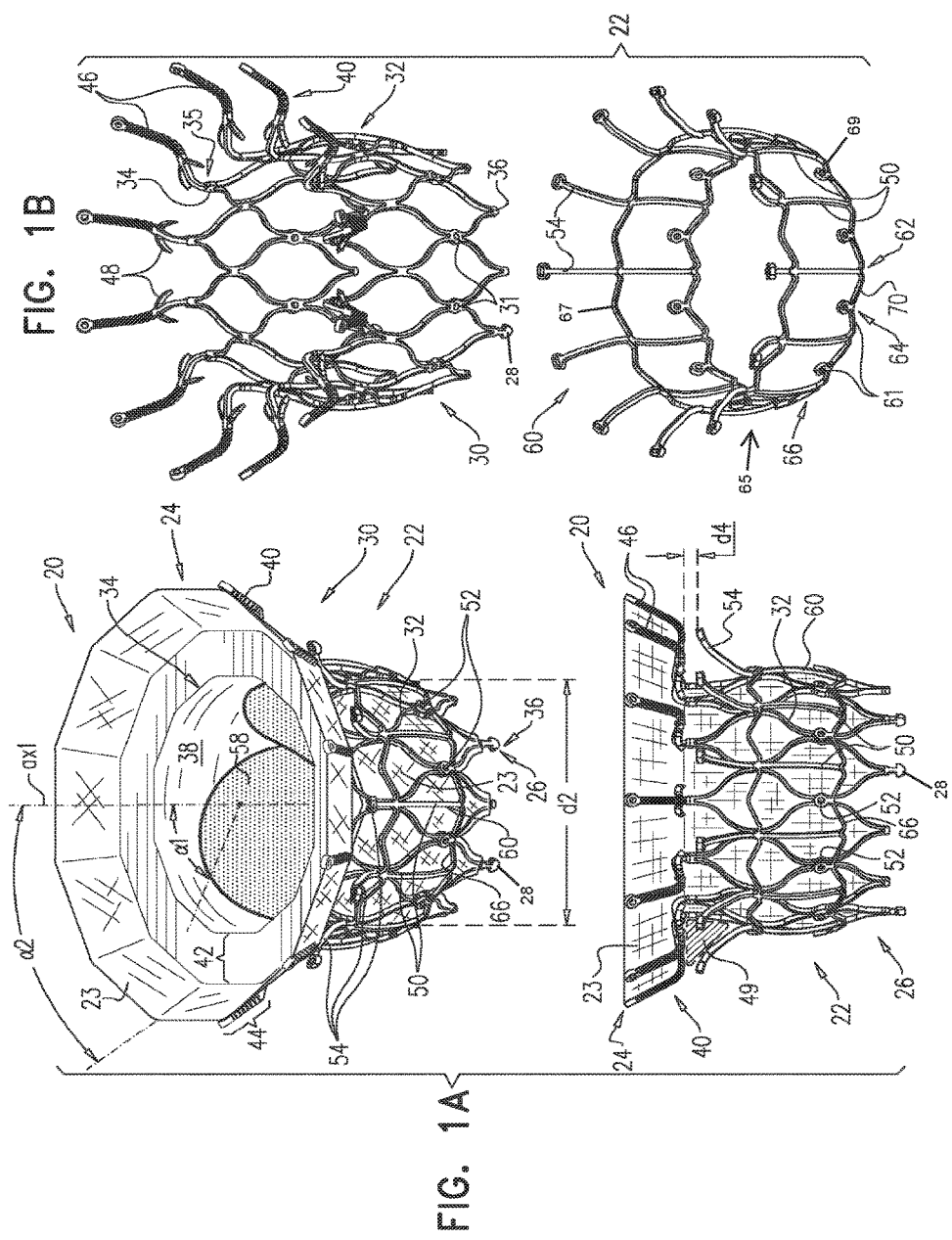

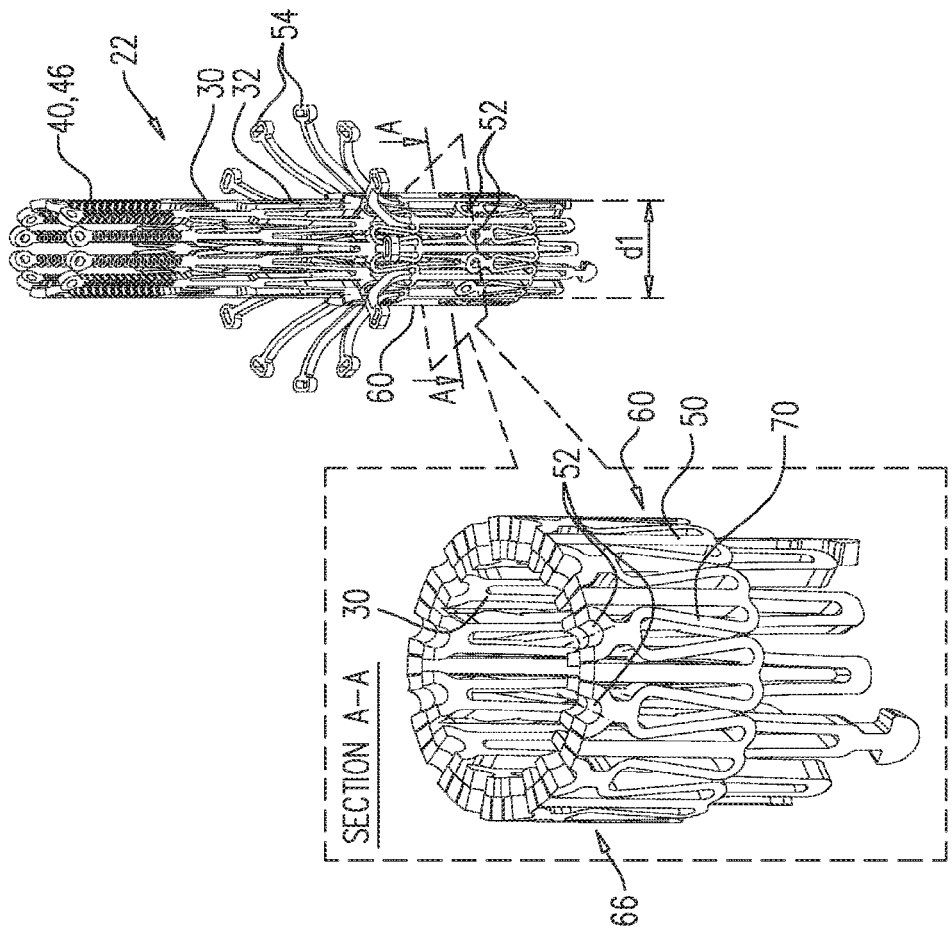
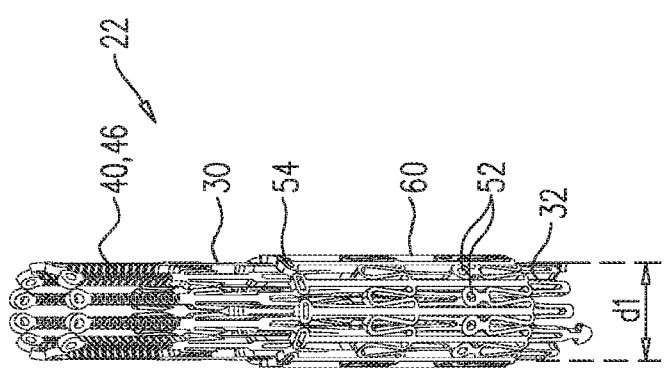

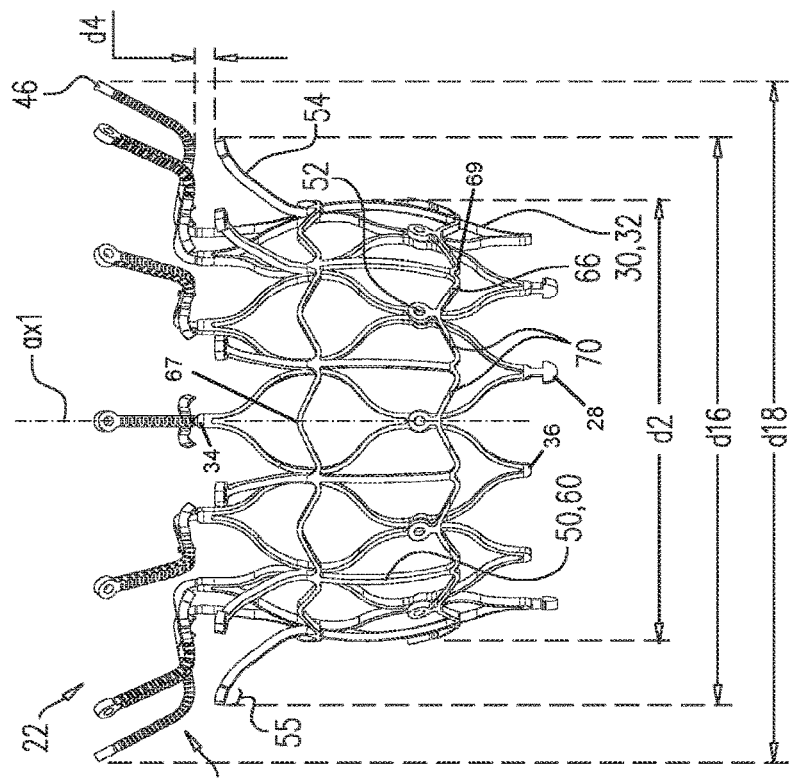
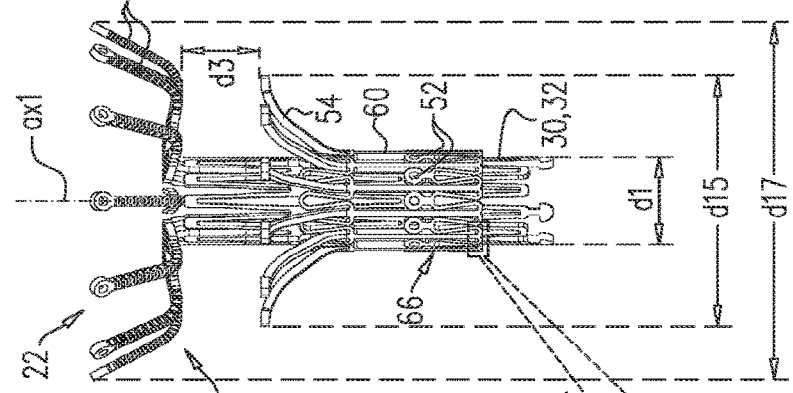
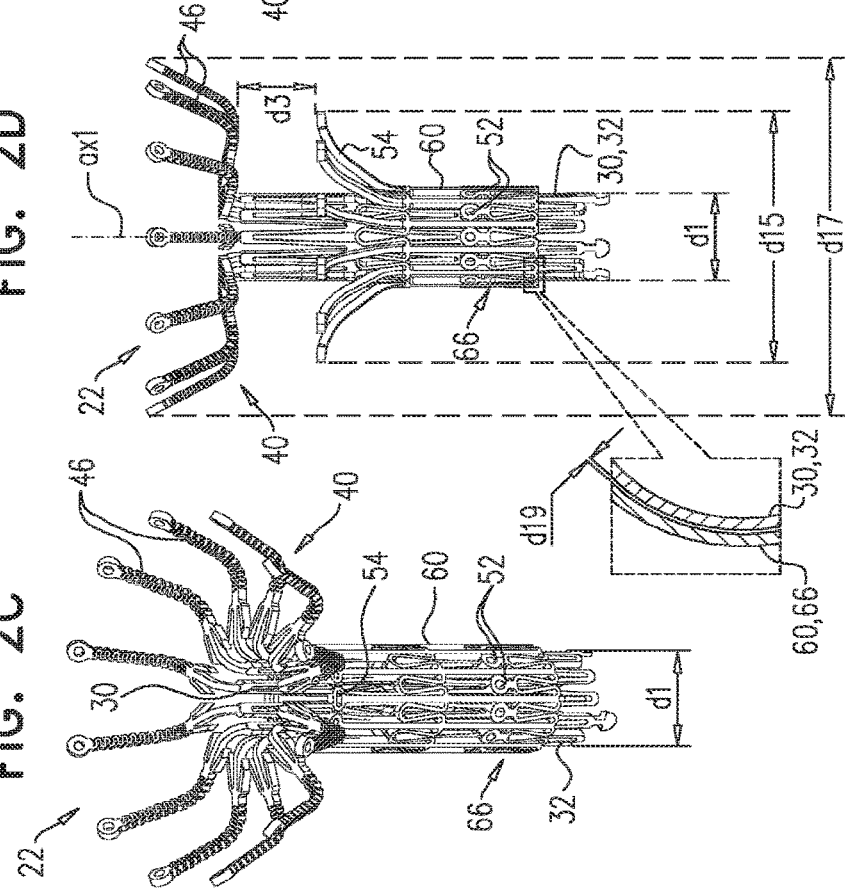

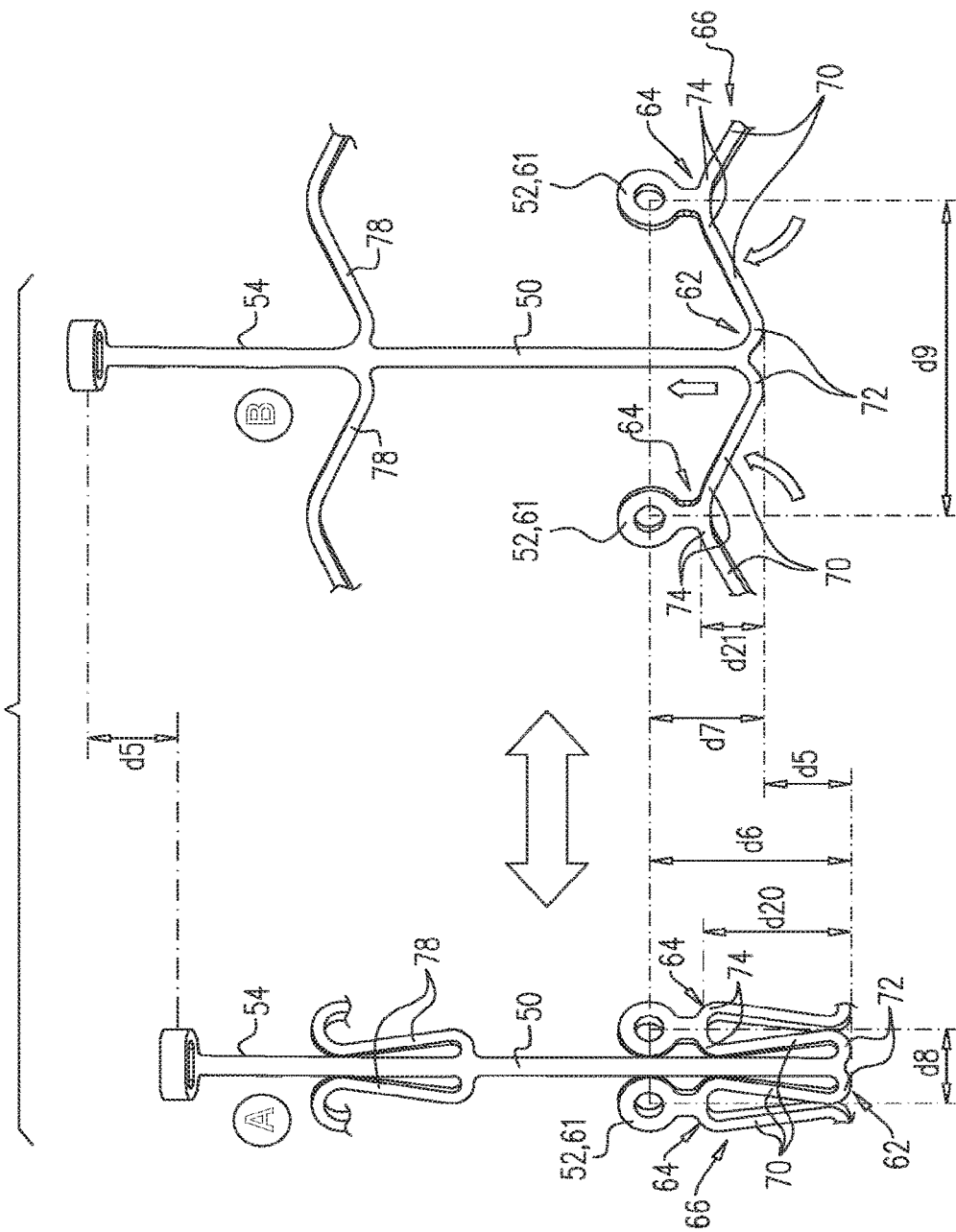

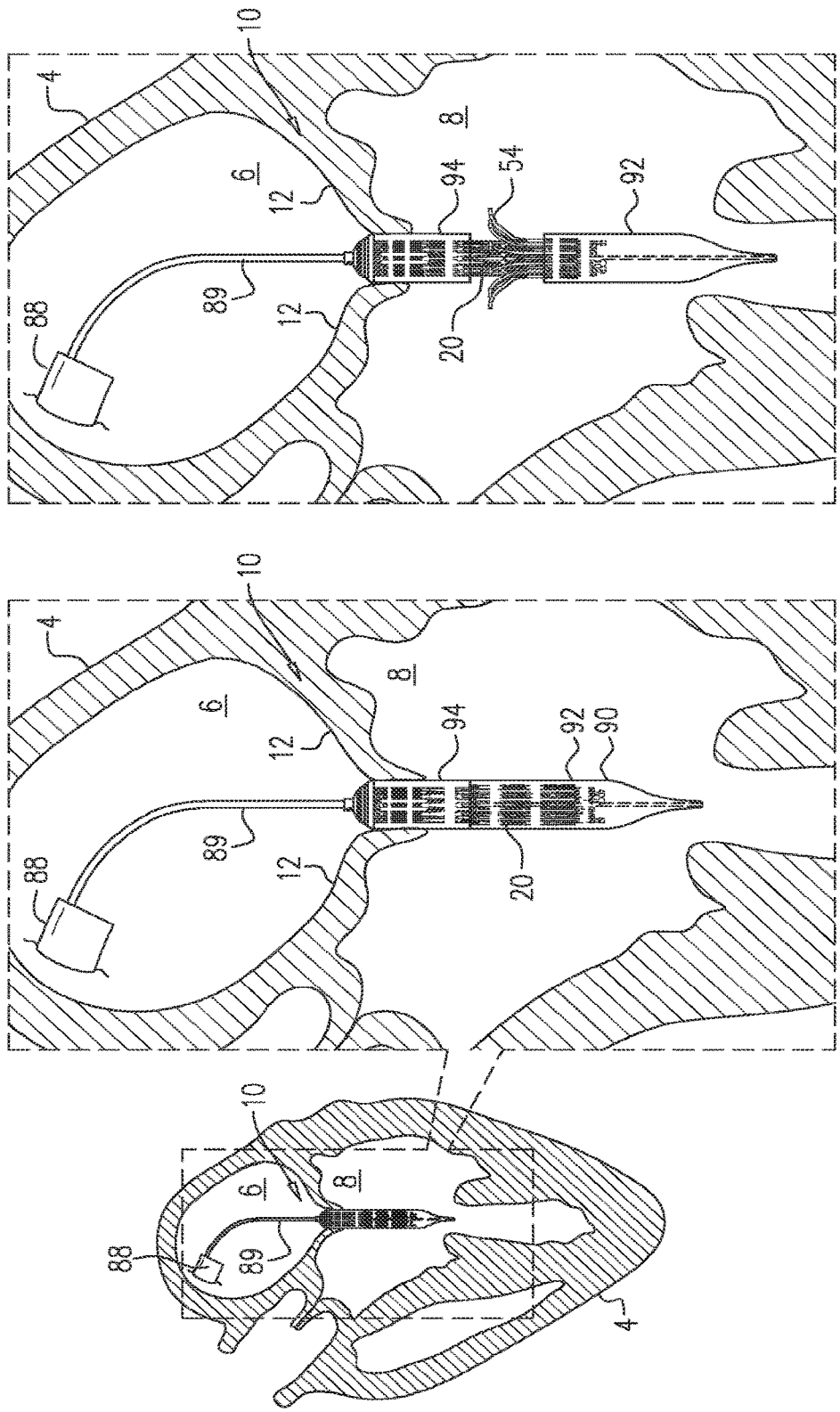

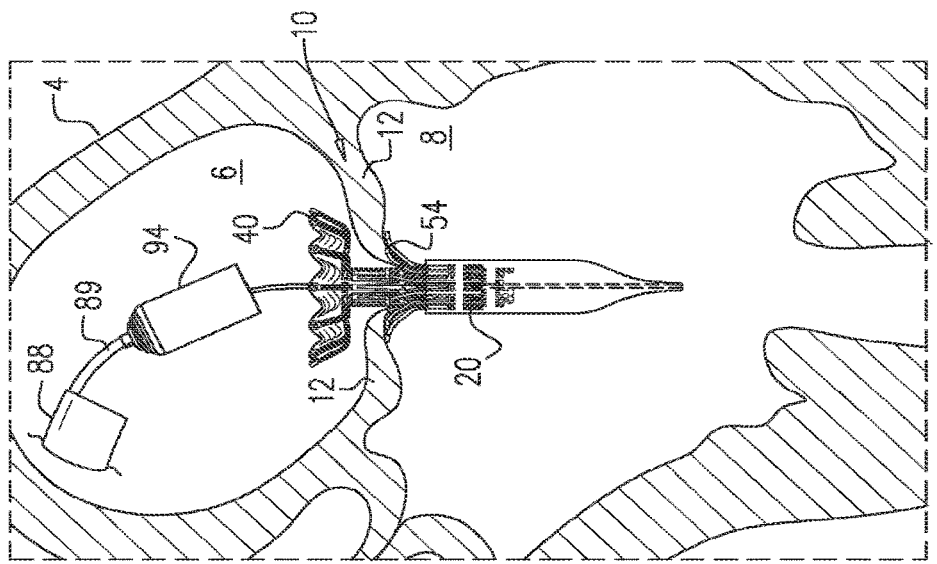
FIG. 4D
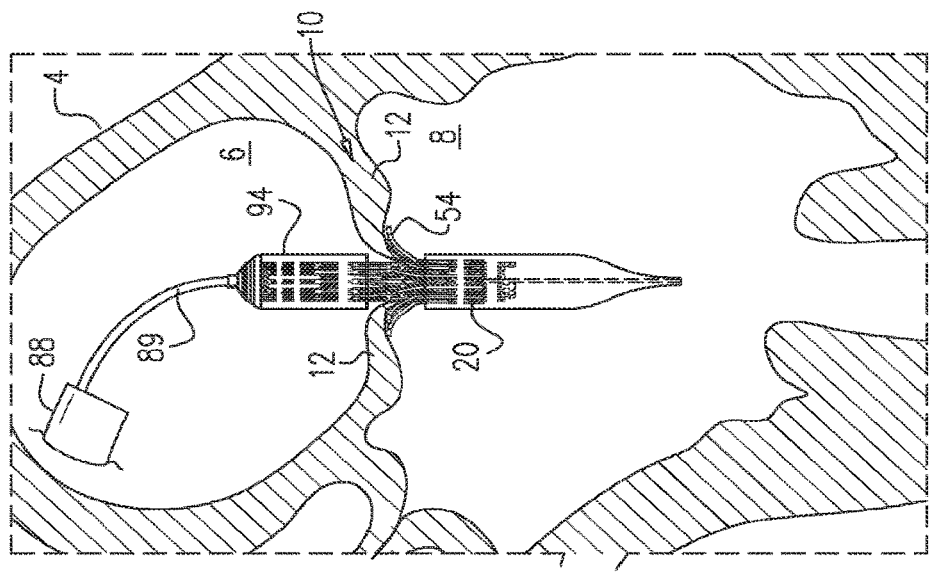
FIG. 4C
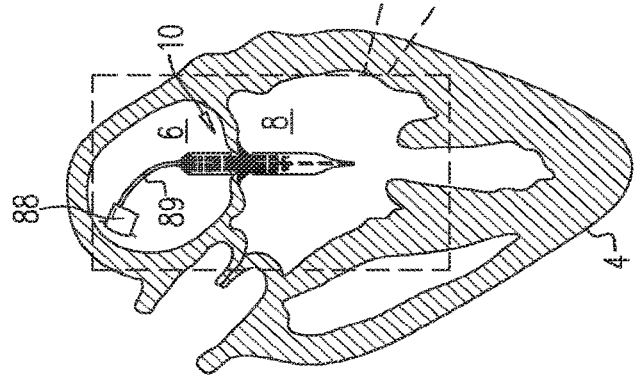

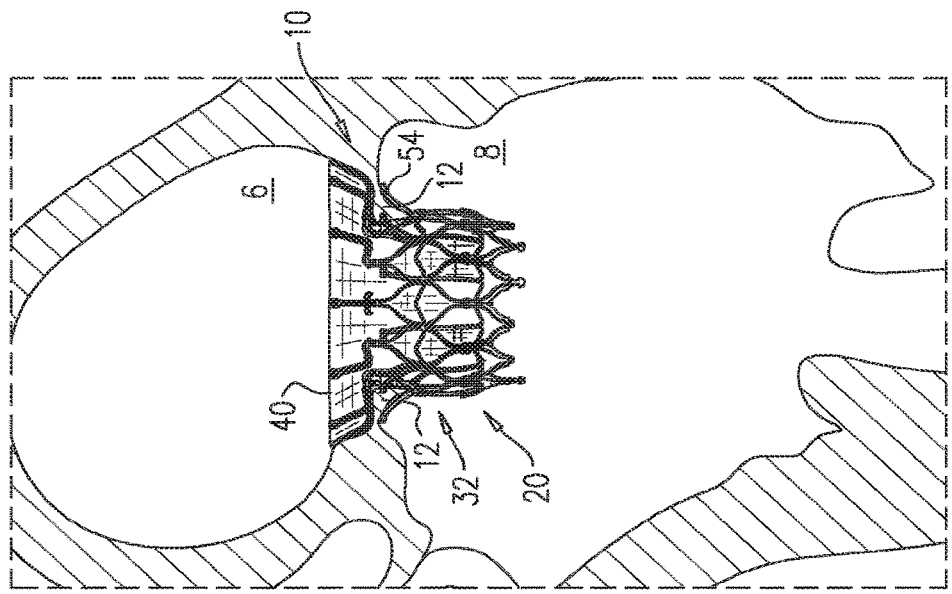
FIG. 4F
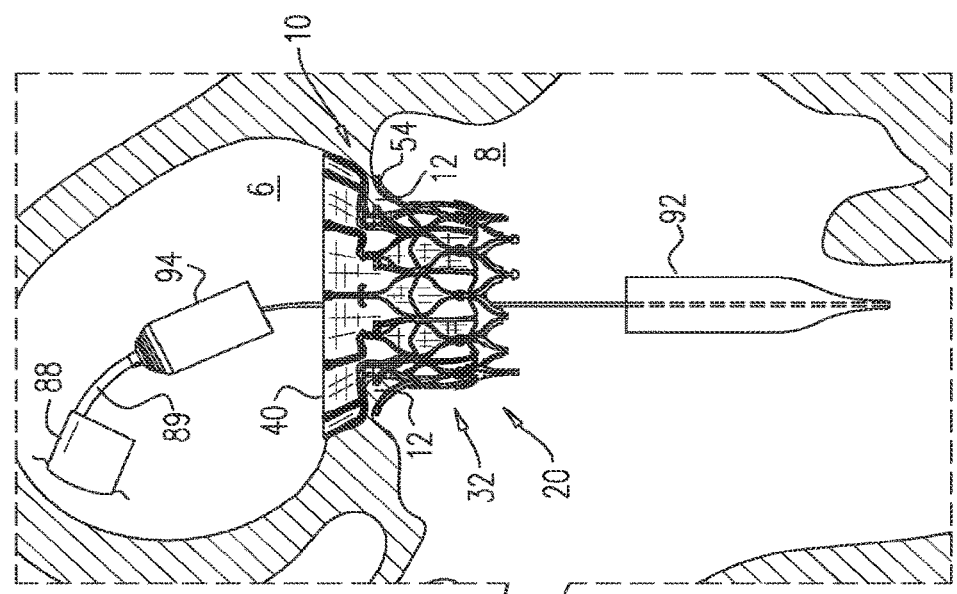
FIG. 4E
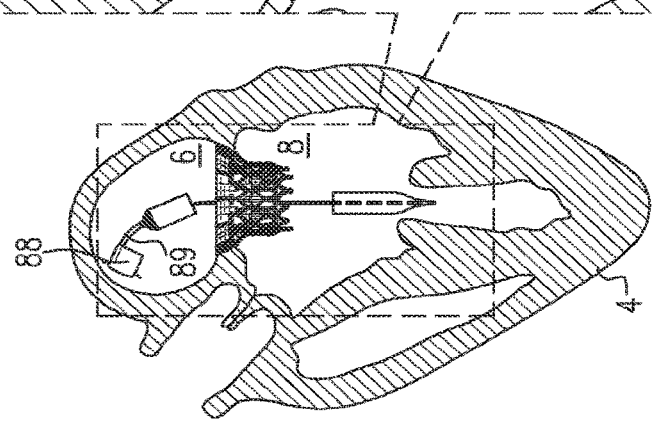

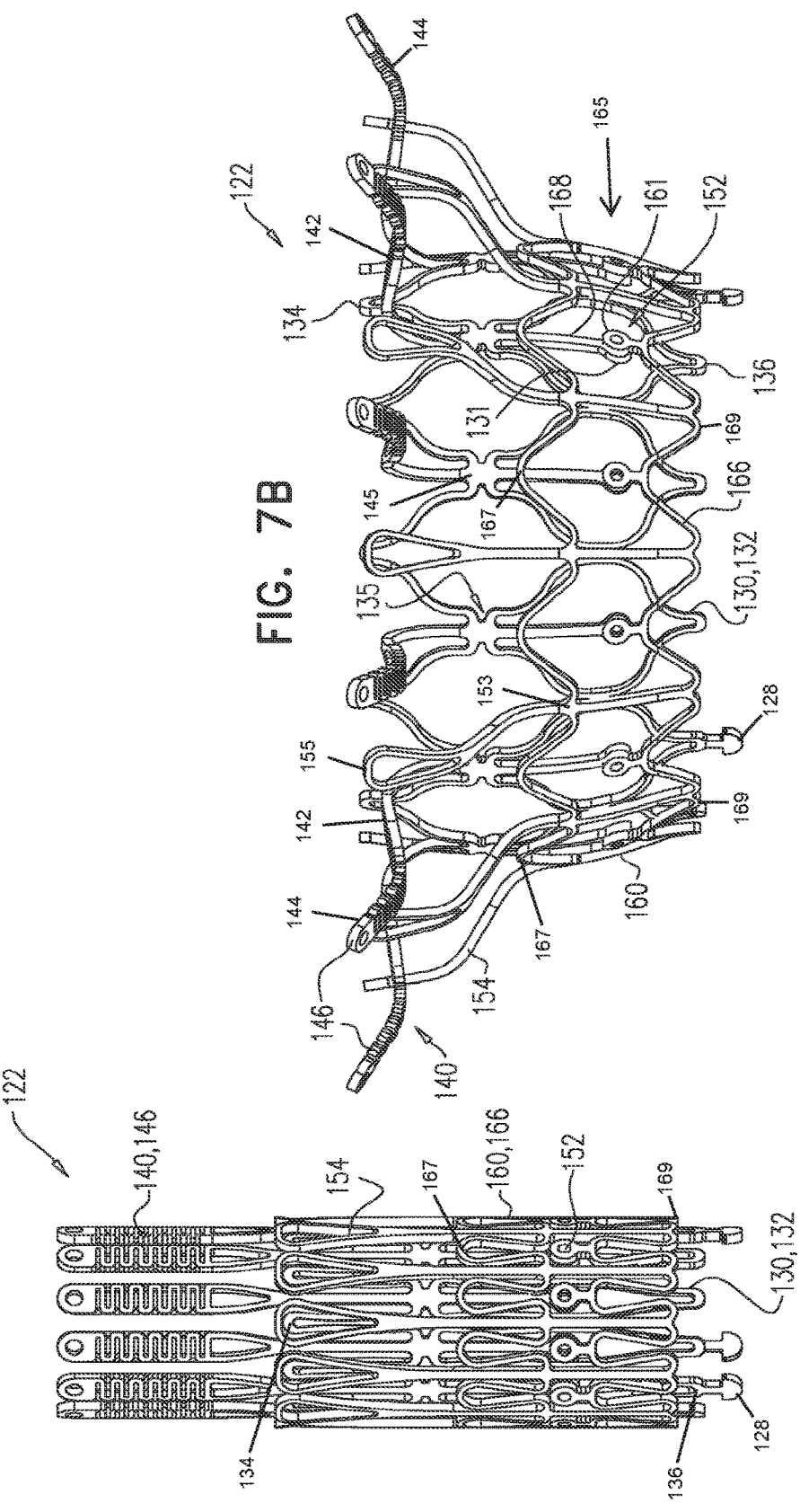

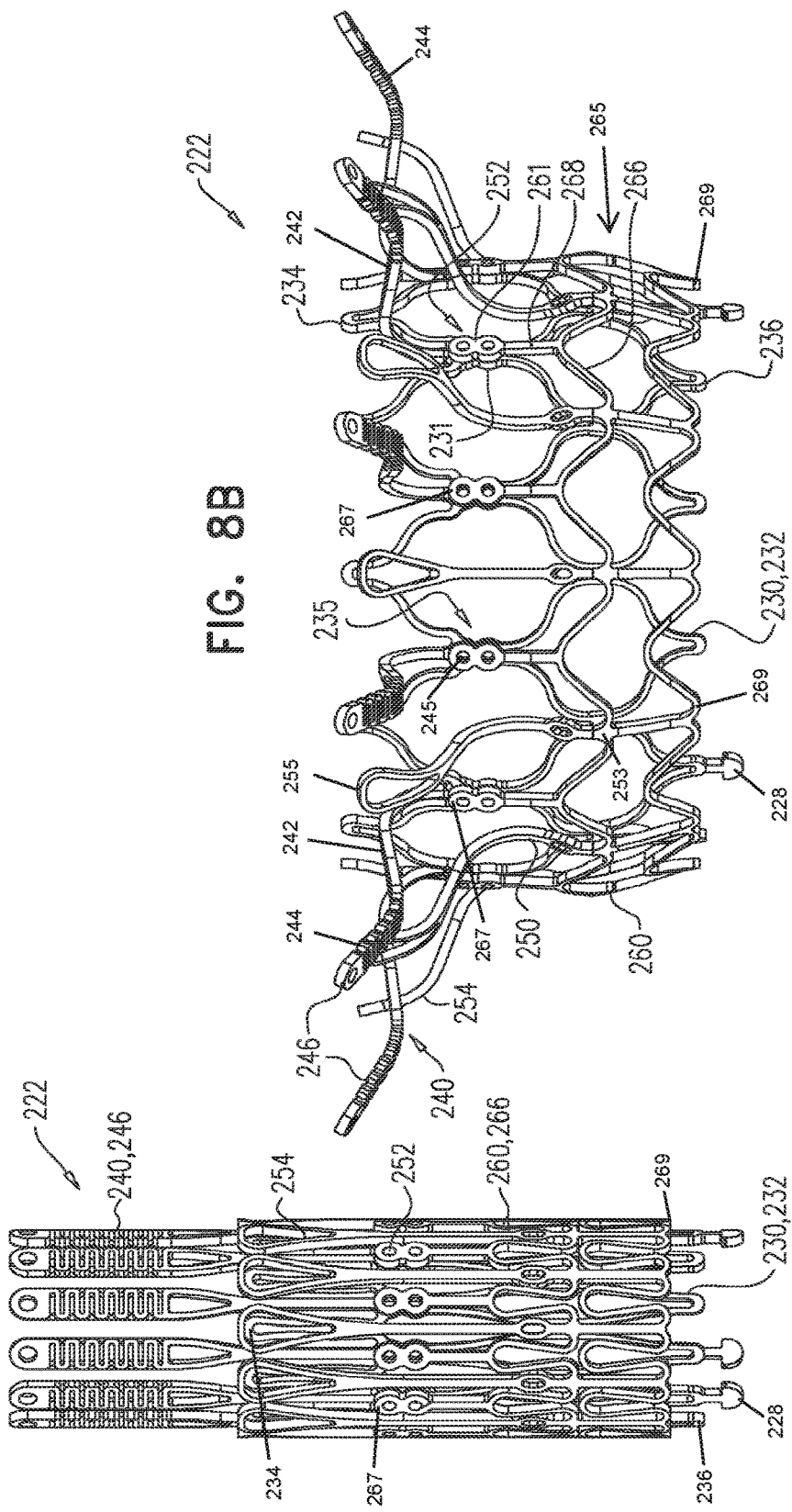

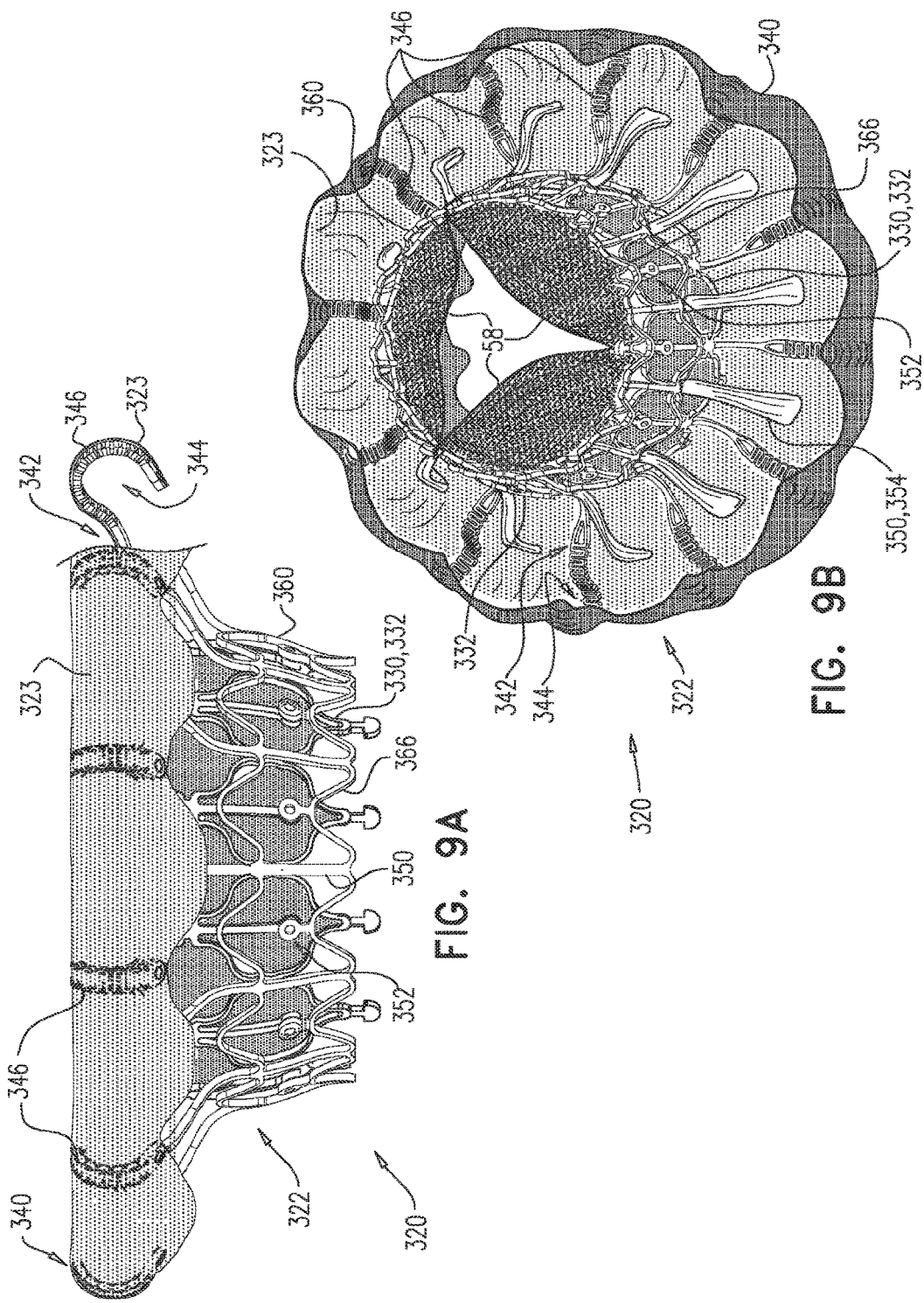

PROSTHETIC VALVE WITH ALIGNED INNER AND OUTER FRAMES

CROSS-REFERENCES TO RELATED APPLICATIONS

This application is a continuation of U.S. patent application Ser. No. 15/978,494, filed May 14, 2018, which is a continuation of U.S. patent application Ser. No. 15/541,783, filed Jul. 6, 2017, which issued as U.S. Pat. No. 9,974,651 on May 22, 2018 which is a U.S. national stage entry under 35 U.S.C. § 371 of International Application No. PCT/IL2016/050125, filed Feb. 3, 2016, which claims priority from U.S. Provisional Patent Application No. 62/112,343, filed Feb. 5, 2015, all of which are hereby incorporated by reference in their entirety.

FIELD OF THE INVENTION

Some embodiments of the present invention relate in general to valve replacement. More specifically, some embodiments of the present invention relate to prosthetic valves for replacement of a cardiac valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilatation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some embodiments of the present invention, an implant is provided having a tubular portion, an upstream support portion and one or more flanges. The implant is percutaneously deliverable to a native heart valve in a compressed state, and is expandable at the native valve. The implant and its delivery system facilitate causing the upstream support portion and the flanges to protrude radially outward from the tubular portion without expanding the tubular portion. Expansion of the tubular portion brings the upstream support portion and the flanges closer together, for securing the implant at the native valve by sandwiching tissue of the native valve between the upstream support portion and the flanges.

In accordance with an embodiment of the present invention, an apparatus is provided for use with a native valve that is disposed between an atrium and a ventricle of a heart of a subject, the apparatus including: a valve frame, including a tubular portion that circumscribes a longitudinal axis of the valve frame so as to define a lumen along the axis, the tubular portion defining a plurality of valve-frame coupling elements disposed circumferentially around the longitudinal axis; a plurality of prosthetic leaflets, coupled to the frame, disposed within the lumen, and arranged to provide unidirectional flow of blood from an upstream end of the lumen to a downstream end of the lumen; an outer frame: including a ring defined by a pattern of alternating peaks and troughs, the peaks being longitudinally closer to the upstream end than to the downstream end, and the troughs being longitudinally closer to the downstream end than to the upstream end, and the pattern of the ring having an amplitude longitudinally between the peaks and the troughs, including a plurality of legs, each of the legs coupled to the ring at a respective trough, and shaped to define a plurality of outer-frame coupling elements, each of the outer-frame coupling elements (i) coupled to the ring at a respective peak, and (ii) fixed with respect to a respective valve-frame coupling element, and: the tubular portion has (i) a compressed state in which the tubular portion has a compressed diameter, and (ii) an expanded state in which the tubular portion has an expanded diameter that is greater than the compressed diameter, and the fixation of the outer-frame coupling elements to the valve-frame coupling elements is such that compression of the tubular portion from the expanded state toward the compressed state such that the valve-frame coupling elements pull the outer-frame coupling elements radially inward: (i) reduces a circumferential distance between each of the outer-frame coupling elements and its adjacent outer-frame coupling elements, and (ii) increases the amplitude of the pattern of the ring.

In an embodiment, the ring circumscribes the tubular portion.

In an embodiment, the valve-frame coupling elements are disposed circumferentially around the longitudinal axis between the upstream end and the downstream end but not at the upstream end nor at the downstream end.

In an embodiment, the upstream support portion includes one or more fabric pockets disposed circumferentially, each pocket of the one or more pockets having an opening that faces a downstream direction.

In an embodiment, the outer frame is coupled to the valve frame only via the fixation of the outer-frame coupling elements to the respective valve-frame coupling elements.

In an embodiment, the apparatus further includes an upstream support portion that includes a plurality of arms that extend radially from the tubular portion, and the upstream support portion has (i) a constrained-arm state, and (ii) a released-arm state in which the arms extend radially outward from the tubular portion, each leg has a tissue-engaging flange that has (i) a constrained-flange state, and (ii) a released-flange state in which the flange extends radially outward from the tubular portion, and the apparatus has an intermediate state in which (i) the tubular portion is in its compressed state, (ii) the upstream support portion is in its released-arm state, and (iii) the legs are in their released-flange state.

In an embodiment, the apparatus includes an implant that includes the valve frame, the leaflets, and the outer frame, and the apparatus further includes a tool: including a delivery capsule dimensioned (i) to house and retain the implant in a compressed state of the implant in which (a) the tubular portion is in its compressed state, (b) the upstream support portion is in its constrained-arm state, and (c) the legs are in their constrained-flange state, and (ii) to be advanced percutaneously to the heart of the subject while the implant is housed and in its compressed state, and operable from outside the subject to: transition the implant from its compressed state into the intermediate state while retaining the tubular portion in its compressed state, and subsequently, expand the tubular portion toward its expanded state.

In an embodiment, the tool is operable from outside the subject to transition the implant from its compressed state into the intermediate state by (i) releasing the legs into their released-flange state, while retaining the tubular portion in its compressed state, and (ii) subsequently, releasing the upstream support portion into its released-arm state, while retaining the tubular portion in its compressed state.

In an embodiment, the tool is operable from outside the subject to transition the implant from its compressed state into the intermediate state by (i) releasing the upstream support portion into its released-arm state, while retaining the tubular portion in its compressed state, and (ii) subsequently, releasing the legs into their released-flange state, while retaining the tubular portion in its compressed state.

In an embodiment, the fixation of the outer-frame coupling elements to the valve-frame coupling elements is such that, when the apparatus is in its intermediate state, expansion of the tubular portion from its compressed state toward its expanded state moves the flanges longitudinally away from the valve-frame coupling elements.

In an embodiment, the fixation of the outer-frame coupling elements to the valve-frame coupling elements is such that, when the apparatus is in its intermediate state, expansion of the tubular portion from a compressed state toward an expanded state reduces the amplitude of the pattern of the ring and passes the flanges between the arms.

In an embodiment, the upstream support portion further includes a covering that covers the arms to form an annular shape in the released-arm state, and, when the apparatus is in its intermediate state, expansion of the tubular portion from its compressed state toward its expanded state presses the flanges onto the covering.

In an embodiment, in the compressed state of the tubular portion, a downstream end of each leg of the tubular portion is longitudinally closer than the valve-frame coupling elements to the downstream end, and the flange of each leg is disposed longitudinally closer than the valve-frame coupling elements to the upstream end.

In an embodiment, in the expanded state of the tubular portion, the downstream end of each leg is longitudinally closer than the valve-frame coupling elements to the downstream end, and the flange of each leg is disposed longitudinally closer than the valve-frame coupling elements to the upstream end.

In accordance with an embodiment of the present invention, an apparatus for use with a native valve of a heart of a subject is provided, the apparatus having an implant that includes: a valve frame that includes a tubular portion that circumscribes a longitudinal axis of the valve frame so as to define a lumen along the axis, the tubular portion having an upstream end, a downstream end, a longitudinal length therebetween, and a diameter transverse to the longitudinal axis; a valve member, coupled to the tubular portion, disposed within the lumen, and arranged to provide unidirectional upstream-to-downstream flow of blood through the lumen; an upstream support portion, coupled to the tubular portion; and an outer frame, coupled to the tubular portion, and including a tissue-engaging flange, and: the implant has a first state and a second state, in both the first state and the second state, (i) the upstream support portion extends radially outward from the tubular portion, and (ii) the tissue-engaging flange extends radially outward from the tubular portion, and the tubular portion, the upstream support portion, and the outer frame are arranged such that transitioning of the implant from the first state toward the second state: increases the diameter of the tubular portion by a diameter-increase amount, decreases the length of the tubular portion by a length-decrease amount, and moves the flange a longitudinal distance toward or toward-and-beyond the upstream support portion, the distance being greater than the length-decrease amount.

In an embodiment of the present invention, the tubular portion, the upstream support portion, and the outer frame may be arranged such that the longitudinal distance is more than 20 percent greater than the length-decrease amount.

In an embodiment, the tubular portion, the upstream support portion, and the outer frame may be arranged such that the longitudinal distance is more than 30 percent greater than the length-decrease amount.

In an embodiment, the tubular portion, the upstream support portion, and the outer frame may be arranged such that the longitudinal distance is more than 40 percent greater than the length-decrease amount.

In accordance with an embodiment of the present invention, an apparatus for use with a native valve that is disposed between an atrium and a ventricle of a heart of a subject is provided, the apparatus including: a valve frame, including a tubular portion that circumscribes a longitudinal axis of the valve frame so as to define a lumen along the axis; a plurality of prosthetic leaflets, coupled to the frame, disposed within the lumen, and arranged to provide unidirectional flow of blood from an upstream end of the lumen to a downstream end of the lumen; an outer frame, including: a ring defined by a pattern of alternating peaks and troughs: the peaks being longitudinally closer than the troughs to the upstream end, the peaks being fixed to respective sites of the tubular portion at respective coupling points disposed circumferentially around the longitudinal axis, and the pattern of the ring having an amplitude longitudinally between the peaks and the troughs; and a plurality of legs, each of the legs coupled to the ring at a respective trough, and: the tubular portion has (i) a compressed state in which the tubular portion has a compressed diameter, and (ii) an expanded state in which the tubular portion has an expanded diameter that is greater than the compressed diameter, and the fixation of the peaks to the respective sites of the tubular portion is such that compression of the tubular portion from the expanded state toward the compressed state such that the respective sites of the tubular portion pull the peaks radially inward via radially-inward tension on the coupling points: (i) reduces a circumferential distance between each of the coupling points and its adjacent coupling points, and (ii) increases the amplitude of the pattern of the ring.

In an embodiment, the outer frame may be coupled to the valve frame only via the fixation of the peaks to the respective sites of the tubular portion at the respective coupling points.

In accordance with an embodiment of the present invention, an apparatus for use with a native valve that is disposed between an atrium and a ventricle of a heart of a subject is provided, the apparatus including: a valve frame, including a tubular portion that circumscribes a longitudinal axis of the valve frame so as to define a lumen along the axis, the valve frame defining a plurality of valve-frame coupling elements disposed circumferentially around the longitudinal axis; a plurality of prosthetic leaflets, coupled to the frame, disposed within the lumen, and arranged to provide unidirectional flow of blood from an upstream end of the lumen to a downstream end of the lumen; an outer frame: including a ring defined by a pattern of alternating peaks and troughs, the peaks being longitudinally closer to the upstream end than to the downstream end, and the troughs being longitudinally closer to the downstream end than to the upstream end, and the pattern of the ring having an amplitude longitudinally between the peaks and the troughs, including a plurality of legs, each of the legs coupled to the ring at a respective trough, and shaped to define a plurality of outer-frame coupling elements, each of the outer-frame coupling elements (i) coupled to the ring at a respective peak, and (ii) fixed with respect to a respective valve-frame coupling element, and: the tubular portion has (i) a compressed state in which the tubular portion has a compressed diameter, and (ii) an expanded state in which the tubular portion has an expanded diameter that is greater than the compressed diameter, and the fixation of the outer-frame coupling elements with respect to the valve-frame coupling elements is such that compression of the tubular portion from the expanded state toward the compressed state (i) pulls the outer-frame coupling elements radially inward via radially-inward pulling of the valve-frame coupling elements on the outer-frame coupling elements, (ii) reduces a circumferential distance between each of the outer-frame coupling elements and its adjacent outer-frame coupling elements, and (iii) increases the amplitude of the pattern of the ring, without increasing a radial gap between the valve frame and the ring by more than 1.5 mm.

In an embodiment, the outer frame may be coupled to the valve frame only via the fixation of the outer-frame coupling elements to the respective valve-frame coupling elements.

There is further provided, in accordance with an embodiment of the present invention, an apparatus for use with a native valve that is disposed between an atrium and a ventricle of a heart of a subject is provided, the apparatus including: a valve frame, including a tubular portion that circumscribes a longitudinal axis of the valve frame so as to define a lumen along the axis; a plurality of prosthetic leaflets, coupled to the frame, disposed within the lumen, and arranged to provide unidirectional flow of blood from an upstream end of the lumen to a downstream end of the lumen; an outer frame, including: a ring defined by a pattern of alternating peaks and troughs: the peaks being longitudinally closer than the troughs to the upstream end, the peaks being fixed to respective sites of the tubular portion at respective coupling points disposed circumferentially around the longitudinal axis, and the pattern of the ring having an amplitude longitudinally between the peaks and the troughs; and a plurality of legs, each of the legs coupled to the ring at a respective trough, and: the tubular portion has (i) a compressed state in which the tubular portion has a compressed diameter, and (ii) an expanded state in which the tubular portion has an expanded diameter that is greater than the compressed diameter, and the fixation of the peaks to the respective sites of the tubular portion is such that compression of the tubular portion from the expanded state toward the compressed state (i) pulls the peaks radially inward via radially-inward pulling of the respective sites of the tubular portion on the peaks, (ii) reduces a circumferential distance between each of the coupling points and its adjacent coupling points, and (iii) increases the amplitude of the pattern of the ring, without increasing a radial gap between the valve frame and the ring by more than 1.5 mm.

In an embodiment, the outer frame may be coupled to the valve frame only via the fixation of the peaks to the respective sites of the tubular portion at the respective coupling points.

In accordance with an embodiment of the present invention, an apparatus for use with a native valve disposed between an atrium and a ventricle of a heart of a subject is provided, the apparatus including: a valve frame, including a tubular portion that circumscribes a longitudinal axis of the valve frame so as to define a lumen along the axis, the tubular portion having an upstream end, a downstream end, and defining a plurality of valve-frame coupling elements disposed circumferentially around the longitudinal axis between the upstream end and the downstream end but not at the upstream end nor at the downstream end; a plurality of prosthetic leaflets, disposed within the lumen, and arranged to provide unidirectional flow of blood through the lumen; an outer frame: including a ring defined by a pattern of alternating peaks and troughs, the peaks being longitudinally closer to the upstream end than to the downstream end, and the troughs being longitudinally closer to the downstream end than to the upstream end, including a plurality of legs, each of the legs coupled to the ring at a respective trough, and shaped to define a plurality of outer-frame coupling elements, each of the outer-frame coupling elements (i) coupled to the ring at a respective peak, and (ii) fixed with respect to a respective valve-frame coupling element at a respective coupling point, and: the tubular portion has (i) a compressed state in which the tubular portion has a compressed diameter, and (ii) an expanded state in which the tubular portion has an expanded diameter that is greater than the compressed diameter, and expansion of the tubular portion from the compressed state toward the expanded state (i) increases a circumferential distance between each of the outer-frame coupling elements and its adjacent outer-frame coupling elements, and (ii) moves the plurality of legs in a longitudinally upstream direction with respect to the tubular portion.

In an embodiment, the outer frame may be coupled to the valve frame only via the fixation of the outer-frame coupling elements to the respective valve-frame coupling elements.

In accordance with an embodiment of the present invention, an apparatus for use with a native valve disposed between an atrium and a ventricle of a heart of a subject is provided, the apparatus including: a valve frame, including a tubular portion that circumscribes a longitudinal axis of the valve frame so as to define a lumen along the axis, the tubular portion having an upstream end and a downstream end; a plurality of prosthetic leaflets, disposed within the lumen, and arranged to provide unidirectional flow of blood through the lumen; an outer frame, including: a ring defined by a pattern of alternating peaks and troughs: the peaks being longitudinally closer than the troughs to the upstream end, the peaks being fixed to respective sites of the tubular portion at respective coupling points disposed circumferentially around the longitudinal axis between the upstream end and the downstream end but not at the upstream end nor the downstream end; and a plurality of legs, each of the legs coupled to the ring at a respective trough, and: the tubular portion has (i) a compressed state in which the tubular portion has a compressed diameter, and (ii) an expanded state in which the tubular portion has an expanded diameter that is greater than the compressed diameter, and expansion of the tubular portion from the compressed state toward the expanded state (i) increases a circumferential distance between each of the coupling points and its adjacent coupling points, and (ii) moves the plurality of legs in a longitudinally upstream direction with respect to the tubular portion.

In an embodiment, the outer frame may be coupled to the valve frame only via the fixation of the peaks to the respective sites of the tubular portion at the respective coupling points.

In accordance with an embodiment of the present invention, an apparatus for use with a native valve of a heart of a subject is provided, the apparatus including: a frame assembly, having an upstream end and a downstream end, and a central longitudinal axis therebetween, and including: a valve frame, including: a tubular portion having an upstream end and a downstream end, and shaped to define a lumen therebetween, and an upstream support portion, extending from the upstream end of the tubular portion; and at least one leg, coupled to the valve frame at a coupling point, and having a tissue-engaging flange; and a valve member disposed within the lumen, and configured to facilitate one-way liquid flow through the lumen from the upstream end of the tubular portion to the downstream end of the tubular portion, and the frame assembly: has a compressed state, for percutaneous delivery to the heart, in which the tubular portion has a compressed diameter, is biased to assume an expanded state in which the tubular portion has an expanded diameter that is greater than the compressed diameter, and is configured such that increasing the diameter of the tubular portion toward the expanded diameter causes longitudinal movement: of the upstream support portion toward the coupling point, and of the tissue-engaging flange away from the coupling point.

In an embodiment: the apparatus includes an implant that includes the frame assembly and the valve member, and the apparatus further includes a tool: including a delivery capsule dimensioned (i) to house and retain the implant in the compressed state, and (ii) to be advanced percutaneously to the heart of the subject while the implant is housed and in the compressed state, and operable from outside the subject to facilitate an increase of the diameter of the tubular portion from the compressed diameter toward the expanded diameter such that the increase of the diameter actuates longitudinal movement: of the upstream support portion toward the coupling point, and of the tissue-engaging flange away from the coupling point.

In an embodiment, the frame assembly may be configured such that increasing the diameter of the tubular portion by expanding the frame assembly toward the expanded state causes longitudinal movement of the upstream end of the tubular portion toward the coupling point.

In an embodiment, the coupling point is disposed closer to the downstream end of the frame assembly than are either the tissue-engaging flange or the upstream support portion.

In an embodiment, in the expanded state of the frame assembly, the leg extends away from the central longitudinal axis.

In an embodiment, the expanded state of the frame assembly may be a fully-expanded state of the frame assembly, the leg is expandable into an expanded state of the leg, independently of increasing the diameter of the tubular portion, and in the expanded state of the leg, the leg extends away from the central longitudinal axis.

In an embodiment, in the expanded state of the frame assembly, the leg extends away from the central longitudinal axis, and in the compressed state of the frame assembly, the leg is generally parallel with the central longitudinal axis.

In an embodiment, the frame assembly may be configured such that the longitudinal movement of the tissue-engaging flange away from the coupling point is a translational movement of the tissue-engaging flange that does not include rotation of the tissue-engaging flange.

In an embodiment, the frame assembly may be configured such that increasing the diameter of the tubular portion by expanding the frame assembly toward the expanded state causes 1-20 mm of longitudinal movement of the tissue-engaging flange away from the coupling point.

In an embodiment, the frame assembly may be configured such that increasing the diameter of the tubular portion by expanding the frame assembly toward the expanded state causes 1-20 mm of longitudinal movement of the upstream support portion toward the coupling point.

In an embodiment, the frame assembly may be configured such that increasing the diameter of the tubular portion by expanding the frame assembly toward the expanded state reduces a distance between the upstream support portion and the tissue-engaging flange by 5-30 mm.

In an embodiment, the frame assembly may be configured such that increasing the diameter of the tubular portion by expanding the frame assembly toward the expanded state moves the tissue-engaging flange longitudinally past the upstream support portion.

In an embodiment, the tubular portion may be defined by a plurality of cells of the valve frame, and increasing the diameter of the tubular portion by expanding the frame assembly toward the expanded state: includes (i) increasing a width, orthogonal to the longitudinal axis of the frame assembly, of each cell, and (ii) reducing a height, parallel with the longitudinal axis of the frame assembly, of each cell, and causes longitudinal movement of the upstream support portion toward the coupling point by reducing a height, parallel with the longitudinal axis of the frame assembly, of the tubular portion, by reducing the height of each cell.

In an embodiment, the leg is disposed on an outside of the tubular portion.

In an embodiment, the at least one leg includes a plurality of legs, the coupling point includes a plurality of coupling points, and the frame assembly includes a leg frame that circumscribes the tubular portion, includes the plurality of legs, and is coupled to the valve frame at the plurality of coupling points, such that the plurality of legs is distributed circumferentially around the tubular portion.

In an embodiment, the plurality of coupling points is disposed circumferentially around the frame assembly on a transverse plane that is orthogonal to the longitudinal axis of the frame assembly.

In an embodiment, the plurality of legs may be coupled to the valve frame via a plurality of struts, each strut having a first end that is coupled to a leg of the plurality of legs, and a second end that is coupled to a coupling point of the plurality of coupling points, in the compressed state of the frame assembly, being disposed at a first angle in which the first end is disposed closer to the downstream end of the frame assembly than is the second end, and being deflectable with respect to the coupling point of the plurality of coupling points, such that increasing the diameter of the tubular portion by expanding the frame assembly toward the expanded state causes the strut to deflect to a second angle in which the first end is disposed further from the downstream end of the frame assembly than is the first end in the compressed state of the frame assembly.

In an embodiment, the leg frame may be structured such that each leg of the plurality of legs is coupled to two struts of the plurality of struts, and two struts of the plurality of struts are coupled to each coupling point of the plurality of coupling points.

In an embodiment, the leg may be coupled to the valve frame via a strut, the strut having a first end that is coupled to the leg, and a second end that is coupled to the coupling point, in the compressed state of the frame assembly, being disposed at a first angle in which the first end is disposed closer to the downstream end of the frame assembly than is the second end, and being deflectable with respect to the coupling point, such that increasing the diameter of the tubular portion by expanding the frame assembly toward the expanded state causes the strut to deflect to a second angle in which the first end is disposed further from the downstream end of the frame assembly than is the first end in the compressed state of the frame assembly.

In an embodiment, the at least one leg includes at least a first leg and a second leg.

In an embodiment, the first leg and the second leg are both coupled to the valve frame at the coupling point.

In an embodiment, the first leg may be coupled to the coupling point via a respective first strut, and the second leg is coupled to the coupling point via a respective second strut.

In an embodiment, the first and second legs, the first and second struts, and the coupling point are arranged such that, in the expanded state of the frame assembly: the coupling point is disposed, circumferentially with respect to the tubular portion, between the first strut and the second strut, the first strut is disposed, circumferentially with respect to the tubular portion, between the coupling point and the first leg, and the second strut is disposed, circumferentially with respect to the tubular portion, between the coupling point and the second leg.

In an embodiment, the coupling point includes at least a first coupling point and a second coupling point.

In an embodiment, the leg is coupled to the valve frame at the first coupling point and at the second coupling point.

In an embodiment, the leg may be coupled to the first coupling point via a respective first strut, and to the second coupling point via a respective second strut.

In an embodiment, the first and second legs, the first and second struts, and the coupling point are arranged such that, in the expanded state of the frame assembly: the leg is disposed, circumferentially with respect to the tubular portion, between the first strut and the second strut, the first strut is disposed, circumferentially with respect to the tubular portion, between the leg and the first coupling point, and the second strut is disposed, circumferentially with respect to the tubular portion, between the leg and the second coupling point.

In an embodiment, in the expanded state of the frame assembly, the upstream support portion extends radially outward from the tubular portion.

In an embodiment, the expanded state of the frame assembly is a fully-expanded state of the frame assembly, the upstream support portion is expandable into an expanded state of the upstream support portion, independently of increasing the diameter of the tubular portion, and in the expanded state of the upstream support portion, the upstream support portion extends radially outward from the tubular portion.

In an embodiment, in the compressed state of the frame assembly, the upstream support portion is generally tubular, collinear with the tubular portion, and disposed around the central longitudinal axis.

In an embodiment, in the expanded state of the frame assembly, an inner region of the upstream support portion extends radially outward from the tubular portion at a first angle with respect to the tubular portion, and an outer region of the upstream support portion extends, from the inner region of the upstream support portion, further radially outward from the tubular portion at a second angle with respect to the tubular portion, the second angle being smaller than the first angle.

In accordance with an embodiment of the present invention, an apparatus for use with a native valve of a heart of a subject is provided, the apparatus including a frame assembly, having an upstream end and a downstream end, and a central longitudinal axis therebetween, and including: a valve frame, including: a tubular portion having an upstream end and a downstream end, and shaped to define a lumen therebetween, and an upstream support portion, extending from the upstream end of the tubular portion; and at least one leg, coupled to the valve frame at a coupling point, and having a tissue-engaging flange; and a valve member disposed within the lumen, and configured to facilitate one-way liquid flow through the lumen from the upstream end of the tubular portion to the downstream end of the tubular portion, and the frame assembly: has a compressed state, for percutaneous delivery to the heart, in which the tubular portion has a compressed diameter, is biased to assume an expanded state in which the tubular portion has an expanded diameter that is greater than the compressed diameter, and is configured such that reducing the diameter of the tubular portion toward the compressed diameter causes longitudinal movement of the upstream support portion away from the coupling point, and of the tissue-engaging flange toward the coupling point.

In accordance with an embodiment of the present invention, an apparatus for use with a native valve of a heart of a subject is provided, the apparatus including a frame assembly, having an upstream end and a downstream end, and a central longitudinal axis therebetween, including: a valve frame, including: a tubular portion having an upstream end and a downstream end, and shaped to define a lumen therebetween, and an upstream support portion, extending from the upstream end of the tubular portion; and at least one leg, coupled to the valve frame at a coupling point, and having a tissue-engaging flange; and a valve member disposed within the lumen, and configured to facilitate one-way liquid flow through the lumen from the upstream end of the tubular portion to the downstream end of the tubular portion, and the frame assembly: has a compressed state, for percutaneous delivery to the heart, is intracorporeally expandable into an expanded state in which a diameter of the tubular portion is greater than in the compressed state, and is configured such that increasing the diameter of the tubular portion by expanding the frame assembly toward the expanded state causes longitudinal movement of the tissue-engaging flange away from the coupling point.

In accordance with an embodiment of the present invention, an apparatus for use with a native valve of a heart of a subject is provided, the apparatus including a frame assembly, having an upstream end and a downstream end, and a central longitudinal axis therebetween, and including: an inner frame including an inner-frame tubular portion that circumscribes the central longitudinal axis, has an upstream end and a downstream end, and defines a channel therebetween, the inner frame defining a plurality of inner-frame couplings disposed circumferentially at a longitudinal location of the inner frame, an outer frame including an outer-frame tubular portion that coaxially circumscribes at least a portion of the inner-frame tubular portion, the outer frame defining a plurality of outer-frame couplings disposed circumferentially at a longitudinal location of the outer frame, and a plurality of connectors, each connector connecting a respective inner-frame coupling to a respective outer-frame coupling; a liner, disposed over at least part of the inner-frame tubular portion; and a plurality of prosthetic leaflets, coupled to the inner-frame tubular portion and disposed within the channel, and: the frame assembly: (i) is compressible by a radially-compressive force into a compressed state in which the inner frame is in a compressed state thereof and the outer frame is in a compressed state thereof, (ii) is configured, upon removal of the radially-compressive force, to automatically expand into an expanded state thereof in which the inner frame is in an expanded state thereof and the outer frame is in an expanded state thereof, in the expanded state of the frame assembly, the prosthetic leaflets are configured to facilitate one-way fluid flow, in a downstream direction, through the channel, and the connection of the inner-frame couplings to the respective outer-frame couplings is such that expansion of the frame assembly from the compressed state to the expanded state causes the inner-frame tubular portion to slide longitudinally in a downstream direction with respect to the outer-frame tubular portion.

In accordance with an embodiment of the present invention, an apparatus for use with a native valve disposed between an atrium and a ventricle of a heart of a subject is provided, the apparatus including: a tubular portion, having an upstream portion that includes an upstream end, and a downstream portion that includes a downstream end, and shaped to define a lumen between the upstream portion and the downstream portion; a plurality of prosthetic leaflets, disposed within the lumen, and arranged to provide unidirectional flow of blood from the upstream portion to the downstream portion; an annular upstream support portion: having an inner portion that extends radially outward from the upstream portion, and including one or more fabric pockets disposed circumferentially around the inner portion, each pocket of the one or more pockets having an opening that faces a downstream direction.

In an embodiment, the upstream support portion includes (i) a plurality of arms that extend radially outward from the tubular portion, and (ii) a covering, disposed over the plurality of arms, each arm has (i) a radially-inner part at the inner portion of the upstream support portion, and (ii) a radially-outer part at the outer portion of the upstream support portion, at the inner portion of the upstream support portion, the covering is closely-fitted between the radially-inner parts of the arms, and at the outer portion of the upstream support portion, the pockets are formed by the covering being loosely-fitted between the radially-outer parts of the arms.

In an embodiment, the upstream support portion includes (i) a plurality of arms that extend radially outward from the tubular portion, and (ii) a covering, disposed over the plurality of arms, each arm has (i) a radially-inner part at the inner portion of the upstream support portion, and (ii) a radially-outer part at the outer portion of the upstream support portion, the radially-outer part being more flexible than the radially-inner part.

In an embodiment, the upstream support portion includes (i) a plurality of arms that extend radially outward from the tubular portion, and (ii) a covering, disposed over the plurality of arms, each arm has (i) a radially-inner part at the inner portion of the upstream support portion, and (ii) a radially-outer part at the outer portion of the upstream support portion, at the outer portion of the upstream support portion, the pockets are formed by each arm curving to form a hook shape.

In an embodiment, each pocket may be shaped and arranged to billow in response to perivalvular flow of blood in an upstream direction.

In an embodiment, the apparatus may be configured to be transluminally delivered to the heart and implanted at the native valve by expansion of the apparatus, such that the upstream support portion is disposed in the atrium and the tubular portion extends from the upstream support portion into the ventricle, and each pocket is shaped and arranged such that perivalvular flow of blood in an upstream direction presses the pocket against tissue of the atrium.

In accordance with an embodiment of the present invention, an apparatus is provided including a plurality of prosthetic valve leaflets; and a frame assembly, including: a tubular portion defined by a repeating pattern of cells, the tubular portion extending circumferentially around a longitudinal axis so as to define a longitudinal lumen, the prosthetic valve leaflets coupled to the inner frame and disposed within the lumen; an outer frame, including a plurality of legs, distributed circumferentially around the tubular portion, each leg having a tissue-engaging flange; an upstream support portion that includes a plurality of arms that extend radially outward from the tubular portion; and a plurality of appendages, each having a first end that defines a coupling element via which the tubular portion is coupled to the outer frame, and a second end; and the frame assembly defines a plurality of hubs, distributed circumferentially around the longitudinal axis on a plane that is transverse to the longitudinal axis, each hub defined by convergence and connection of, (i) two adjacent cells of the tubular portion, (ii) an arm of the plurality of arms, and (iii) an appendage of the plurality of appendages.

In an embodiment, each hub has six radiating spokes, two of the six spokes being part of a first cell of the two adjacent cells, two of the six spokes being part of a second cell of the two adjacent cells, one of the six spokes being the arm, and one of the six spokes being the second end of the appendage.

In an embodiment, the appendages are in-plane with the tubular portion.

In an embodiment, the appendages are in-plane with the outer frame.

In accordance with an embodiment of the present invention, a method for use with a native valve of a heart of a subject is provided, the method including percutaneously advancing to heart, an implant: including a valve frame, a valve member disposed within a lumen defined by the valve frame, and at least one leg, coupled to the valve frame at a coupling point, and having an upstream end, a downstream end, and a central longitudinal axis therebetween; positioning the implant within the heart such that a tissue-engaging flange of the leg is disposed downstream of the valve, and thereafter causing the flange to protrude radially outward from the axis; subsequently, while an upstream support portion of the valve frame is disposed upstream of the valve, causing the upstream support portion to protrude radially outward from the axis, such that tissue of the valve is disposed between the upstream support portion and the flange; and subsequently, sandwiching the tissue between the upstream support portion and the flange by reducing a distance between the upstream support portion and the flange by causing longitudinal movement (i) of the upstream support portion toward the coupling point, and (ii) of the tissue-engaging flange away from the coupling point.

In an embodiment, causing the longitudinal movement (i) of the upstream support portion toward the coupling point, and (ii) of the tissue-engaging flange away from the coupling point, includes causing the longitudinal movement by increasing a diameter of the lumen.

In accordance with an embodiment of the present invention, a method for use with a native valve of a heart of a subject is provided, the method including percutaneously advancing to heart, an implant: including a valve frame, a valve member disposed within a lumen defined by the valve frame, and at least one leg, coupled to the valve frame at a coupling point, and having an upstream end, a downstream end, and a central longitudinal axis therebetween; positioning the implant within the heart such that an upstream support portion of the valve frame is disposed upstream of the valve, and thereafter causing the upstream support portion to protrude radially outward from the axis; subsequently, while a tissue-engaging flange of the leg is disposed downstream of the valve, causing the tissue-engaging flange to protrude radially outward from the axis, such that tissue of the valve is disposed between the upstream support portion and the flange; and subsequently, sandwiching the tissue between the upstream support portion and the flange by reducing a distance between the upstream support portion and the flange by causing longitudinal movement (i) of the upstream support portion toward the coupling point, and (ii) of the tissue-engaging flange away from the coupling point.

In an embodiment, causing the longitudinal movement (i) of the upstream support portion toward the coupling point, and (ii) of the tissue-engaging flange away from the coupling point, includes causing the longitudinal movement by increasing a diameter of the lumen.

In accordance with an embodiment of the present invention, a method for use with a native valve of a heart of a subject is provided, the method including: percutaneously advancing an implant to the heart, the implant having an upstream end, a downstream end, and a central longitudinal axis therebetween, and including a tubular portion, an upstream support portion, and a plurality of tissue-engaging flanges; positioning the implant within the heart such that the upstream support portion is disposed upstream of the valve, positioning the implant within the heart such that the tissue-engaging flanges are disposed downstream of the valve, without increasing a diameter of the tubular portion: causing the upstream support portion to extend radially outward from the axis so as to have a first support-portion span, and causing the flanges to extend radially outward from the axis so as to have a first flange span; and subsequently, causing the upstream support portion and the flanges move toward each other by at least 5 mm by increasing a diameter of the tubular portion such that: the upstream support portion extends radially outward so as to have a second support-portion span, the first support-portion span being at least 40 percent as great as the second support-portion span, and the flanges extend radially outward so as to have a second flange span, the first flange span being at least 30 percent as great as the second flange span.

There is further provided, in accordance with an application of the present invention, a method for use with a native valve of a heart of a subject, the method including: percutaneously advancing an implant to the heart, the implant: having an upstream end, a downstream end, and a central longitudinal axis therebetween, and including a tubular portion, an upstream support portion, and a plurality of tissue-engaging flanges; positioning the implant within the heart such that the upstream support portion is disposed upstream of the valve, positioning the implant within the heart such that the tissue-engaging flanges are disposed downstream of the valve, without increasing a diameter of the tubular portion: causing the upstream support portion to extend radially outward from the axis, and causing the flanges to extend radially outward from the axis so as to have a first flange span; and subsequently, by increasing a diameter of the tubular portion: causing the upstream support portion and the flanges move toward each other by at least 5 mm, causing the upstream support portion to move further radially outward from the axis, and causing each flange of the plurality of flanges to translate radially outward so as to have a second flange span that is greater than the first flange span.

The present invention will be more fully understood from the following detailed description of applications thereof, taken together with the drawings, in which:

BRIEF DESCRIPTION OF THE DRAWINGS

FIGS. 1A-B and 2A-E are schematic illustrations of an implant for use with a native valve of a heart of a subject, in accordance with some applications of the invention;

FIGS. 3A-C are schematic illustrations that show structural changes in a frame assembly during transitioning of the assembly between its compressed and expanded states, in accordance with some applications of the invention;

FIGS. 4A-F are schematic illustrations of implantation of the implant at the native valve, in accordance with some applications of the invention;

FIGS. 7A-B and 8A-B are schematic illustrations of frame assemblies of respective implants, in accordance with some applications of the invention; and FIGS. 9A-C are schematic illustrations of an implant comprising a frame assembly, in accordance with some applications of the invention.

DETAILED DESCRIPTION OF EMBODIMENTS

Figure 3B:
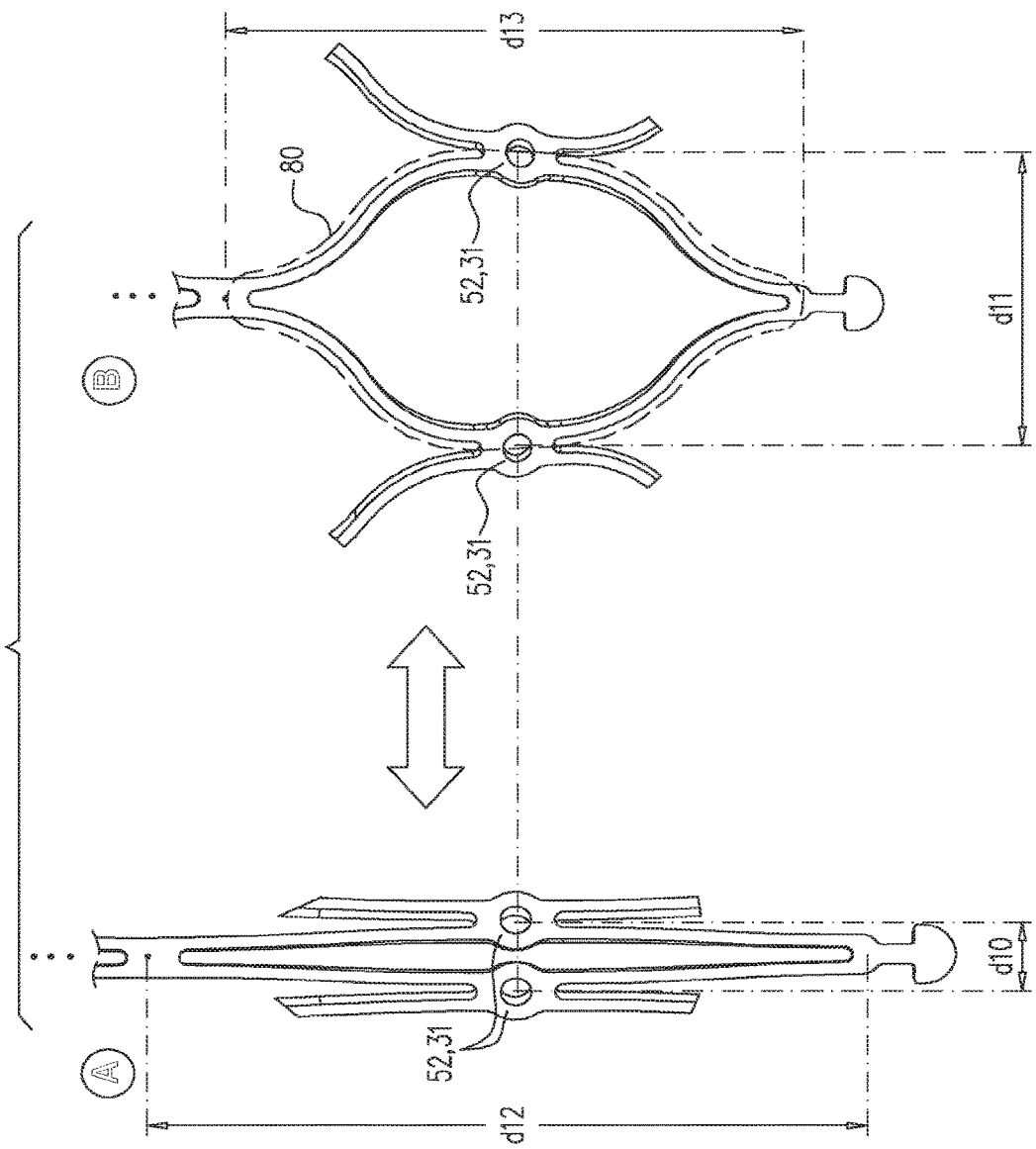

Reference is made to FIGS. 1A-B and 2A-E, which are schematic illustrations of an implant 20 (alternatively, "prosthetic valve 20") for use with a native valve of a heart of a subject, in accordance with some embodiments of the invention. Prosthetic valve 20 comprises a frame assembly 22 that has an upstream end 24 (alternatively, "atrial end 24"), a downstream end 26 (alternatively, "ventricular end 26"), and a central longitudinal axis ax1 therebetween. The term "atrial end" may refer to an end of a given feature configured to be situated closest to an atrium of the heart when prosthetic valve 20 is implanted therein. For example, in FIGS. 1A, 1B, 2A-E, and 4A-F, the atrial end of prosthetic valve 20 may be the top end of prosthetic valve 20. Similarly, the term "ventricular end" may refer to an end of a given feature configured to be situated closest to a ventricle of the heart when prosthetic valve 20 is implanted therein. For example, in FIGS. 1A, 1B, 2A-E, and 4A-F, the ventricular end of prosthetic valve 20 may be the bottom end of prosthetic valve 20. Frame assembly 22 comprises a valve frame 30 (alternatively "inner frame 30") that comprises a tubular portion 32 (alternatively, "inner frame tubular portion 32") that has an atrial end 34 and a ventricular end 36, and is shaped to define a lumen 38 through the inner frame tubular portion 32 from the atrial end to the ventricular end. As illustrated in FIGS. 1A and 1B, inner frame tubular portion 32 may also include one or more projections 28, which extend from ventricular end 36 of inner frame tubular portion 32. Inner frame tubular portion 32 circumscribes axis ax1, and thereby defines lumen 38 along the axis. Inner frame 30 further comprises an atrial support portion 40, extending from atrial end 34 of inner frame tubular portion 32. Frame assembly 22 further comprises at least one leg 50 (alternatively, "ventricular anchor support 50"), coupled to inner frame 30 at (e.g., via) a coupling point 52, and having a tissue-engaging flange 54 (alternatively, "outer frame tissue anchor 54").

In some embodiments, and as described hereinbelow, ventricular anchor support 50 is part of an outer frame 60, and frames 30 and 60 define respective coupling elements 31 and 61, which are fixed with respect to each other at coupling points 52. As illustrated in FIG. 1A, inner frame 30 may be positioned at least partially within outer frame 60. In some embodiments, frames 30 and 60 are coupled to each other only at coupling points 52 (e.g., only via the fixation of coupling elements 31 and 61 with respect to each other).

Prosthetic valve 20 further comprises a valve member 58 (e.g., one or more prosthetic leaflets) disposed within lumen 38, and configured to facilitate one-way liquid flow through the lumen from atrial end 34 to ventricular end 36 (e.g., thereby defining the orientation of the atrial and ventricular ends of inner frame tubular portion 32). FIG. 1A shows prosthetic valve 20 in a fully-expanded state (alternatively, "radially expanded state"), in which frame assembly 22 is in a radially expanded state. FIG. 1B shows an exploded view of frame assembly 22 in its radially expanded state. FIGS. 2A-E show respective states of prosthetic valve 20, which will be discussed in more detail hereinbelow with respect to the implantation of the prosthetic valve and the anatomy in which the prosthetic valve is implanted. FIG. 2A shows prosthetic valve 20 in a compressed state (alternatively, "radially contracted state"), in which frame assembly 22 is in a radially contracted state for percutaneous delivery of the prosthetic valve to the heart of the subject. In some embodiments, in the radially contracted state, ventricular anchor support 50 (including outer frame tissue anchor 54 thereof) is in a constrained-anchor state in which the outer frame tissue anchor is generally parallel with axis ax1. Further, in the radially contracted state, atrial support portion 40 is generally tubular, collinear with inner frame tubular portion 32 (e.g., extending collinearly from the inner frame tubular portion), and disposed around axis ax1.

FIG. 2B shows a state of prosthetic valve 20 in which outer frame tissue anchor 54 of each ventricular anchor support 50 extends radially away from axis ax1 (e.g., radially away from inner frame tubular portion 32). FIG. 2C shows a state of prosthetic valve 20 in which atrial support portion 40 extends radially away from axis ax1 (and thereby radially away from inner frame tubular portion 32). FIG. 2D shows a state of prosthetic valve 20 in which both outer frame tissue anchor 54 and atrial support portion 40 extend away from axis ax1. In the radially expanded state (FIGS. 1A-B) both atrial support portion 40 and outer frame tissue anchor 54 extend radially away from axis ax1. In some embodiments, frame assembly 22 is biased (e.g., shape-set) to assume its radially expanded state, which is shown in FIG. 2E. Transitioning of prosthetic valve 20 between the respective states may be controlled by delivery apparatus, such as by constraining the prosthetic valve in a radially contracted state within a delivery tube and/or against a control rod, and selectively releasing portions of the prosthetic valve to allow them to expand.

In the radially contracted state of frame assembly 22, inner frame tubular portion 32 has a diameter d1, and in the radially expanded state, the inner frame tubular portion has a diameter d2 that is greater that diameter d1. For some embodiments, diameter d1 is 4-15 mm, (e.g., 5-11 mm) and diameter d2 is 20-50 mm, (e.g., 23-33 mm). Frame assembly 22 is configured such that increasing the diameter of inner frame tubular portion 32 (e.g., from d1 to d2) causes longitudinal movement of outer frame tissue anchor 54 away from coupling point 52. In the same way, reducing the diameter of inner frame tubular portion 32 (e.g., from d2 to d1) causes longitudinal movement of outer frame tissue anchor 54 toward coupling point 52. It is to be noted that the term "longitudinal movement" (including the specification and the claims) means movement parallel with central longitudinal axis ax1. Therefore longitudinal movement of outer frame tissue anchor 54 away from coupling point 52 means increasing a distance, measured parallel with longitudinal axis ax1, between outer frame tissue anchor 54 and coupling point 52. An example of such a configuration is described in more detail with respect to FIG. 3A.

Thus, expansion of inner frame tubular portion 32 from its radially contracted state toward its radially expanded state (i) increases a circumferential distance between each of coupling points 52 and its adjacent coupling points (e.g., between each of outer-frame coupling elements 61 and its adjacent outer-frame coupling elements) (e.g., from d8 to d9), and (ii) moves ventricular anchor support 50 in a longitudinally atrial direction with respect to the inner frame tubular portion. The term "atrial direction" may refer to a direction extending upstream from prosthetic valve 20, towards an atrium of the heart. For example, in FIGS. 4A-4F, an "atrial direction" may refer to a direction extending upwards from prosthetic valve 20 towards atrium 6. Similarly, the term "ventricular direction" may refer to a direction extending downstream from prosthetic valve 20, towards a ventricle of the heart. For example, in FIGS. 4A-4F, a "ventricular direction" may refer to a direction extending downwards from prosthetic valve 20 towards ventricle 8.

Figure 3C:
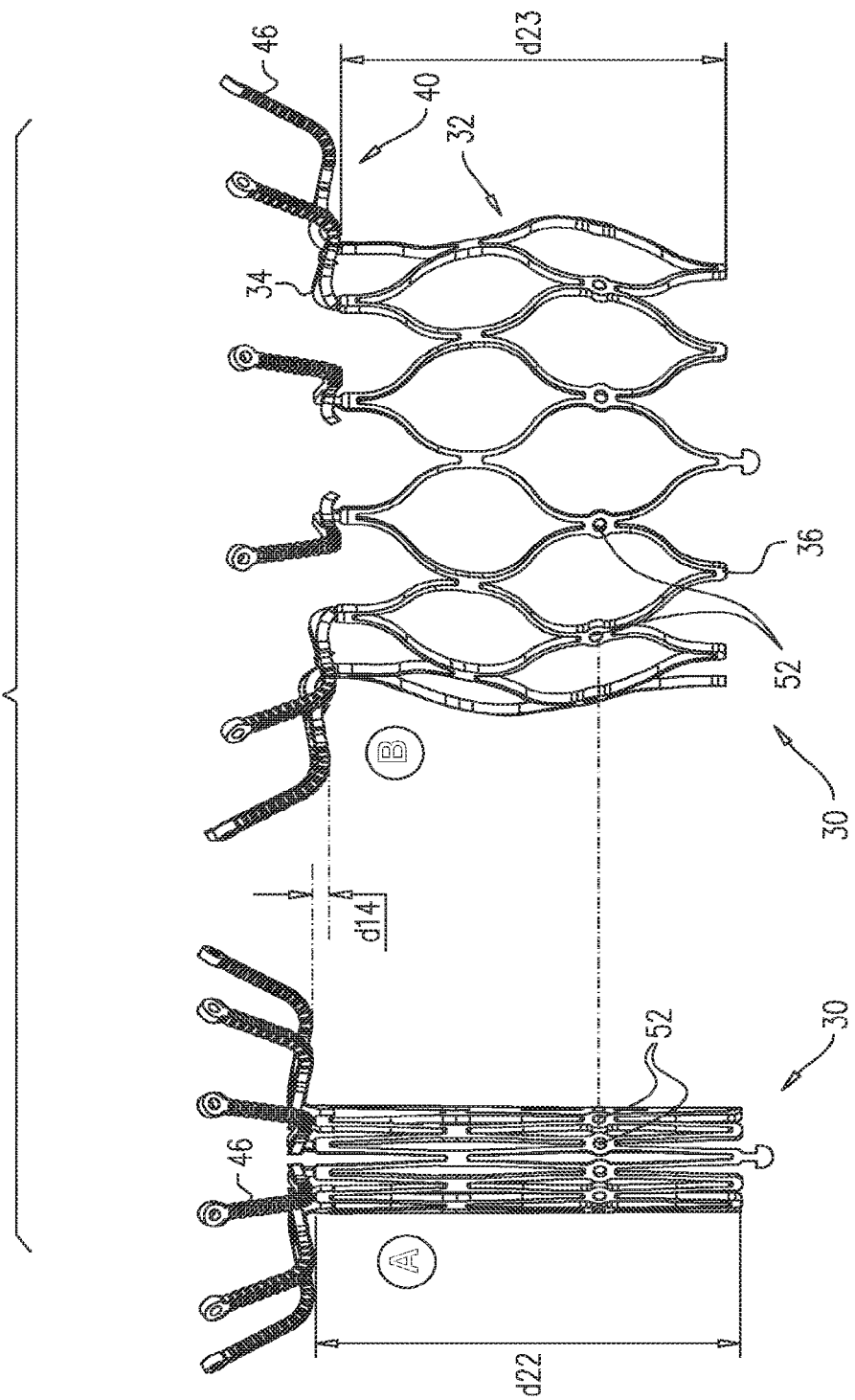

In some embodiments, frame assembly 22 is configured such that increasing the diameter of inner frame tubular portion 32 also causes longitudinal movement of atrial support portion 40 toward coupling point 52, e.g., as described in more detail with respect to FIGS. 3B-C. In some embodiments, frame assembly 22 is configured such that increasing the diameter of inner frame tubular portion 32 also causes longitudinal movement of atrial end 34 of inner frame tubular portion 32 toward coupling point 52. In the same way, reducing the diameter of inner frame tubular portion 32 causes longitudinal movement of atrial end 34 away from coupling point 52.

For some embodiments, atrial support portion 40 comprises a plurality of inner frame tissue anchors 46 that each extends radially outward from inner frame tubular portion 32 (e.g., from atrial end 34 of the inner frame tubular portion). Inner frame tissue anchors 46 are flexible. For some such embodiments, inner frame tissue anchors 46 are coupled to inner frame tubular portion 32 such that each inner frame tissue anchor may deflect independently of adjacent inner frame tissue anchors 46 during implantation (e.g., due to anatomical topography).

For some embodiments, atrial support portion 40 comprises a plurality of barbs 48 that extend out of a ventricular surface of the atrial support portion. For example, each inner frame tissue anchor 46 may comprise one or more of barbs 48. Barbs 48 press into tissue on an atrial side of the native valve (e.g., into the valve annulus), thereby inhibiting movement of prosthetic valve 20 in a ventricular direction (in addition to inhibition of movement in a ventricular direction provided by the geometry of atrial support portion 40).

One or more surfaces of frame assembly 22 are covered with a covering 23, which comprises a flexible sheet, such as a fabric, e.g., comprising polyester. In some embodiments, covering 23 covers at least part of inner frame tubular portion 32, lining an inner surface of the inner frame tubular portion, and thereby defining lumen 38.

Further, atrial support portion 40 is covered with covering 23, e.g., extending between inner frame tissue anchors 46 to form an annular shape. It is hypothesized that this reduces a likelihood of paravalvular leakage. For such embodiments, excess covering 23 may be provided between inner frame tissue anchors 46 of atrial support portion 40, so as to facilitate their independent movement. Although FIG. 1A shows covering 23 covering an atrial side of atrial support portion 40, the covering additionally (or alternatively) covers the ventricular side of the atrial support portion. For example, covering 23 may extend over the tips of inner frame tissue anchors 46 and down the outside of the inner frame tissue anchors, or a separate piece of covering may be provided on the ventricular side of the atrial support portion.

Alternatively, each inner frame tissue anchor 46 may be individually covered in a sleeve of covering 23, thereby facilitating independent movement of the inner frame tissue anchors.

For some embodiments, at least a portion of ventricular anchor support 50 (e.g., outer frame tissue anchors 54 thereof) is covered with covering 23.

In some embodiments, frame assembly 22 comprises a plurality of ventricular anchor supports 50 (e.g., two or more ventricular anchor supports, e.g., 2-16 ventricular anchor supports, such as 4-12 ventricular anchor supports, such as 6-12 ventricular anchor supports), arranged circumferentially around inner frame 30 (e.g., around the outside of inner frame tubular portion 32). In some embodiments, frame assembly 22 comprises a plurality of coupling points 52 at which the ventricular anchor supports are coupled to inner frame 30.

As described in more detail hereinbelow (e.g., with reference to FIG. 3A), each ventricular anchor support 50 may be coupled to a coupling point 52 via a strut 70. For some embodiments, each ventricular anchor support 50 is coupled to a plurality of (e.g., two) coupling points 52 via a respective plurality of (e.g., two) struts 70. For some such embodiments, frame assembly 22 is arranged such that, in the radially expanded state of the frame assembly, ventricular anchor support 50 is disposed, circumferentially with respect to inner frame tubular portion 32, between two struts, and each of the two struts are disposed, circumferentially with respect to the inner frame tubular portion, between the ventricular anchor support and a respective coupling point 52.

For some embodiments, a plurality of (e.g., two) ventricular anchor supports 50 are coupled to each coupling point 52 via a respective plurality of (e.g., two) struts 70. For some such embodiments, frame assembly 22 is arranged such that, in the radially expanded state of the frame assembly, coupling point 52 is disposed, circumferentially with respect to inner frame tubular portion 32, between two struts 70, and each of the two struts are disposed, circumferentially with respect to the inner frame tubular portion, between the coupling point and a respective ventricular anchor support 50.

For some embodiments, frame assembly 22 comprises an outer frame 60 that circumscribes inner frame tubular portion 32, comprises (or defines) the plurality of ventricular anchoring supports 50 and the plurality of struts 70, and is coupled to inner frame 30 at the plurality of coupling points 52, such that the plurality of ventricular anchoring supports are distributed circumferentially around the inner frame tubular portion. For such embodiments, outer frame 60 comprises a ring 66 that is defined by a pattern of alternating peaks 64 and troughs 62, and that circumscribes inner frame tubular portion 32. For example, the ring may comprise struts 70, extending between the peaks and troughs. Peaks 64 are longitudinally closer to atrial end 34 of inner frame tubular portion 32 than to ventricular end 36, and troughs 62 are longitudinally closer to the ventricular end than to the atrial end. (It is to be noted that throughout this patent application, including the specification and the claims, the term "longitudinally" means with respect to longitudinal axis ax1. For example, "longitudinally closer" means closer along axis ax1 (whether positioned on axis ax1 or lateral to axis ax1), and "longitudinal movement" means a change in position along axis ax1 (which may be in additional to movement toward or away from axis ax1). Therefore, peaks 64 are closer than troughs 62 to atrial end 34, and troughs 62 are closer than peaks 64 to ventricular end 36. As illustrated in FIG. 1B, outer frame 60 may include multiple rings 66 (e.g. two rings 66) which are connected by ventricular anchoring supports 50. Rings 66 and ventricular anchor supports 50 may form an annular outer frame tubular portion 65. Annular outer frame tubular portion 65 may have an atrial end 67 and a ventricular end 69, and may circumscribe axis ax1. As also illustrated in FIG. 1B, outer frame tissue anchors 54 may extend from annular outer frame tubular portion 65. For embodiments in which frame 60 comprises ring 66, each ventricular anchor support 50 is coupled to the ring (or defined by frame 60) at a respective trough 62.

In the embodiment shown, the peaks and troughs are defined by ring 66 having a generally zig-zag shape. However, the scope of the invention includes ring 66 having another shape that defines peaks and troughs, such as a serpentine or sinusoid shape.

For embodiments in which frame assembly 22 has a plurality of coupling points 52, the coupling points (and therefore coupling elements 31 and 61) are disposed circumferentially around the frame assembly (e.g., around axis ax1), in some embodiments on a transverse plane that is orthogonal to axis ax1. This transverse plane is illustrated by the position of section A-A in FIG. 2B. Alternatively, coupling points 52 may be disposed at different longitudinal heights of frame assembly 22, e.g., such that different outer frame tissue anchors 54 are positioned and/or moved differently to others. In some embodiments, coupling points 52 (and therefore coupling elements 31 and 61) are disposed longitudinally between atrial end 24 and ventricular end 26 of frame assembly 22, but not at either of these ends. Further in some embodiments, coupling points 52 are disposed longitudinally between atrial end 34 and ventricular end 36 of inner frame tubular portion 32, but not at either of these ends. For example, the coupling points may be more than 3 mm (e.g., 4-10 mm) both from end 34 and from end 36. It is hypothesized that this advantageously positions the coupling points at a part of inner frame tubular portion 32 that is more rigid than end 34 or end 36.

It is to be noted that ventricular anchor support 50 is expandable into its radially expanded state (e.g., a released-anchor state) such that outer frame tissue anchor 54 extends away from axis ax1, independently of increasing the diameter of inner frame tubular portion 32 (e.g., as shown in FIGS. 2B & 2D). Similarly, atrial support portion 40 is expandable into its radially expanded state (e.g., a released-anchor state) such that it (e.g., inner frame tissue anchors 46 thereof) extends away from axis ax1, independently of increasing the diameter of inner frame tubular portion 32 (e.g., as shown in FIGS. 2C & 2D). The state shown in FIG. 2D may be considered to be an intermediate state. Therefore, prosthetic valve 20 is configured such that ventricular anchor supports 50 (e.g., outer frame tissue anchors 54 thereof) and atrial support portion 40 are expandable such that they both extend away from axis ax1, while retaining a distance d3 therebetween. This distance is subsequently reducible to a distance d4 by expanding inner frame tubular portion 32 (e.g., shown in FIG. 2E).

For some embodiments, while inner frame tubular portion 32 remains in its radially contracted state, outer frame tissue anchor 54 can extend away from axis ax1 over 40 percent (e.g., 40-80 percent, such as 40-70 percent) of the distance that it extends from the axis subsequent to the expansion of the inner frame tubular portion. For example, for embodiments in which prosthetic valve 20 comprises a outer frame tissue anchor 54 on opposing sides of the prosthetic valve, a span d15 of the outer frame tissue anchors while inner frame tubular portion 32 is in its radially contracted state may be at least 40 percent (e.g., 40-80 percent, such as 40-70 percent) as great as a span d16 of the outer frame tissue anchors subsequent to the expansion of the inner frame tubular portion. For some embodiments, span d15 is greater than 15 mm and/or less than 50 mm (e.g., 20-30 mm). For some embodiments, span d16 is greater than 30 mm and/or less than 60 mm (e.g., 40-50 mm). It is to be noted that outer frame tissue anchor 54 is effectively fully radially expanded, with respect to other portions of ventricular anchor support 50 and/or with respect to inner frame tubular portion 32, before and after the expansion of the inner frame tubular portion.

Similarly, for some embodiments, while inner frame tubular portion 32 remains in its radially contracted state, atrial support portion 40 (e.g., inner frame tissue anchors 46) can extend away from axis ax1 over 30 percent (e.g., 30-70 percent) of the distance that it extends from the axis subsequent to the expansion of the inner frame tubular portion. That is, for some embodiments, a span d17 of the atrial support portion while inner frame tubular portion 32 is in its radially contracted state may be at least 30 percent (e.g., 30-70 percent) as great as a span d18 of the atrial support portion subsequent to the expansion of the inner frame tubular portion. For some embodiments, span d17 is greater than 16 mm (e.g., greater than 20 mm) and/or less than 50 mm (e.g., 30-40 mm). For some embodiments, span d18 is greater than 40 mm and/or less than 65 mm (e.g., 45-56 mm, such as 45-50 mm). It is to be noted that atrial support portion 40 is effectively fully radially expanded, with respect to inner frame tubular portion 32, before and after the expansion of the inner frame tubular portion.

It is to be noted that when inner frame tubular portion 32 is radially expanded, outer frame tissue anchors 54 translate radially outward from span d15 to span d16 (e.g., without deflecting). In some embodiments atrial support portion 40 behaves similarly (e.g., inner frame tissue anchors 46 translated radially outward from span d17 to span d18, e.g., without deflecting). That is, an orientation of each outer frame tissue anchor 54 and/or each inner frame tissue anchor 46 with respect to inner frame tubular portion 32 and/or axis ax1 is the same in the state shown in FIG. 2D as it is in the state shown in FIG. 2E. Similarly, for some embodiments an orientation of each outer frame tissue anchor 54 with respect to atrial support portion 40 (e.g., with respect to one or more inner frame tissue anchors 46 thereof) is the same before and after expansion of inner frame tubular portion 32.

For some embodiments, increasing the diameter of inner frame tubular portion 32 from d1 to d2 causes greater than 1 mm and/or less than 20 mm (e.g., 1-20 mm, such as 1-10 mm or 5-20 mm) of longitudinal movement of outer frame tissue anchor 54 away from coupling point 52. For some embodiments, increasing the diameter of inner frame tubular portion 32 from d1 to d2 causes greater than 1 mm and/or less than 20 mm (e.g., 1-20 mm, such as 1-10 mm or 5-20 mm) of longitudinal movement of atrial support portion 40 toward coupling point 52. For some embodiments, distance d3 is 7-30 mm. For some embodiments, distance d4 is 0-15 mm (e.g., 2-15 mm). For some embodiments, increasing the diameter of inner frame tubular portion 32 from d1 to d2 reduces the distance between the atrial support portion and outer frame tissue anchors 54 by more than 5 mm and/or less than 30 mm, such as 5-30 mm (e.g., 10-30 mm, such as 10-20 mm or 20-30 mm). For some embodiments, the difference between d3 and d4 is generally equal to the difference between d1 and d2. For some embodiments, the difference between d3 and d4 is more than 1.2 and/or less than 3 times (e.g., 1.5-2.5 times, such as about 2 times) greater than the difference between d1 and d2.

For some embodiments, outer frame tissue anchors 54 curve such that a tip of each outer frame tissue anchor 54 is disposed at a shallower angle with respect to inner region 42 of atrial support portion 40, than are portions of ventricular anchor support 50 that are closer to ventricular end 26 of frame assembly 22. For some such embodiments, a tip of each outer frame tissue anchor may be generally parallel with inner region 42. For some such embodiments, while inner frame tubular portion 32 is in its radially expanded state, a tip portion 55 of each outer frame tissue anchor 54 that extends from the tip of the outer frame tissue anchor at least 2 mm along the outer frame tissue anchor, is disposed within 2 mm of atrial support portion 40. Thus, for some embodiments, while inner frame tubular portion 32 is in its radially expanded state, for at least 5 percent (e.g., 5-8 percent, or at least 8 percent) of span 18 of atrial support portion 40, the atrial support portion is disposed within 2 mm of an outer frame tissue anchor 54.

For some embodiments, in the absence of any obstruction (such as tissue of the valve or covering 23) between outer frame tissue anchor 54 and atrial support portion 40, increasing the diameter of inner frame tubular portion 32 from d1 to d2 causes the outer frame tissue anchor 54 and the atrial support portion to move past each other (e.g., the outer frame tissue anchor 54 may move between inner frame tissue anchors 46 of the atrial support portion), such that the outer frame tissue anchor 54 is closer to the atrial end of prosthetic valve 20 than is the atrial support portion, e.g., as shown hereinbelow for frame assemblies 122 and 222, mutatis mutandis. (For embodiments in which atrial support portion 40 is covered by covering 23, outer frame tissue anchors 54 do not pass the covering. For example, in the absence of any obstruction, outer frame tissue anchors 54 may between inner frame tissue anchors 46, and press directly against covering 23.) It is hypothesized that for some embodiments this configuration applies greater force to the valve tissue being sandwiched, and thereby further facilitates anchoring of the prosthetic valve. That is, for some embodiments, distance d3 is smaller than the sum of distance d5 and a distance d14 (described with reference to FIG. 3C). For some embodiments, increasing the diameter of inner frame tubular portion 32 from d1 to d2 advantageously causes outer frame tissue anchors 54 and atrial support portion 40 to move greater than 3 mm and/or less than 25 mm (e.g., greater than 5 mm and/or less than 15 mm, e.g., 5-10 mm, such as about 7 mm) with respect to each other (e.g., toward each other and then past each other).

In some embodiments, in the radially expanded state of frame assembly 22, atrial support portion 40 has an inner region (e.g., an inner ring) 42 that extends radially outward at a first angle with respect to axis ax1 (and with respect to inner frame tubular portion 32), and an outer region (e.g., an outer ring) 44 that extends, from the inner region, further radially outward from the inner frame tubular portion at a second angle with respect to the inner frame tubular portion, the second angle being smaller than the first angle. For example, for some embodiments inner region 42 extends radially outward at an angle alpha_1 of 60-120 degrees (e.g., 70-110 degrees) with respect to axis ax1, and outer region 44 extends radially outward at an angle alpha_2 of 5-70 degrees (e.g., 10-60 degrees) with respect to axis ax1.

It is to be noted that angles alpha_1 and alpha_2 are measured between the respective region support portion 40, and the portion of axis ax1 that extends in an atrial direction from the level of frame assembly 22 at which the respective region begins to extend radially outward.

For some embodiments in which prosthetic valve 20 is configured to be placed at an atrioventricular valve (e.g., a mitral valve or a tricuspid valve) of the subject, region 42 is configured to be placed against the atrial surface of the annulus of the atrioventricular valve, and region 44 is configured to be placed against the walls of the atrium upstream of the valve.

For some embodiments, outer region 44 is more flexible than inner region 42. For example, and as shown, each inner frame tissue anchor 46 may have a different structure in region 44 than in region 42. It is hypothesized that the relative rigidity of region 42 provides resistance against ventricular migration of prosthetic valve 20, while the relative flexibility of region 44 facilitates conformation of atrial support portion 40 to the atrial anatomy.

For some embodiments, two or more of inner frame tissue anchors 46 are connected by a connector (not shown), reducing the flexibility, and/or the independence of movement of the connected inner frame tissue anchors relative to each other. For some embodiments, inner frame tissue anchors 46 are connected in particular sectors of atrial support portion 40, thereby making these sectors more rigid than sectors in which the inner frame tissue anchors are not connected. For example, a relatively rigid sector may be provided to be placed against the posterior portion of the mitral annulus, and a relatively flexible sector may be provided to be placed against the anterior side of the mitral annulus, so as to reduce forces applied by atrial support portion 40 on the aortic sinus.

For some embodiments, and as shown, coupling points 52 are disposed closer to ventricular end 26 of frame assembly 22 than are outer frame tissue anchors 54, or is atrial support portion 40.

As described in more detail with respect to FIGS. 4A-F, the movement of outer frame tissue anchor 54 away from coupling point 52 (and the typical movement of atrial support portion 40 toward the coupling point) facilitates the sandwiching of tissue of the native valve (e.g., leaflet and/or annulus tissue) between the outer frame tissue anchor 54 and the atrial support portion, thereby securing prosthetic valve 20 at the native valve.

In some embodiments, in the radially contracted state of inner frame tubular portion 32, a ventricular end of each ventricular anchor support 50 is longitudinally closer than valve-frame coupling elements 31 to ventricular end 36, and outer frame tissue anchor 54 of each ventricular anchor support 50 is disposed longitudinally closer than the valve-frame coupling elements to atrial end 34. In some embodiments, this is also the case in the radially expanded state of inner frame tubular portion 32.

FIGS. 3A-C show structural changes in frame assembly 22 during transitioning of the assembly between its radially contracted and radially expanded states, in accordance with some embodiments of the invention. FIGS. 3A-C each show a portion of the frame assembly, the structural changes thereof being representative of the structural changes that occur in other portions of the frame assembly. FIG. 3A shows a ventricular anchor support 50 and struts 70 (e.g., a portion of outer frame 60), and illustrates the structural changes that occur around outer frame 60. FIG. 3B shows a portion of inner frame 30, and illustrates the structural changes that occur around the inner frame. FIG. 3C shows inner frame 30 as a whole. In each of FIGS. 3A-C, state (A) illustrates the structure while frame assembly 22 (and in particular inner frame tubular portion 32) is in its radially contracted state, and state (B) illustrates the structure while the frame assembly (and in particular inner frame tubular portion 32) is in its radially expanded state.

FIG. 3A shows structural changes in the coupling of ventricular anchoring supports 50 to coupling point 52 (e.g., structural changes of outer frame 60) during the transitioning of frame assembly 22 (and in particular inner frame tubular portion 32) between its radially contracted and radially expanded states. Each ventricular anchor support 50 is coupled to inner frame 30 via at least one strut 70, which connects the ventricular anchoring support to coupling point 52. In some embodiments, each ventricular anchor support 50 is coupled to inner frame 30 via a plurality of struts 70. A first end 72 of each strut 70 is coupled to ventricular anchor support 50, and a second end 74 of each strut is coupled to a coupling point 52. As described hereinabove, for embodiments in which frame 60 comprises ring 66, each ventricular anchor support 50 is coupled to the ring at a respective trough 62. Ring 66 may comprise struts 70, extending between the peaks and troughs, with each first end 72 at (or close to) a trough 62, and each second end 74 at (or close to) a peak 64. As depicted in FIGS. 1B and 3A, first end 72 may form the ventricular end 69 of outer frame tubular portion 65.

In the radially contracted state of frame assembly 22 (and in particular of inner frame tubular portion 32), each strut 70 is disposed at a first angle in which first end 72 is disposed closer than second end 74 to the ventricular end of the frame assembly. Expansion of frame assembly 22 (and in particular of inner frame tubular portion 32) toward its radially expanded state causes strut 70 to deflect to a second angle. This deflection moves first end 72 away from the ventricular end of frame assembly 22. That is, in the radially expanded state of frame assembly 22, first end 72 is further from the ventricular end of the frame assembly than it is when the frame assembly is in its radially contracted state. This movement is shown as a distance d5 between the position of end 72 in state (A) and its position in state (B). This movement causes the above-described movement of outer frame tissue anchors 54 away from coupling points 52. As shown, outer frame tissue anchors 54 move the same distance d5 in response to expansion of frame assembly 22. Since outer frame tissue anchors 54 and first end 72 (i.e., ventricular end 69) move the same distance d5 in response to expansion of frame assembly 22, the axial distance (i.e., the distance along axis ax1) between outer frame tissue anchors 54 and first end 72 (i.e., ventricular end 69) may remain constant between the radially expanded state and the radially contracted state of annular outer frame 60.

For embodiments in which outer frame 60 comprises ring 66, the pattern of alternating peaks and troughs may be described as having an amplitude longitudinally between the peaks and troughs, i.e., measured parallel with central longitudinal axis ax1 of frame assembly 22, and the transition between the radially contracted and radially expanded states may be described as follows: In the radially contracted state of frame assembly 22 (and in particular of inner frame tubular portion 32), the pattern of ring 66 has an amplitude d20. In the radially expanded state frame assembly 22 (and in particular of inner frame tubular portion 32), the pattern of ring 66 has an amplitude d21 that is lower than amplitude d20. Because (i) it is at peaks 64 that ring 66 is coupled to inner frame 30 at coupling points 52, and (ii) it is at troughs 62 that ring 66 is coupled to ventricular anchoring supports 50, this reduction in the amplitude of the pattern of ring 66 moves ventricular anchoring supports 50 (e.g., outer frame tissue anchors 54 thereof) longitudinally further from the ventricular end of the frame assembly. The magnitude of this longitudinal movement (e.g., the difference between magnitudes d20 and d21) is equal to d5.

In some embodiments, distance d5 is the same distance as the distance that outer frame tissue anchor 54 moves away from coupling point 52 during expansion of the frame assembly. That is, a distance between outer frame tissue anchor 54 and the portion of ventricular anchor support 50 that is coupled to strut 70, remains constant during expansion of the frame assembly. For some embodiments, the longitudinal movement of outer frame tissue anchor 54 away from coupling point 52 is a translational movement (e.g., a movement that does not include rotation or deflection of the outer frame tissue anchor 54).

For some embodiments, a distance d6, measured parallel to axis ax1 of frame assembly 22, between coupling point 52 and first end 72 of strut 70 while assembly 22 is in its radially contracted state, is 3-15 mm. For some embodiments, a distance d7, measured parallel to axis ax1, between coupling point 52 and first end 72 of strut 70 while assembly 22 is in its radially expanded state, is 1-5 mm (e.g., 1-4 mm).

For some embodiments, amplitude d20 is 2-10 mm (e.g., 4-7 mm). For some embodiments, amplitude d21 is 4-9 mm (e.g., 5-7 mm).

For some embodiments, and as shown, in the radially expanded state, first end 72 of strut 70 is disposed closer to the ventricular end of frame assembly 22 than is coupling point 52. For some embodiments, in the radially expanded state, first end 72 of strut 70 is disposed further from the ventricular end of frame assembly 22 than is coupling point 52.

For embodiments in which frame assembly 22 comprises a plurality of ventricular anchoring supports 50 and a plurality of coupling points 52 (e.g., for embodiments in which the frame assembly comprises annular outer frame 60) expansion of the frame assembly increases a circumferential distance between adjacent coupling points 52, and an increase in a circumferential distance between adjacent ventricular anchoring supports 50. FIG. 3A shows such an increase in the circumferential distance between adjacent coupling points 52, from a circumferential distance d8 in the radially contracted state to a circumferential distance d9 in the radially expanded state. For some embodiments, distance d8 is 1-6 mm. For some embodiments, distance d9 is 3-15 mm.

For some embodiments, in addition to being coupled via ring 66 (e.g., struts 70 thereof) ventricular anchoring supports 50 are also connected to each other via connectors 78. Connectors 78 allow the described movement of ventricular anchoring supports 50 during expansion of frame assembly 22, but stabilize ventricular anchoring supports 50 relative to each other while the frame assembly is in its radially expanded state. For example, connectors 78 may bend and/or deflect during expansion of the frame assembly.

FIGS. 3B-C show structural changes in inner frame 30 during the transitioning of frame assembly 22 between its radially contracted and radially expanded states. Inner frame tubular portion 32 of inner frame 30 is defined by a plurality of cells 80, which are defined by the repeating pattern of the inner frame. When frame assembly 22 is radially expanded from its radially contracted state toward its radially expanded state, cells 80 (i) widen from a width d10 to a width d11 (measured orthogonal to axis ax1 of the frame assembly), and (ii) shorten from a height d12 to a height d13 (measured parallel to axis ax1 of the frame assembly). This shortening reduces the overall height (i.e., a longitudinal length between atrial end 34 and ventricular end 36) of inner frame tubular portion 32 from a height d22 to a height d23, and thereby causes the above-described longitudinal movement of atrial support portion 40 toward coupling points 52 by a distance d14 (shown in FIG. 3C). For some embodiments, and as shown, coupling points 52 are disposed at the widest part of each cell.

Due to the configurations described herein, the distance by which outer frame tissue anchors 54 move with respect to (e.g., toward, or toward-and-beyond) atrial support portion 40 (e.g., inner frame tissue anchors 46 thereof), is greater than the reduction in the overall height of inner frame tubular portion 32 (e.g., more than 20 percent greater, such as more than 30 percent greater, such as more than 40 percent greater). That is, prosthetic valve 20 comprises: an inner frame (30) that comprises an inner frame tubular portion (32) that circumscribes a longitudinal axis (ax1) of the inner frame so as to define a lumen (38) along the axis, the inner frame tubular portion having an atrial end (34), a ventricular end (36), a longitudinal length therebetween, and a diameter (e.g., d1 or d2) transverse to the longitudinal axis; a valve member (58), coupled to the inner frame tubular portion, disposed within the lumen, and arranged to provide unidirectional atrial-to-ventricular flow of blood through the lumen; an atrial support portion (40), coupled to the inner frame tubular portion; and an annular outer frame (60), coupled to the inner frame tubular portion, and comprising an outer frame tissue anchor (54), wherein: the prosthetic valve has a first state (e.g., as shown in FIG. 2D and FIG. 4D) and a second state (e.g., as shown in FIG. 2E and FIG. 4E), in both the first state and the second state, (i) the atrial support portion extends radially outward from the inner frame tubular portion, and (ii) the outer frame tissue anchor 54 extends radially outward from the inner frame tubular portion, and the inner frame tubular portion, the atrial support portion, and the outer frame are arranged such that transitioning of the prosthetic valve from the first state toward the second state: increases the diameter of the inner frame tubular portion by a diameter-increase amount (e.g., the difference between d1 and d2), decreases the length of the inner frame tubular portion by a length-decrease amount (e.g., the difference between d22 and d23), and moves the outer frame tissue anchor 54 a longitudinal distance with respect to (e.g., toward or toward-and-beyond) the atrial support portion (e.g., the difference between d3 and d4), this distance being greater than the length-decrease amount.

As shown in the figures, inner frame 30 is coupled to outer frame 60 by coupling between (i) a valve-frame coupling element 31 defined by inner frame 30, and (ii) an outer-frame coupling element 61 defined by outer frame 60 (e.g., an outer-frame coupling element is coupled to end 74 of each strut). In some embodiments, elements 31 and 61 are fixed with respect to each other. Each coupling point 52 is thereby defined as the point at which a valve-frame coupling element and a corresponding outer-frame coupling element 61 are coupled (e.g., are fixed with respect to each other). For some embodiments, and as shown, elements 31 and 61 are eyelets configured to be coupled together by a connector, such as a pin or suture. For some embodiments, elements 31 and 61 are soldered or welded together.

In some embodiments, and as shown, valve-frame coupling elements 31 are defined by inner frame tubular portion 32, and are disposed circumferentially around central longitudinal axis ax1. Outer-frame coupling elements 61 are coupled to ring 66 (or defined by annular outer frame 60, such as by ring 66) at respective peaks 64.

As shown (e.g., in FIGS. 2A-E), inner frame 30 (e.g., inner frame tubular portion 32 thereof) and annular outer frame 60 (e.g., ring 66 thereof) are arranged in a close-fitting coaxial arrangement, in both the radially expanded and radially contracted states of frame assembly 22. Ignoring spaces due to the cellular structure of the frames, a radial gap d19 between inner frame 30 (e.g., inner frame tubular portion 32 thereof) and outer frame 60 (e.g., ring 66 thereof) may be less than 2 mm (e.g., less than 1 mm), in both the radially contracted and radially expanded states, and during the transition therebetween. This is facilitated by the coupling between frames 30 and 60, and the behavior, described hereinabove, of annular outer frame 60 in response to changes in the diameter of inner frame tubular portion 32 (e.g., rather than solely due to delivery techniques and/or tools). For some embodiments, more than 50 percent (e.g., more than 60 percent) of ring 66 is disposed within 2 mm of inner frame tubular portion 32 in both the radially contracted and radially expanded states, and during the transition therebetween. For some embodiments, more than 50 percent (e.g., more than 60 percent) of annular outer frame 60, except for outer frame tissue anchors 54, is disposed within 2 mm of inner frame tubular portion 32 in both the radially contracted and radially expanded states, and during the transition therebetween.

The structural changes to frame assembly 22 (e.g., to outer frame 60 thereof) are described hereinabove as they occur during (e.g., as a result of) expansion of the frame assembly (in particular inner frame tubular portion 32 thereof). This is the natural way to describe these changes because, as described hereinbelow with respect to FIGS. 4A-6, assembly 22 is in its radially contracted state during percutaneous delivery to the prosthetic valve site, and is subsequently radially expanded. However, the nature of prosthetic valve 20 may be further understood by describing structural changes that occur during compression of the frame assembly (e.g., a transition from the radially expanded state in FIG. 2E to the intermediate state in FIG. 2D), in particular inner frame tubular portion 32 thereof (including if inner frame tubular portion 32 were radially contracted by application of compressive force to the inner frame tubular portion, and not to frame 60 except via the inner frame tubular portion pulling frame 60 radially inward). Such descriptions may also be relevant because prosthetic valve 20 is radially contracted (i.e., "crimped") soon before its percutaneous delivery, and therefore these changes may occur while prosthetic valve 20 is in the care of the operating physician.

For some embodiments, the fixation of peaks 64 to respective sites of inner frame tubular portion 32 is such that compression of the inner frame tubular portion from its radially expanded state toward its radially contracted state such that the respective sites of the inner frame tubular portion pull the peaks radially inward via radially-inward tension on coupling points 52: (i) reduces a circumferential distance between each of the coupling points and its adjacent coupling points (e.g., from d9 to d8), and (ii) increases the amplitude of the pattern of ring 66 (e.g., from d21 to d20).

For some embodiments, the fixation of outer-frame coupling elements 61 to valve-frame coupling elements 31 is such that compression of inner frame tubular portion 32 from its radially expanded state toward its radially contracted state such that the valve-frame coupling elements pull the outer-frame coupling elements radially inward: (i) reduces a circumferential distance between each of the outer-frame coupling elements and its adjacent outer-frame coupling elements (e.g., from d9 to d8), and (ii) increases the amplitude of the pattern of ring 66 (e.g., from d21 to d20).

For some embodiments, the fixation of peaks 64 to the respective sites of inner frame tubular portion 32 is such that compression of the inner frame tubular portion from its radially expanded state toward its radially contracted state (i) pulls the peaks radially inward via radially-inward pulling of the respective sites of the inner frame tubular portion on the peaks, (ii) reduces a circumferential distance between each of coupling points 52 and its adjacent coupling points (e.g., from d9 to d8), and (iii) increases the amplitude of the pattern of ring 66 (e.g., from d21 to d20), without increasing radial gap d19 between inner frame 30 (e.g., inner frame tubular portion 32 thereof) and the ring by more than 1.5 mm.

For some embodiments, the fixation of outer-frame coupling elements 61 with respect to valve-frame coupling elements 31 is such that compression of inner frame tubular portion 32 from its radially expanded state toward its radially contracted state (i) pulls outer-frame coupling elements 61 radially inward via radially-inward pulling of valve-frame coupling elements 31 on outer-frame coupling elements 61, (ii) reduces a circumferential distance between each of the outer-frame coupling elements and its adjacent outer-frame coupling elements (e.g., from d9 to d8), and (iii) increases the amplitude of the pattern of ring 66 (e.g., from d21 to d20), without increasing radial gap d19 between inner frame 30 (e.g., inner frame tubular portion 32 thereof) and the ring by more than 1.5 mm.

Reference is made to FIGS. 4A-F, which are schematic illustrations of implantation of prosthetic valve 20 at a native valve 10 of a heart 4 of a subject, in accordance with some embodiments of the invention. Valve 10 is shown as a mitral valve of the subject, disposed between a left atrium 6 and a left ventricle 8 of the subject. However prosthetic valve 20 may be implanted at another heart valve of the subject, mutatis mutandis. Similarly, although FIGS. 4A-F show prosthetic valve 20 being delivered transseptally via a sheath 88, the prosthetic valve may alternatively be delivered by any other suitable route, such as transatrially, or transapically.

Prosthetic valve 20 is delivered, in its radially contracted state, to native valve 10 using a delivery tool 89 that is operable from outside the subject (FIG. 4A). In some embodiments, prosthetic valve 20 is delivered within a delivery capsule 90 of tool 89, which retains the prosthetic valve in its radially contracted state. A transseptal approach, such as a transfemoral approach, is shown. In some embodiments, prosthetic valve 20 is positioned such that at least outer frame tissue anchors 54 are disposed in a ventricular direction of the native valve (i.e., within ventricle 8). At this stage, frame assembly 22 of prosthetic valve 20 is as shown in FIG. 2A.

Subsequently, outer frame tissue anchors 54 are allowed to protrude radially outward, as described hereinabove, e.g., by releasing them from capsule 90 (FIG. 4B). For example, and as shown, capsule 90 may comprise a distal capsule-portion 92 and a proximal capsule-portion 94, and the distal capsule-portion may be moved distally with respect to prosthetic valve 20, so as to expose outer frame tissue anchors 54. At this stage, frame assembly 22 of prosthetic valve 20 is as shown in FIG. 2B.

Subsequently, prosthetic valve 20 is moved upstream in an atrial direction, such that atrial support portion 40, in its radially contracted state, is disposed in an atrial direction of leaflets 12 (i.e., within atrium 6). For some embodiments, the atrial movement of prosthetic valve 20 causes outer frame tissue anchors 54 to engage leaflets 12. However, because of the relatively large distance d3 provided by prosthetic valve 20 (described hereinabove), for some embodiments it is not necessary to move the prosthetic valve so far in an atrial direction that outer frame tissue anchors 54 tightly engage leaflets 12 and/or pull the leaflets in an atrial direction of the valve annulus. Atrial support portion 40 is then allowed to expand such that it protrudes radially outward, as described hereinabove, e.g., by releasing it from capsule 90 (FIG. 4D). For example, and as shown, proximal capsule-portion 94 may be moved proximally with respect to prosthetic valve 20, so as to expose atrial support portion 40. At this stage, frame assembly 22 of prosthetic valve 20 is as shown in FIG. 2D, in which: (i) distance d3 exists between atrial support portion 40 and outer frame tissue anchors 54, (ii) the outer frame tissue anchors have span d15, (iii) the atrial support portion has span d17, and (iv) inner frame tubular portion 32 has diameter d1.

In some embodiments, expansion of frame assembly 22 is inhibited by distal capsule-portion 92 (e.g., by inhibiting expansion of inner frame tubular portion 32), and/or by another portion of delivery tool 89 (e.g., a portion of the delivery tool that is disposed within lumen 38).

Subsequently, prosthetic valve 20 is allowed to expand toward its radially expanded state, such that inner frame tubular portion 32 widens to diameter d2, and the distance between atrial support portion 40 and outer frame tissue anchors 54 reduces to distance d4 (FIG. 4E). This sandwiches tissue of valve 10 (including annular tissue and/or leaflets 12 in some embodiments) between atrial support portion 40 and outer frame tissue anchors 54, thereby securing prosthetic valve 20 at the valve. As depicted in FIG. 4E, atrial support portion 40, including inner frame tissue anchors 46, may engage atrial tissue of the native mitral valve (i.e., may engage the native mitral valve from the atrial side) while outer frame tissue anchors may engage ventricular tissue of the native mitral valve (i.e., may engage the native mitral valve from the ventricular side). FIG. 4F shows delivery capsule 90 having been removed from the body of the subject, leaving prosthetic valve 20 in place at valve 10.

As described hereinabove, prosthetic valve 20 is configured such that when inner frame tubular portion 32 is radially expanded, outer frame tissue anchors 54 and atrial support portion 40 move a relatively large distance toward each other. This enables distance d3 to be relatively large, while distance d4 is sufficiently small to provide effective anchoring. As also described hereinabove, prosthetic valve 20 is configured such that outer frame tissue anchors 54 and atrial support portion 40 can extend radially outward a relatively large distance while inner frame tubular portion 32 remains radially contracted. It is hypothesized that for some embodiments, these configurations (independently and/or together) facilitate effective anchoring of prosthetic valve 20, by facilitating placement of a relatively large proportion of valve tissue (e.g., leaflets 12) between the outer frame tissue anchors 54 and the atrial support portion prior to expanding inner frame tubular portion 32 and sandwiching the valve tissue.

It is further hypothesized that the relatively great radially-outward extension of outer frame tissue anchors 54 and atrial support portion 40 prior to expansion of inner frame tubular portion 32, further facilitates the anchoring/sandwiching step by reducing radially-outward pushing of the valve tissue (e.g., leaflets 12) during the expansion of the inner frame tubular portion, and thereby increasing the amount of valve tissue that is sandwiched.

It is yet further hypothesized that this configuration of prosthetic valve 20 facilitates identifying correct positioning of the prosthetic valve (i.e., with atrial support portion 40 in an atrial direction of leaflets 12 and outer frame tissue anchors 54 in a ventricular direction of the leaflets) prior to expanding inner frame tubular portion 32 and sandwiching the valve tissue.

As shown in FIG. 1A, for some embodiments, in the radially expanded state of frame assembly 22, prosthetic valve 20 defines a toroidal space 49 between outer frame tissue anchors 54 and atrial support portion 40 (e.g., a space that is wider than distance d4). For example, space 49 may have a generally triangular cross-section. It is hypothesized that for some such embodiments, in addition to sandwiching tissue of the native valve between atrial support portion 40 and outer frame tissue anchors 54 (e.g., the tips of the outer frame tissue anchors), space 49 advantageously promotes tissue growth therewithin (e.g., between leaflet tissue and covering 23), which over time further secures prosthetic valve 20 within the native valve.

Figure 5:
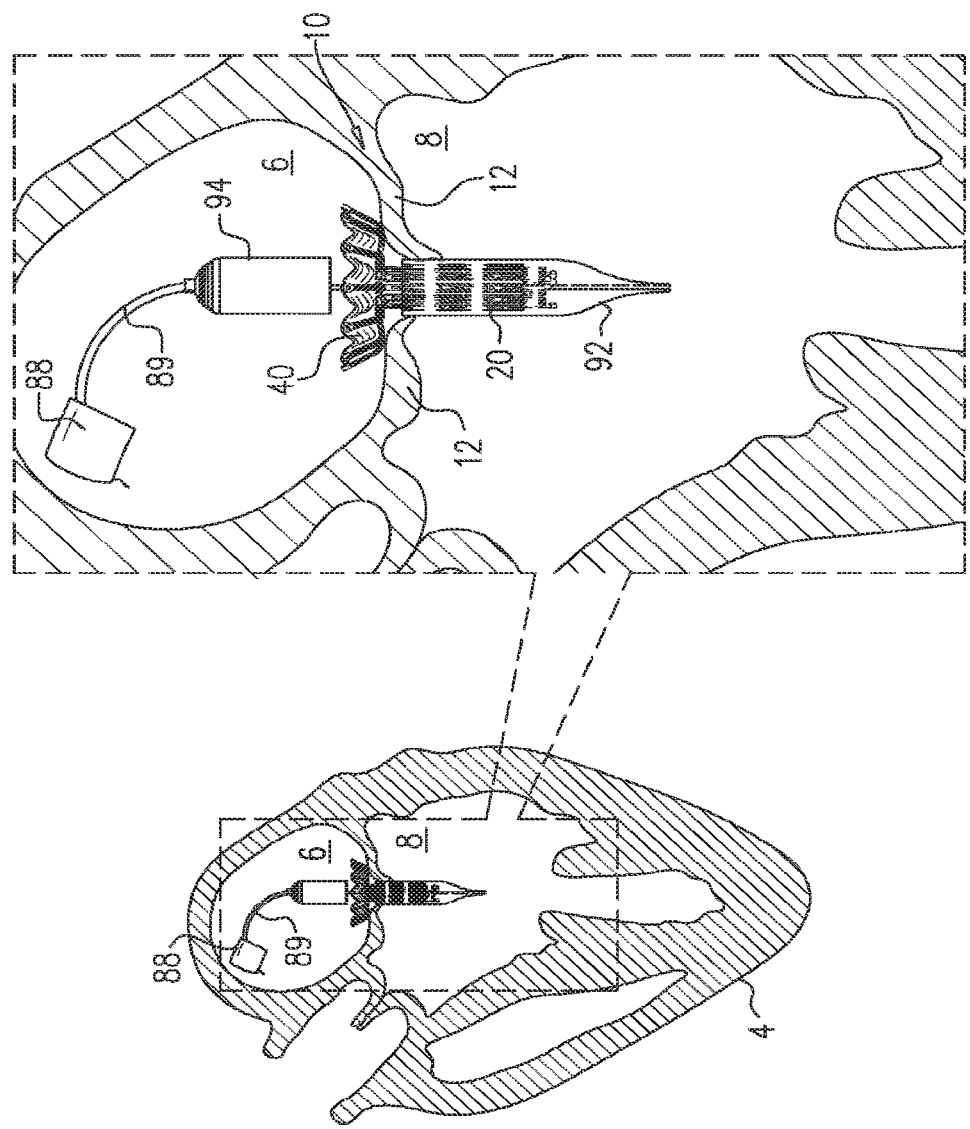
FIG. 5 is a schematic illustration of a step in the implantation of the implant, in accordance with some applications of the invention.

Reference is now made to FIG. 5, which is a schematic illustration of a step in the implantation of prosthetic valve 20, in accordance with some embodiments of the invention. Whereas FIGS. 4A-F show an implantation technique in which outer frame tissue anchors 54 are radially expanded prior to atrial support portion 40, for some embodiments the atrial support portion is radially expanded prior to the outer frame tissue anchors 54. FIG. 5 shows a step in such an embodiment.

Reference is again made to FIGS. 2A-5. As noted hereinabove, prosthetic valve 20 may be implanted by causing outer frame tissue anchors 54 to radially protrude before causing atrial support portion 40 to radially protrude, or may be implanted by causing the atrial support portion to protrude before causing the outer frame tissue anchors 54 to protrude. For some embodiments, prosthetic valve 20 is thereby configured to be deliverable in a ventricular direction (e.g., transseptally, as shown, or transapically) or in an in an atrial direction direction (e.g., transapically or via the aortic valve). Thus, for some embodiments, an operating physician may decide which delivery route is preferable for a given application (e.g., for a given subject, and/or based on available equipment and/or expertise), and prosthetic valve 20 is responsively prepared for the chosen delivery route (e.g., by loading the prosthetic valve into an appropriate delivery tool).

It is to be noted that for some embodiments, ventricular delivery of prosthetic valve 20 may be performed by expanding outer frame tissue anchors 54 first (e.g., as shown in FIGS. 4A-F) or by expanding atrial support portion 40 first (e.g., as shown in FIG. 5). Similarly, for some embodiments atrial delivery of prosthetic valve 20 may be performed by atrial support portion 40 first, or by expanding outer frame tissue anchors 54 first.

Figure 6:
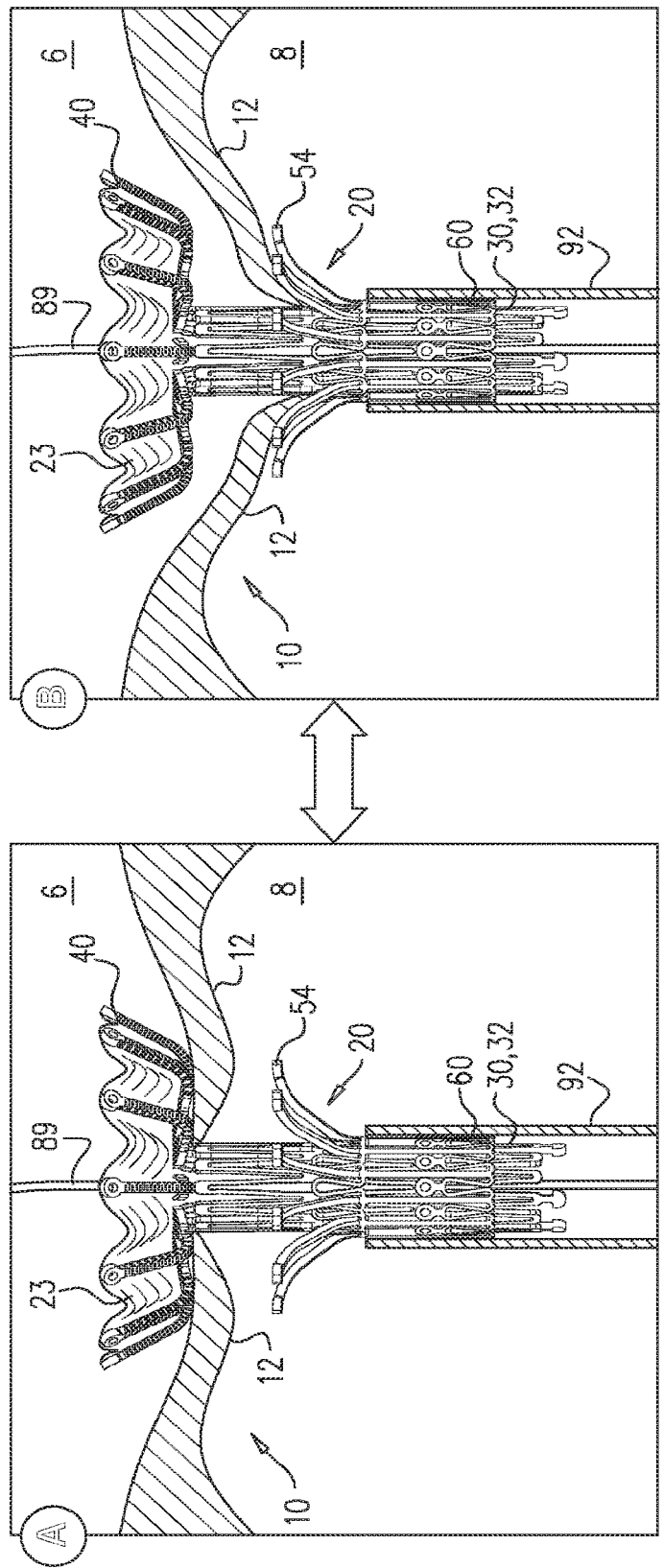
FIG. 6 is a schematic illustration of the implant, in accordance with some applications of the invention.

Reference is now made to FIG. 6, which is a schematic illustration of prosthetic valve 20, in the state and position shown in FIG. 4D, in accordance with some embodiments of the invention. For some embodiments, while prosthetic valve 20 is in the state and position shown in FIG. 4D, leaflets 12 of valve 10 are able to move, at least in part in response to beating of the heart. Frame (A) shows leaflets 12 during ventricular systole, and frame (B) shows the leaflets during ventricular diastole. For some such embodiments, blood is thereby able to flow from atrium 6 to ventricle 8, between leaflets 12 and prosthetic valve 20. It is hypothesized that this advantageously facilitates a more relaxed implantation procedure, e.g., facilitating retaining of prosthetic valve 20 in this state and position for a duration of greater than 8 minutes. During this time, imaging techniques may be used to verify the position of prosthetic valve 20, and/or positioning of leaflets 12 between atrial support portion 40 and outer frame tissue anchors 54.

Reference is made to FIGS. 7A-B and 8A-B, which are schematic illustrations of frame assemblies 122 and 222 of respective prosthetic valves, in accordance with some embodiments of the invention. Except where noted otherwise, frame assemblies 122 and 222 may be identical to frame assembly 22, mutatis mutandis. Elements of frame assemblies 122 and 222 share the name of corresponding elements of frame assembly 22. Additionally, except where noted otherwise, the prosthetic valves to which frame assemblies 122 and 222 belong are similar to prosthetic valve 20, mutatis mutandis. FIG. 7A depicts frame assembly 122 in the radially contracted state, while FIG. 7B depicts frame assembly 122 in the radially expanded state. Similarly, FIG. 8A depicts frame assembly 222 in the radially contracted state, while FIG. 8B depicts frame assembly 222 in the radially expanded state. As shown in FIGS. 7A-7B and 8A-8B, inner frame tissue anchors 146, 246 and outer frame tissue anchors 154, 254 may be positioned substantially parallel to axis ax1 when frame assembly 122, 222 is in the radially contracted state and may deflect radially outwards away from axis ax1 when frame assembly 122, 222 expands into the radially expanded state.

Frame assembly 122 includes an inner frame 130 that includes an inner frame tubular portion 132 having an atrial end 134 and a ventricular end 136. One or more projections 128 may extend from ventricular end 136 of inner frame tubular portion 132. Inner frame tubular portion 132 may also include an atrial support portion 140 that may include a plurality of inner frame tissue anchors 146 extending from inner frame tubular portion 132. Inner frame tissue anchors 146 may connect to inner frame tubular portion 132 at connection locations 145, which may be situated in an intermediate portion of inner frame tubular portion 132 (that is, between atrial end 134 and ventricular end 136). Inner frame tissue anchors 146 may include inner regions 142 and outer regions 144. As depicted in FIG. 7B, when frame assembly 122 is in the radially expanded state, inner regions 142 may extend downwards in a ventricular direction, while outer regions 144 may extend upwards in an atrial direction. Frame assembly 122 may also include an outer frame 160 that circumscribes the inner frame 130 and which includes an outer frame tubular portion 165 having an atrial end 167 and a ventricular end 169. Outer frame 160 may also include a plurality of ventricular anchoring supports 150 that each include an outer frame tissue anchor 154 extending from outer frame tubular portion 165. As depicted in FIG. 7B, outer frame tissue anchors 154 may connect to outer frame tubular portion 165 at connection points 153, and may extend radially outward to terminal ends 155. Connection points 153 may be positioned in an intermediate portion of outer frame tubular portion 165, between atrial end 167 and ventricular end 169. As also depicted in FIG. 7B, when frame assembly 122 is in the radially expanded state, the entire length of outer frame tissue anchors 154 (i.e., the length extending from connection point 153 to terminal end 155) may extend upward towards the atrium of the heart. In some embodiments, outer frame 160 includes a ring 166 to which ventricular anchoring supports 150 are coupled. Ring 166 is defined by a pattern of alternating peaks and troughs, the peaks being fixed to frame 130 at respective coupling points 152, e.g., as described hereinabove for frame assembly 22, mutatis mutandis.

As illustrated in FIG. 7A, when frame assembly 122 is in the radially contracted state, the ventricular end 136 of the inner frame tubular portion 132 may be spaced apart from the ventricular end 169 of the outer frame tubular portion 165 relative to axis ax1. In particular, ventricular end 136 of the inner frame tubular portion 132 may be positioned in a ventricular direction from the ventricular end 169 of the outer frame tubular portion. Atrial end 134 of the inner frame tubular portion 132 may be positioned in an atrial direction from the atrial end 167 of the outer frame tubular portion 165. However, as illustrated in FIG. 7B, ventricular ends 136, 169 may be configured to be substantially aligned in a common lateral plane when frame assembly 122 is in the radially expanded state. That is, ventricular ends 136, 169 may be spaced at substantially the same position along axis ax1 when frame assembly 122 is in the radially expanded state. As a result, radial expansion of prosthetic valve 120 may decrease the distance between ventricular end 136 and ventricular end 169. In addition, and as also illustrated in FIGS. 7A-7B, inner frame tubular portion 132 may have a greater axial length than outer frame tubular portion 165. For example, as illustrated in FIG. 7B, ventricular ends 136, 169 of the inner and outer tubular frame portions 132, 165, respectively, may be substantially aligned, while the atrial end 134 of the inner frame tubular portion 132 may extend in an atrial direction beyond the atrial end 167 of the outer frame tubular portion 165.

Frame assembly 222 includes an inner frame 230 that includes an inner frame tubular portion 232 having an atrial end 234 and a ventricular end 236. One or more projections 228 may extend from ventricular end 236 of inner frame tubular portion 232. Inner frame tubular portion 232 may also include an atrial support portion 240 that may include a plurality of inner frame tissue anchors 246 extending from inner frame tubular portion 232. Inner frame tissue anchors 246 may connect to inner frame tubular portion 232 at connection locations 245, which may be situated in an intermediate portion of inner frame tubular portion 232 (i.e., between atrial end 234 and ventricular end 236). Inner frame tissue anchors 246 may include inner regions 242 and outer regions 244. As depicted in FIG. 8B, when frame assembly 222 is in the radially expanded state, inner regions 242 may extend downwards in a ventricular direction, while outer regions 244 may extend upwards in an atrial direction. Frame assembly 222 may also include an outer frame 260 that circumscribes the inner frame and which includes an outer frame tubular portion 265 having an atrial end 267 and a ventricular end 269. Outer frame 260 may also include a plurality of ventricular anchoring supports 250 that each include an outer frame tissue anchor 254 extending from outer frame tubular portion 265. As depicted in FIG. 8B, outer frame tissue anchors 254 may connect to outer frame tubular portion 265 at connection points 253, and may extend radially outward to terminal ends 255. Connection points 253 may be positioned in an intermediate portion of outer frame tubular portion 265, between atrial end 267 and ventricular end 269. As also depicted in FIG. 8B, when frame assembly 222 is in the radially expanded state, the entire length of outer frame tissue anchors 254 (i.e., the length extending from connection points 253 to terminal ends 255) may extend upward towards an atrium. In some embodiments, outer frame 260 includes a ring 266 to which ventricular anchoring supports 250 are coupled. Ring 266 is defined by a pattern of alternating peaks and troughs, the peaks being fixed to frame 230 at respective coupling points 252, e.g., as described hereinabove for frame assembly 22, mutatis mutandis.

As illustrated in FIG. 8A, when frame assembly 222 is in the radially contracted state, the ventricular end 236 of the inner frame tubular portion may be spaced apart from the ventricular end 269 of the outer frame tubular portion relative to axis ax1. In particular, ventricular end 236 may be positioned in a ventricular direction from ventricular end 269 when frame assembly 222 is in the radially contracted state. In addition, as illustrated in FIG. 8B, ventricular ends 236, 269 of the inner and outer frame tubular portions 232, 265, respectively, may be configured to be substantially aligned in a common lateral plane when frame assembly 222 is in the radially expanded state. That is, ventricular ends 236, 269 may be spaced at substantially the same position along axis ax1 when frame assembly 222 is in the radially expanded state.

Whereas inner frame tissue anchors 46 of frame assembly 22 are shown as extending from atrial end 34 of inner frame tubular portion 32, inner frame tissue anchors 146 and 246 of frame assemblies 122 and 222, respectively, may extend from sites further in a ventricular direction. (This difference may also be made to frame assembly 22, mutatis mutandis.) Inner frame tubular portions 32, 132 and 232 are each defined by a repeating pattern of cells that extends around the central longitudinal axis. In some embodiments, and as shown, inner frame tubular portions 32, 132 and 232 are each defined by two stacked, tessellating rows of cells. In the radially expanded state of each inner frame tubular portion, these cells may be narrower at their atrial and ventricular extremities than midway between these extremities. For example, and as shown, the cells may be roughly diamond or astroid in shape. In frame assembly 22, each inner frame tissue anchor 46 is attached to and extends from a site 35 that is at the atrial extremity of cells of the atrial row. In contrast, in frame assemblies 122 and 222, each inner frame tissue anchor 146 or 246 is attached to and extends from a site 135 (assembly 122) or 235 (assembly 222) that is at the connection between two adjacent cells of the atrial row (alternatively described as being at the atrial extremity of cells of the ventricular row).

It is hypothesized by the inventors that this lower position of the inner frame tissue anchors, while maintaining the length of the lumen of the inner frame tubular portion, advantageously reduces the distance that the inner frame tubular portion (i.e., the ventricular end thereof) extends into the ventricle of the subject, and thereby reduces a likelihood of inhibiting blood flow out of the ventricle through the left ventricular outflow tract. It is further hypothesized that this position of the inner frame tissue anchors reduces radial compression of the inner frame tubular portion by movement of the heart, due to greater rigidity of the inner frame tubular portion at sites 135 and 235 (which is supported by two adjacent cells) than at site 35 (which is supported by only one cell).

As illustrated in FIG. 7B, when frame assembly 122 is in the radially expanded state, connection locations 145 of the inner frame tissue anchors 146 may be positioned in an atrial direction from the atrial end 167 of the outer frame tubular portion 165. As a result, outer frame tubular portion 165 may be positioned in a ventricular direction from connection locations 145 and from inner frame tissue anchors 146.

As depicted in FIGS. 7B and 8B, and as discussed above, ventricular end 169, 269 of the outer frame tubular portion 165, 265 may be substantially aligned with the ventricular end 136, 236 of the inner frame tubular portion 132, 232 when frame assembly 122, 222 is expanded. Meantime, atrial end 134, 234 of the inner frame tubular portion may 132, 232 extend in an atrial direction beyond the atrial end 167, 267 of the outer frame tubular 165, 265 when frame assembly 122, 222 is expanded. Thus, in at least some embodiments, a distance between ventricular end 169, 269 of the outer frame tubular portion 165, 265 and ventricular end 136, 236 of the inner frame tubular portion 132, 232 may be smaller than a distance between atrial end 167, 267 of the outer frame tubular portion 165, 265 and atrial end 134, 234 of the inner frame tubular portion 132, 232.

As shown, in the radially expanded state of frame assemblies 22, 122, and 222, the ventricular anchoring supports (50, 150, and 250, respectively) (and thus outer frame tissue anchors 54, 154, 254) are circumferentially staggered with the inner frame tissue anchors (46, 146, and 246, respectively). This may allow the ventricular anchoring supports 50 to move in an atrial direction between the inner frame tissue anchors during expansion of the inner frame tubular portion (32, 132 and 232, respectively), facilitating application of greater sandwiching force on tissue of the native valve. The lower position of the inner frame tissue anchors of assemblies 122 and 222 includes circumferentially shifting the position of the inner frame tissue anchors by the width of half a cell. In order to maintain the circumferential staggering of the inner frame tissue anchors 46, 146, 246 and outer frame tissue anchors 54, 154, 254, rings 166 and 266 (and thereby ventricular anchoring supports 150 and 250) are circumferentially shifted correspondingly. As a result, whereas the peaks of ring 66 generally align with connections between adjacent cells of the ventricular row of cells of inner frame tubular portion 32 (and are fixed to these sites), the peaks of rings 166 and 266 are generally aligned midway between these sites (i.e., at spaces of the cellular structure of the inner frame tubular portion). An appendages 168 (for assembly 122) or 268 (for assembly 222) facilitate fixing of the peak with respect to the tubular structure.

For assembly 122, appendages 168 are defined by inner frame 130 (e.g., by inner frame tubular portion 132 thereof) and extend (in a ventricular direction) to the peaks of ring 166, to which they are fixed. For example, each appendage 168 may define a valve-frame coupling element 131 that is fixed to a respective outer-frame coupling element 161 defined by outer frame 260. In some embodiments, appendages 168 extend from sites 135. In some embodiments, appendages 168 are integral with inner frame tubular portion 132 and/or in-plane with the inner frame tubular portion (e.g., are part of its tubular shape). As illustrated in FIG. 7B, coupling element 161 may be spaced apart from the atrial 167 and ventricular 169 ends of the outer frame tubular portion 165, while coupling element 131 may be spaced apart from the atrial 134 and ventricular 136 ends of the inner frame tubular portion 132. As a result, and as also illustrated in FIG. 7B, outer frame tubular portion 165 may have no connections to inner frame tubular portion 132 along ventricular end 169 of the outer frame tubular portion 165. Additionally, inner frame tubular portion 132 may have no connections to outer frame tubular portion 165 along ventricular end 136 of the inner frame tubular portion 132.

For assembly 222, appendages 268 are defined by outer frame 260, and extend (e.g., in an atrial direction) from the peaks of ring 266. In some embodiments, appendages 268 extend to sites 235, to which they are fixed. For example, each appendage 268 may define an outer frame coupling element 261 that is fixed to a respective inner frame coupling element 231 defined by inner frame 230 (e.g., by inner frame tubular portion 232 thereof). In some embodiments, appendages 268 are integral with outer frame 260 and/or in-plane with adjacent portions of outer frame 260, such as ring 266.

Therefore, frame assembly 122 defines a hub at site 135, and frame assembly 222 defines a hub at site 235. For some embodiments, apparatus therefore comprises: a plurality of prosthetic valve leaflets; and a frame assembly, comprising: an inner frame tubular portion (132 or 232) defined by a repeating pattern of cells, the inner frame tubular portion extending circumferentially around longitudinal axis ax1 so as to define a longitudinal lumen, the prosthetic valve leaflets coupled to the inner frame and disposed within the lumen; an outer frame (160 or 260), comprising a plurality of ventricular anchoring supports (150 or 250), distributed circumferentially around the inner frame tubular portion, each support having an outer frame tissue anchor (154 or 254); an atrial support portion (140 or 240) that comprises a plurality of inner frame tissue anchors (146 or 246) that extend radially outward from the inner frame tubular portion; and a plurality of appendages (168 or 268), each having a first end that defines a coupling element (161 or 261) via which the inner frame tubular portion is coupled to the outer frame, and a second end; wherein the frame assembly defines a plurality of hubs (135 or 235), distributed circumferentially around the longitudinal axis on a plane that is transverse to longitudinal axis ax1, each hub defined by convergence and connection of, (i) two adjacent cells of the inner frame tubular portion, (ii) an inner frame tissue anchor of the plurality of inner frame tissue anchors, and (iii) an appendage of the plurality of appendages.

Figure 9C:
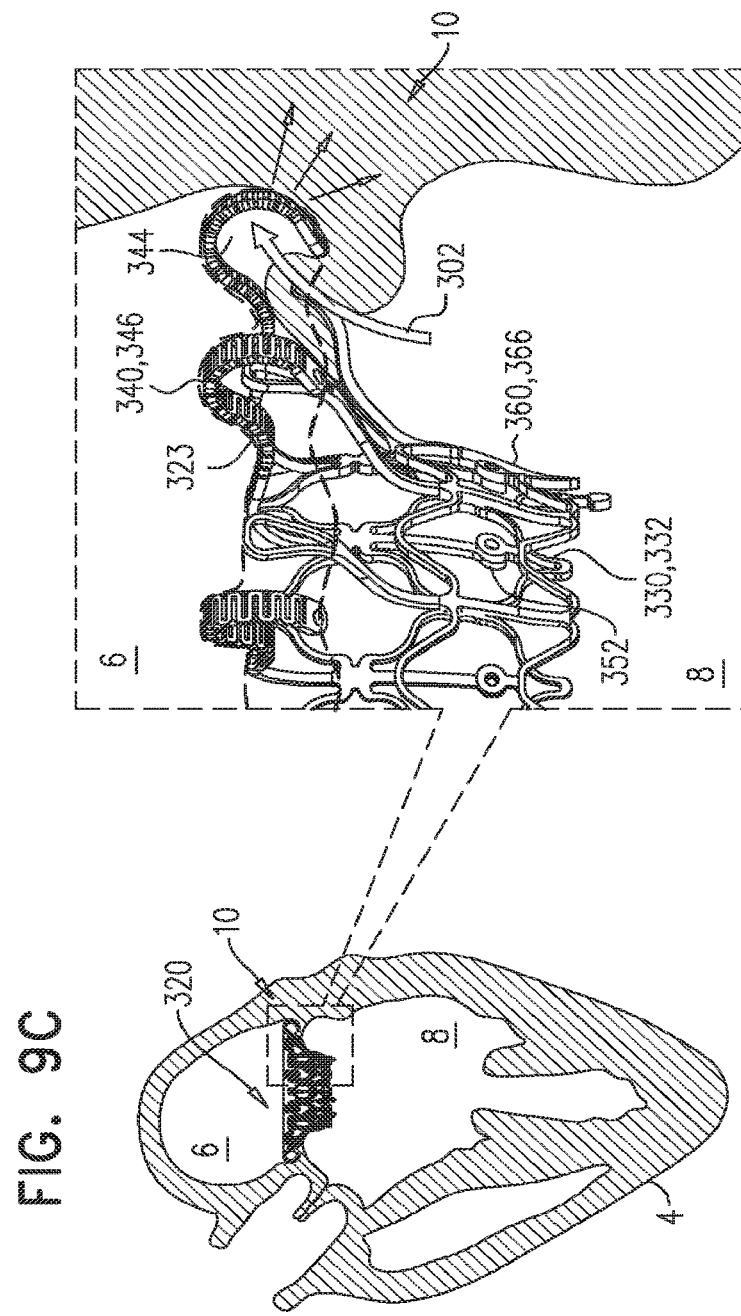

Reference is made to FIGS. 9A-C, which are schematic illustrations of an prosthetic valve 320 comprising a frame assembly 322, in accordance with some embodiments of the invention. Except where noted otherwise, frame assembly 322 is identical to frame assembly 122, and prosthetic valve 300 is identical to the prosthetic valve to which frame assembly 122 belongs, mutatis mutandis. FIG. 9A is a side-view of prosthetic valve 320, and FIG. 9B is an isometric bottom-view of the prosthetic valve.

Frame assembly 122 comprises (i) an inner frame 330 that comprises an inner frame tubular portion 332 and an atrial support portion 340 that comprises a plurality of inner frame tissue anchors 346, and (ii) an outer frame 360 that circumscribes the inner frame, and comprises a plurality of ventricular anchoring supports 350 that each comprise an outer frame tissue anchor 354. In some embodiments, outer frame 360 to which ventricular anchoring supports 350 are coupled. Ring 366 is defined by a pattern of alternating peaks and troughs, the peaks being fixed to frame 330 at respective coupling points 352, e.g., as described hereinabove for frame assembly 22 and/or frame assembly 122, mutatis mutandis.

Frame assembly 322 comprises an annular atrial support portion 340 that has an inner portion 342 that extends radially outward from the atrial portion (e.g., the atrial end) of inner frame tubular portion 332. Atrial support portion 340 further comprises one or more fabric pockets 344 disposed circumferentially around inner portion 342, each pocket of the one or more pockets having an opening that faces a ventricular direction (i.e., generally toward the ventricular end of prosthetic valve 320). In the figures, atrial support portion 340 has a single toroidal pocket 344 that extends circumferentially around inner portion 342.

In some embodiments, a covering 323 (e.g., similar to covering 23, described hereinabove, mutatis mutandis) is disposed over inner frame tissue anchors 346, thereby forming pocket 344. Further in some embodiments, inner frame tissue anchors 346 are shaped to form pocket 344 from covering 323. For example, and as shown, inner frame tissue anchors 346 may curve to form a hook-shape.

For some embodiments, portion 340 has a plurality of separate pockets 344, e.g., separated at inner frame tissue anchors 346. For some such embodiments, covering 323 is loosely-fitted (e.g., baggy) between radially-outward parts of inner frame tissue anchors 346, e.g., compared to inner portion 342, in which the covering is more closely-fitted between radially-inward parts of the inner frame tissue anchors.

FIG. 9C shows prosthetic valve 320 implanted at native valve 10. Pocket 344 is shaped and arranged to billow in response to perivalvular flow 302 of blood in an atrial direction. If ventricular systole forces blood in ventricle 8 between prosthetic valve 320 and native valve 10, that blood inflates pocket 344 and presses it (e.g., covering 323 and/or the radially-outward part of inner frame tissue anchor 346) against tissue of atrium 6 (e.g., against the atrial wall), thereby increasing sealing responsively. It is hypothesized by the inventors that the shape and orientation of pocket 344 (e.g., the hook-shape of inner frame tissue anchors 346) facilitates this pressing radially-outward in response to the pocket's receipt of blood flowing in an atrial direction (that is, towards the atrium).

Pocket(s) 344 may be used in combination with any of the prosthetic valves described herein, mutatis mutandis.

Reference is again made to FIGS. 1A-9C. It is to be noted that unless specifically stated otherwise, the term "radially outward" (e.g., used to describe atrial support portion 40 and outer frame tissue anchors 54) means portions of the element are disposed progressively further outward from a central point (such as longitudinal axis ax1 or inner frame tubular portion 32), but does not necessarily mean disposed at 90 degrees with respect to longitudinal axis ax1. For example, outer frame tissue anchors 54 may extend radially outward at 90 degrees with respect to longitudinal axis ax1, but may alternatively extend radially outward at a shallower angle with respect to the longitudinal axis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. An expandable prosthetic valve for implantation within a native heart valve, the prosthetic valve being configured for expansion from a radially-contracted state to a radially-expanded state, wherein the prosthetic valve comprises:

an expandable annular outer frame formed at least partially of outer frame struts intersecting at outer frame junctions, the annular outer frame comprising a downstream end and an upstream end opposite from the downstream end, wherein the outer frame struts along the downstream end of the annular outer frame are arranged in a first undulating configuration in which the outer frame struts extend between a first plurality of peaks and a first plurality of troughs positioned downstream from the first plurality of peaks; and an expandable inner frame situated at least partially within the annular outer frame and formed at least partially of inner frame struts intersecting at inner frame junctions, the inner frame comprising a downstream end and an upstream end opposite from the downstream end, wherein a plurality of inner frame tissue anchors are configured to extend radially-outward from the inner frame, and wherein the inner frame struts along the downstream end of the inner frame are arranged in a second undulating configuration in which the inner frame struts extend between a second plurality of peaks and a second plurality of troughs positioned downstream from the second plurality of peaks, wherein the annular outer frame and the inner frame are configured and interconnected in a manner such that radial expansion of the prosthetic valve from the radially-contracted state to the radially-expanded state decreases a distance between the downstream end of the annular outer frame and the downstream end of the inner frame, and wherein at least one of the first plurality of troughs is configured to be situated downstream from at least one of the second plurality of peaks.

2. The prosthetic valve of claim 1, wherein the at least one of the first plurality of troughs is configured to be situated downstream from the at least one of the second plurality of peaks when the prosthetic valve is in the radially-expanded state.

3. The prosthetic valve of claim 1, further comprising:
a plurality of outer frame tissue anchors configured to extend radially-outward from the annular outer frame, wherein the inner frame tissue anchors are configured to engage atrial tissue of the native heart valve and the outer frame tissue anchors are configured to engage ventricular tissue of the native heart valve.

4. The prosthetic valve of claim 3, wherein the annular outer frame comprises:
an intermediate portion extending between the upstream end of the annular outer frame and the downstream end of the annular outer frame,
wherein at least one outer frame tissue anchor extends from the intermediate portion of the annular outer frame.

5. The prosthetic valve of claim 1, wherein the inner frame comprises:
an intermediate portion extending between the upstream end of the inner frame and the downstream end of the inner frame,
wherein at least one inner frame tissue anchor extends from the intermediate portion of the inner frame.

6. The prosthetic valve of claim 1,
wherein the downstream end of the annular outer frame is devoid of connections to the inner frame, and
wherein the downstream end of the inner frame is devoid of connections to the annular outer frame.

7. The prosthetic valve of claim 1, wherein the inner frame has a greater axial length than an axial length of the annular outer frame.

8. The prosthetic valve of claim 1, wherein when the annular outer frame and the inner frame are both in the radially-contracted state, the inner frame is configured to extend beyond the downstream end of the annular outer frame in a downstream direction and beyond the upstream end of the annular outer frame in an upstream direction.

9. The prosthetic valve of claim 1, wherein when the annular outer frame and the inner frame are both in the radially-contracted state, at least one inner frame tissue anchor is configured to extend in a direction substantially parallel to a longitudinal axis of the prosthetic valve.

10. The prosthetic valve of claim 1, wherein a distance between the downstream end of the annular outer frame and the downstream end of the inner frame is smaller than a distance between the upstream end of the annular outer frame and the upstream end of the inner frame.

11. The prosthetic valve of claim 1,
wherein the outer frame struts are configured to intersect at outer frame junctions to form a plurality of closed outer frame cells having a first cell shape, and
wherein the inner frame struts are configured to intersect at inner frame junctions to form a plurality of closed inner frame cells having a second cell shape different from the first cell shape.

12. The prosthetic valve of claim 1,
wherein the outer frame struts are configured to intersect at outer frame junctions to form a plurality of closed outer frame cells, and
wherein the closed outer frame cells adjacent to the downstream end of the outer frame are configured to be chevron shaped.

13. The prosthetic valve of claim 1, wherein the outer frame junctions along the upstream end of the outer frame are offset from the first plurality of troughs, relative to a circumferential direction of the prosthetic valve.

14. The prosthetic valve of claim 1, wherein the prosthetic valve is configured to be retained within a delivery device when the prosthetic valve is in the radially-contracted state.

15. A prosthetic valve configured for implantation within a native heart valve, the prosthetic valve comprising:
an expandable annular outer frame formed at least partially of outer frame struts intersecting at outer frame junctions, the annular outer frame comprising a downstream end and an upstream end opposite from the downstream end, wherein the outer frame struts along the downstream end of the annular outer frame are arranged in a first undulating configuration in which the outer frame struts extend between a first plurality of peaks and a first plurality of troughs positioned downstream from the first plurality of peaks; and
an expandable inner frame situated at least partially within the annular outer frame and formed at least partially of inner frame struts intersecting at inner frame junctions, the inner frame comprising a downstream end and an upstream end opposite from the downstream end, wherein the inner frame struts along the downstream end of the inner frame are arranged in a second undulating configuration in which the inner frame struts extend between a second plurality of peaks and a second plurality of troughs positioned downstream from the second plurality of peaks,
wherein the inner frame has a greater axial length than an axial length of the annular outer frame,
wherein the annular outer frame and the inner frame are configured and interconnected in a manner such that radial expansion of the annular outer frame and of the inner frame decreases a distance between the downstream end of the annular outer frame and the downstream end of the inner frame, and
wherein when the prosthetic valve is in a radially-expanded state, at least one of the first plurality of troughs is configured to be situated downstream from at least one of the second plurality of peaks.

16. The prosthetic valve of claim 15, further comprising:
a plurality of inner frame tissue anchors configured to extend radially-outward from the inner frame; and
a plurality of outer frame tissue anchors configured to extend radially-outward from the annular outer frame,
wherein the inner frame tissue anchors are configured to engage atrial tissue of the native heart valve and the outer frame tissue anchors are configured to engage ventricular tissue of the native heart valve.

17. The prosthetic valve of claim 15,
wherein the downstream end of the annular outer frame is devoid of connections to the inner frame, and
wherein the downstream end of the inner frame is devoid of connections to the annular outer frame.

18. The prosthetic valve of claim 15, wherein the inner frame is configured to extend beyond the downstream end of the annular outer frame in a downstream direction and beyond the upstream end of the annular outer frame in an upstream direction.

19. The prosthetic valve of claim 15,
wherein the outer frame struts are configured to intersect at outer frame junctions to form a plurality of closed outer frame cells having a first cell shape, and
wherein the inner frame struts are configured to intersect at inner frame junctions to form a plurality of closed inner frame cells having a second cell shape different from the first cell shape.

20. The prosthetic valve of claim 15, wherein the outer frame junctions along the upstream end of the outer frame are offset from the first plurality of troughs, relative to a circumferential direction of the prosthetic valve.

* * * * *